(12) United States Patent
Kurihashi

(10) Patent No.: US 7,785,285 B2
(45) Date of Patent: Aug. 31, 2010

(54) LACRIMAL PUNCTUM PLUG

(75) Inventor: Katsuaki Kurihashi, Hamamatsu (JP)

(73) Assignee: MLC Limited Company (JP)

( * ) Notice: Subject to any disclaimer, the term of this patent is extended or adjusted under 35 U.S.C. 154(b) by 631 days.

(21) Appl. No.: 10/524,824

(22) PCT Filed: May 26, 2004

(86) PCT No.: PCT/JP2004/007552
§ 371 (c)(1), (2), (4) Date: Jan. 6, 2006

(87) PCT Pub. No.: WO2004/105658
PCT Pub. Date: Dec. 9, 2004

(65) Prior Publication Data
US 2006/0106352 A1 May 18, 2006

(30) Foreign Application Priority Data
May 30, 2003 (JP) ............................. 2003-154328

(51) Int. Cl.
A61M 5/00 (2006.01)
A61M 35/00 (2006.01)
A61B 17/00 (2006.01)

(52) U.S. Cl. .................... 604/9; 604/294; 128/887; 623/905

(58) Field of Classification Search ............... 604/8–10, 604/289, 290, 294, 264, 265, 285, 523, 530, 604/540, 541; 606/204.25; 128/887; 623/4.1, 623/10, 11.11, 905
See application file for complete search history.

(56) References Cited

U.S. PATENT DOCUMENTS

| 5,171,270 | A | * | 12/1992 | Herrick | ................... 623/11.11 |
| 5,417,651 | A | * | 5/1995 | Guena et al. | ................... 604/8 |
| 5,741,292 | A | * | 4/1998 | Mendius | ..................... 606/191 |
| 6,027,470 | A | * | 2/2000 | Mendius | ......................... 604/8 |
| 6,168,623 | B1 | * | 1/2001 | Fogarty et al. | ............... 623/1.3 |
| 6,238,363 | B1 | * | 5/2001 | Kurihashi | ...................... 604/8 |
| 6,290,684 | B1 | * | 9/2001 | Herrick | ...................... 604/294 |
| 2003/0125748 | A1 | * | 7/2003 | Li et al. | ........................ 606/99 |

(Continued)

FOREIGN PATENT DOCUMENTS

JP 09-276318 10/1997

(Continued)

OTHER PUBLICATIONS

Written Opinion for PCT/JP2004/007552.*

(Continued)

Primary Examiner—Leslie R Deak
Assistant Examiner—Philip R Wiest
(74) Attorney, Agent, or Firm—Bacon & Thomas, PLLC

(57) ABSTRACT

A punctal plug inserted into the punctum-canaliculus, includes a shaft, a tip portion attached to one end of said shaft and a brim attached to the other end of said shaft, and a thin member penetrated into either one or all 3 out of said tip portion, shaft and brim, or said tip portion and shaft, or said shaft and brim. The thin member is thread 0.05 mm or less in diameter. The brim is disk shaped and the diameter of the brim is far smaller than the diameter of the tip. A protuberance is attached to the tip portion.

14 Claims, 52 Drawing Sheets

U.S. PATENT DOCUMENTS

2004/0092857 A1* 5/2004 Clayman et al. ............... 604/8

FOREIGN PATENT DOCUMENTS

| JP | 11-047183 | 2/1999 |
|---|---|---|
| JP | 2000-070296 | 3/2000 |
| JP | 2002-529144 | 9/2002 |

OTHER PUBLICATIONS

White et al., Iatrogenic Complications Related ot the Use of Herrick Lacrimal Plugs, Ophthalmology, vol. 108, No. 10, Oct. 2001, pp. 1835-1837.

Jones et al., "Retrospective Safety Study of the Herrick Lacrimal Plug: A Device Used to Occlude the Lacrimal Canaliculus", The CLAO Journal, vol. n8, No. 4, 2002, pp. 206-210.

Gerding et al., "Symptomatic Cicatrizial Occlusion of Canaliculi After Insertion of Herrick Lacrimal Plugs", Am. J. of Ophthalology, Nov. 2003, pp. 926-928.

Tost et al., "20-MHzUltrasound and Its Value in Imaging of Lacrimal Plugs", Ophthalmologica, 2004, vol. 218, pp. 14-19.

Hurwitz et al., "Identification of retained intracanalicular plugs with ultrasound biomicroscopy", Can. J. Ophthalmol, vol. 39, No. 5, 2004, pp. 534-537.

Dolan et al., "Common canalicular obstruction secondary to the use of Herrick lacrimal plugs, requiring endoscopic dacryocystorhinostomy", The J. of Laryngology & Otology, 2009, vol. 1, pp. 129-130.

Baxter et al., "Punctal plugs in the management of dry eyes", Ocul Surf, Oct. 2004, vol. 2, No. 4, Abstract.

* cited by examiner

FIG. 45
(A)
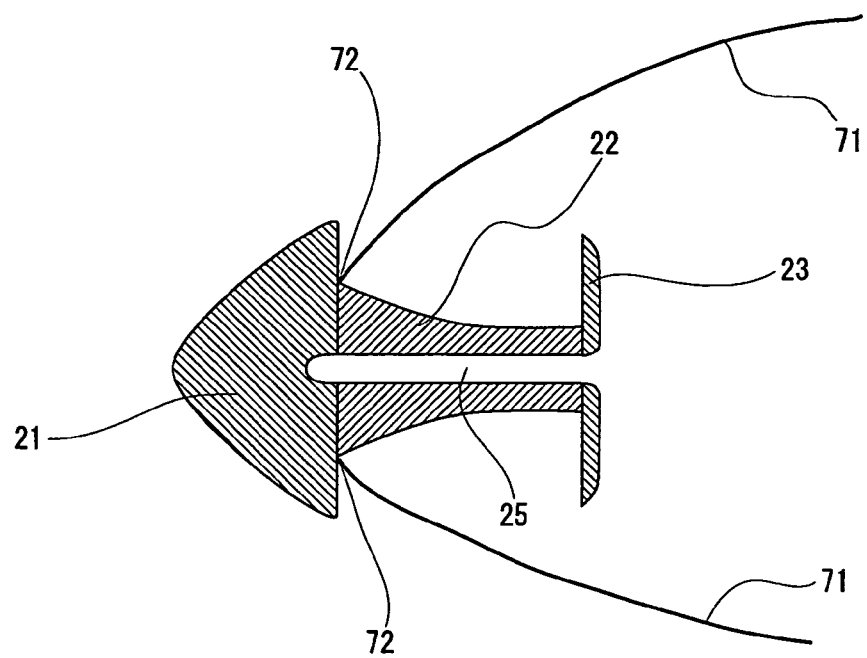
(B)
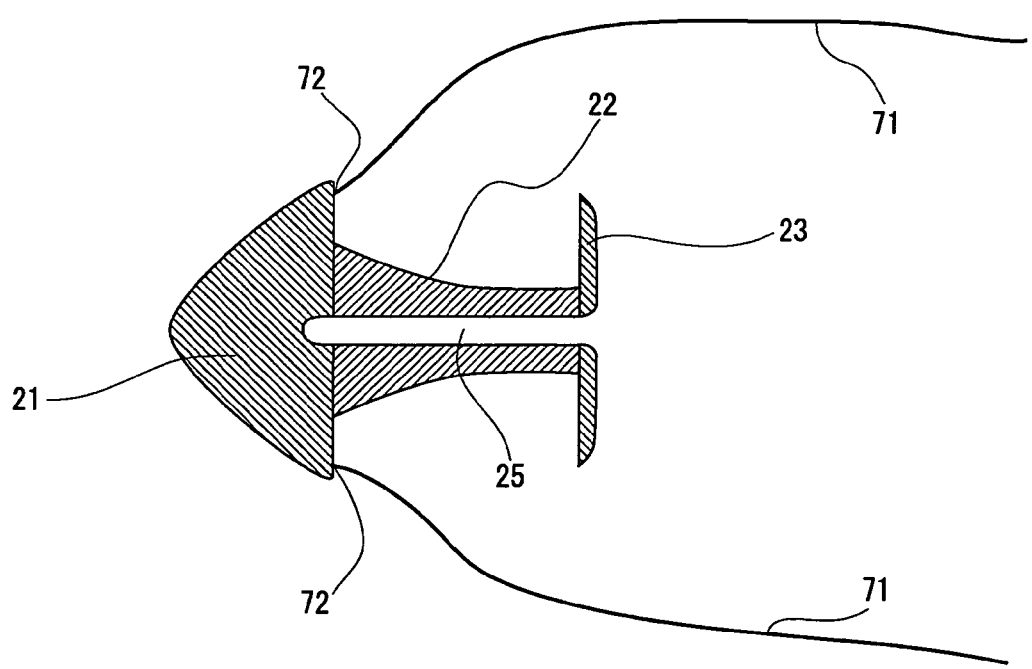

FIG. 47
(A)
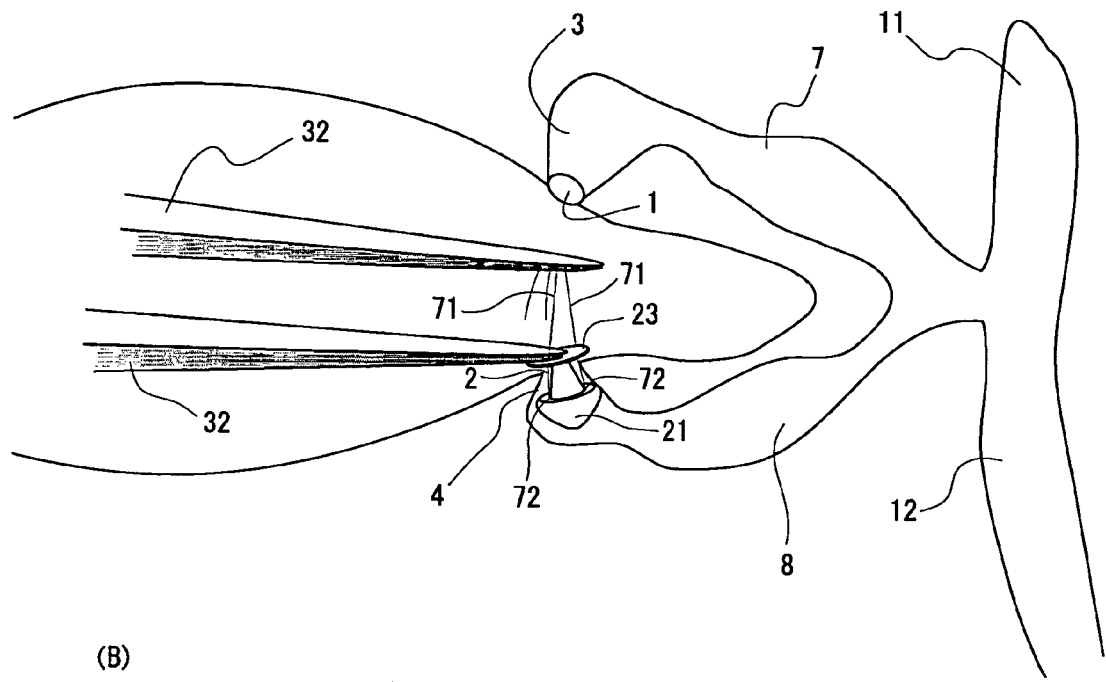
(B)
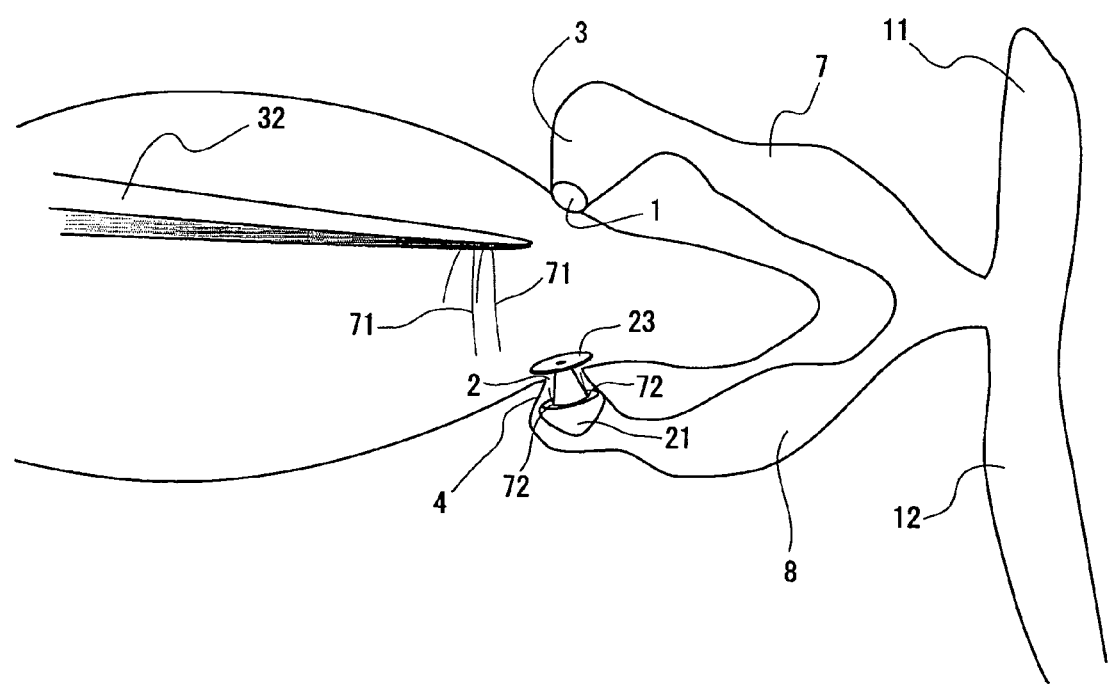

F I G. 5 3
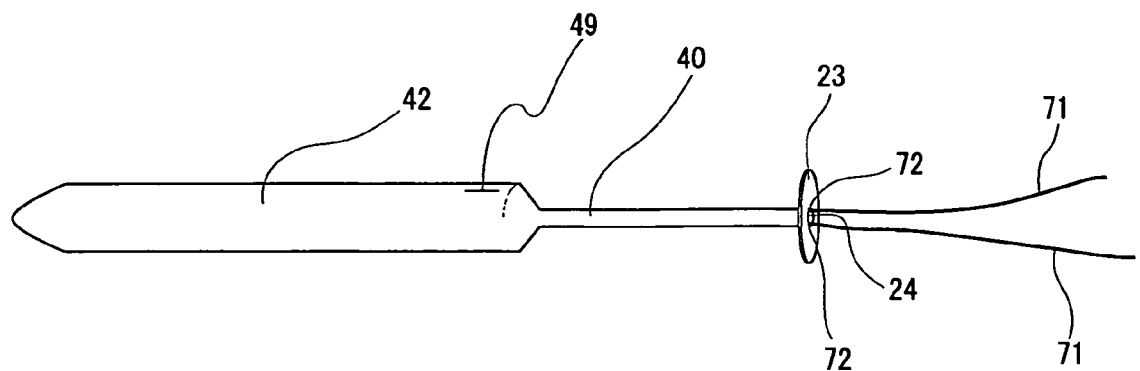
F I G. 5 4
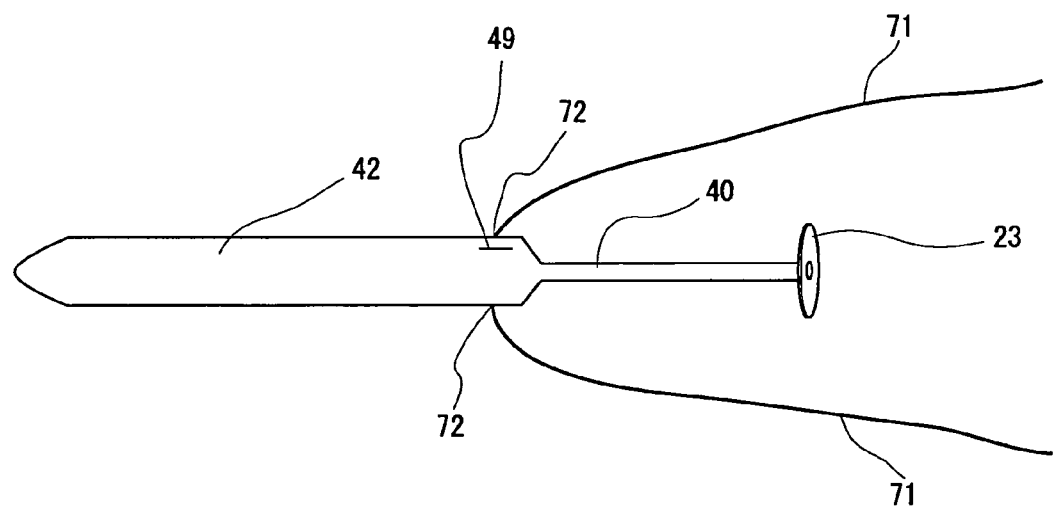

F I G. 5 8
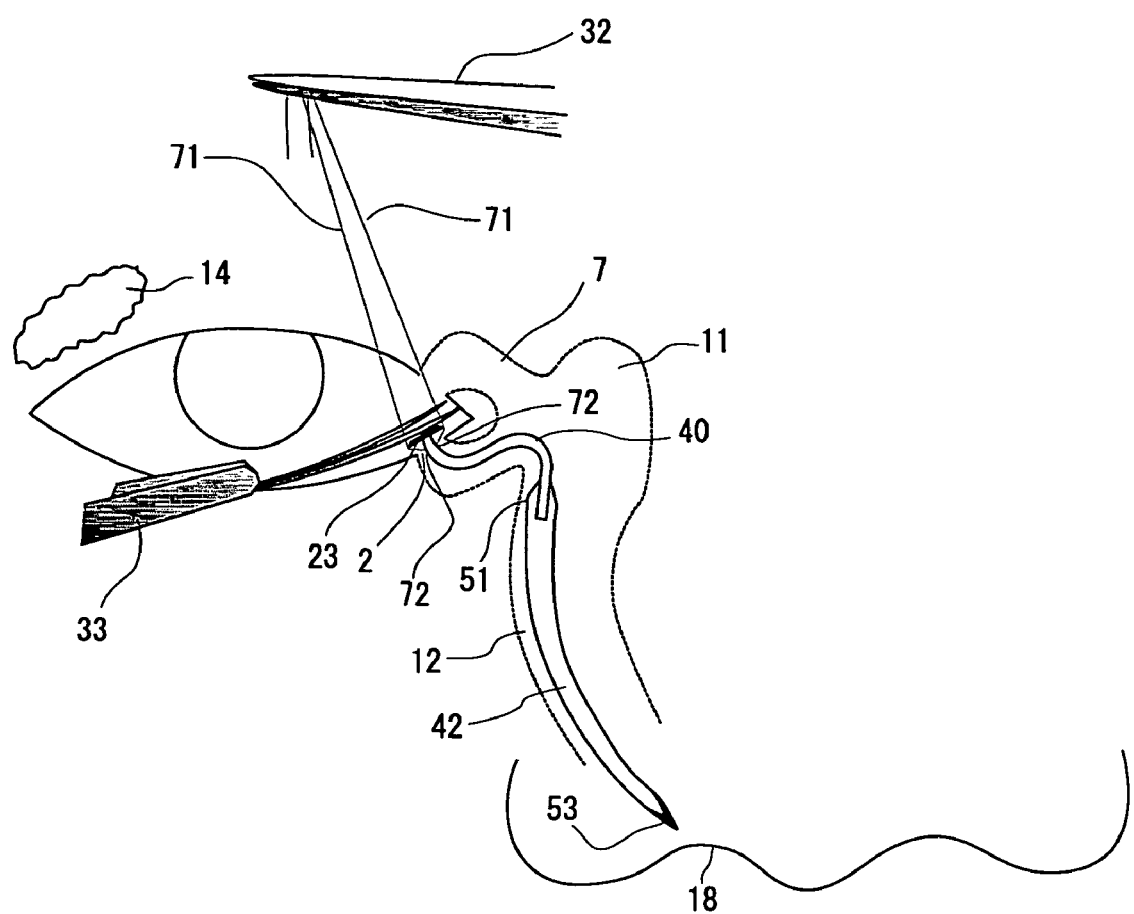

F I G. 5 9
(A)
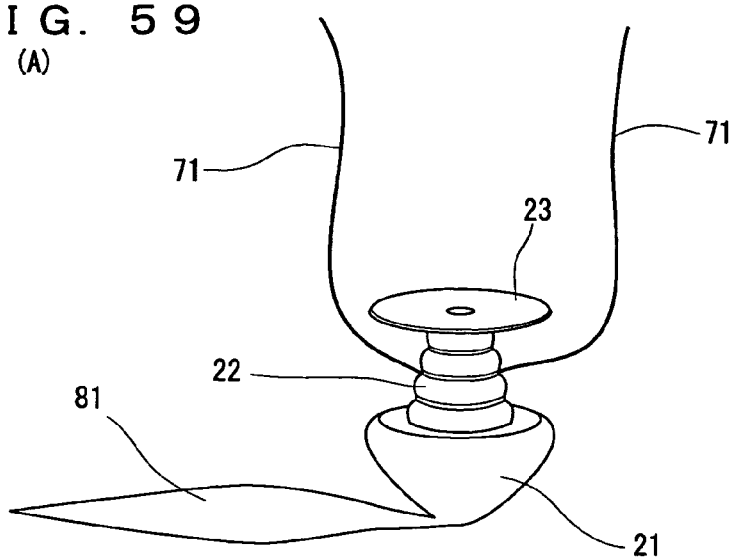
(B)
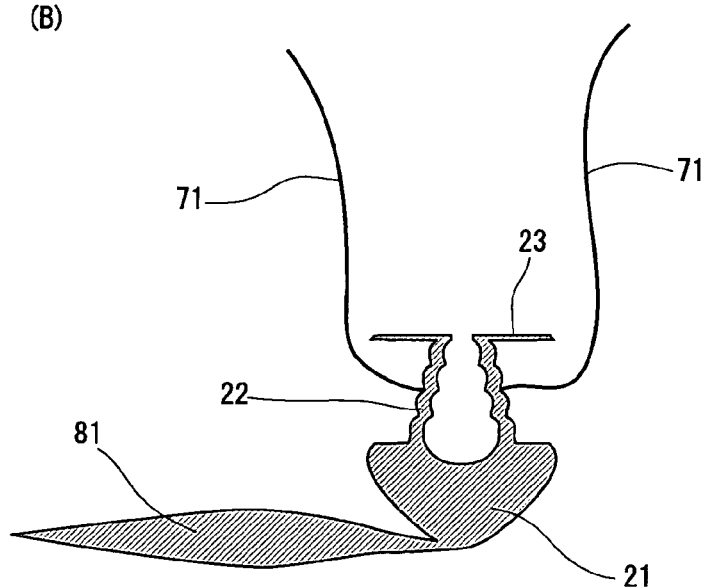
(C)
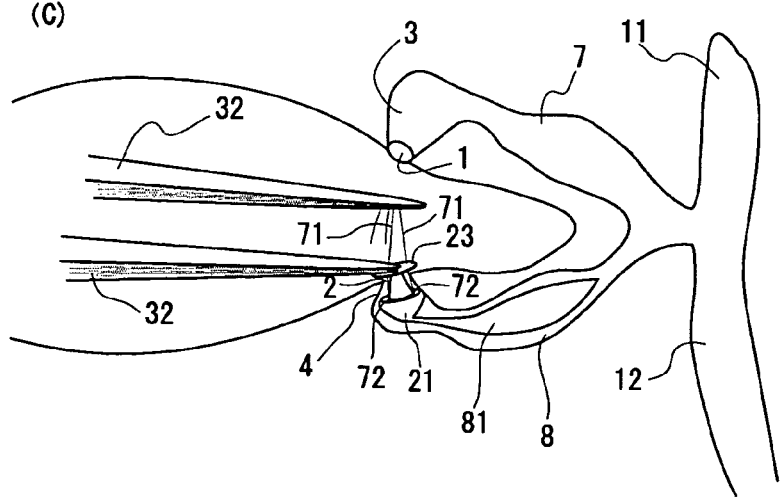

a < b

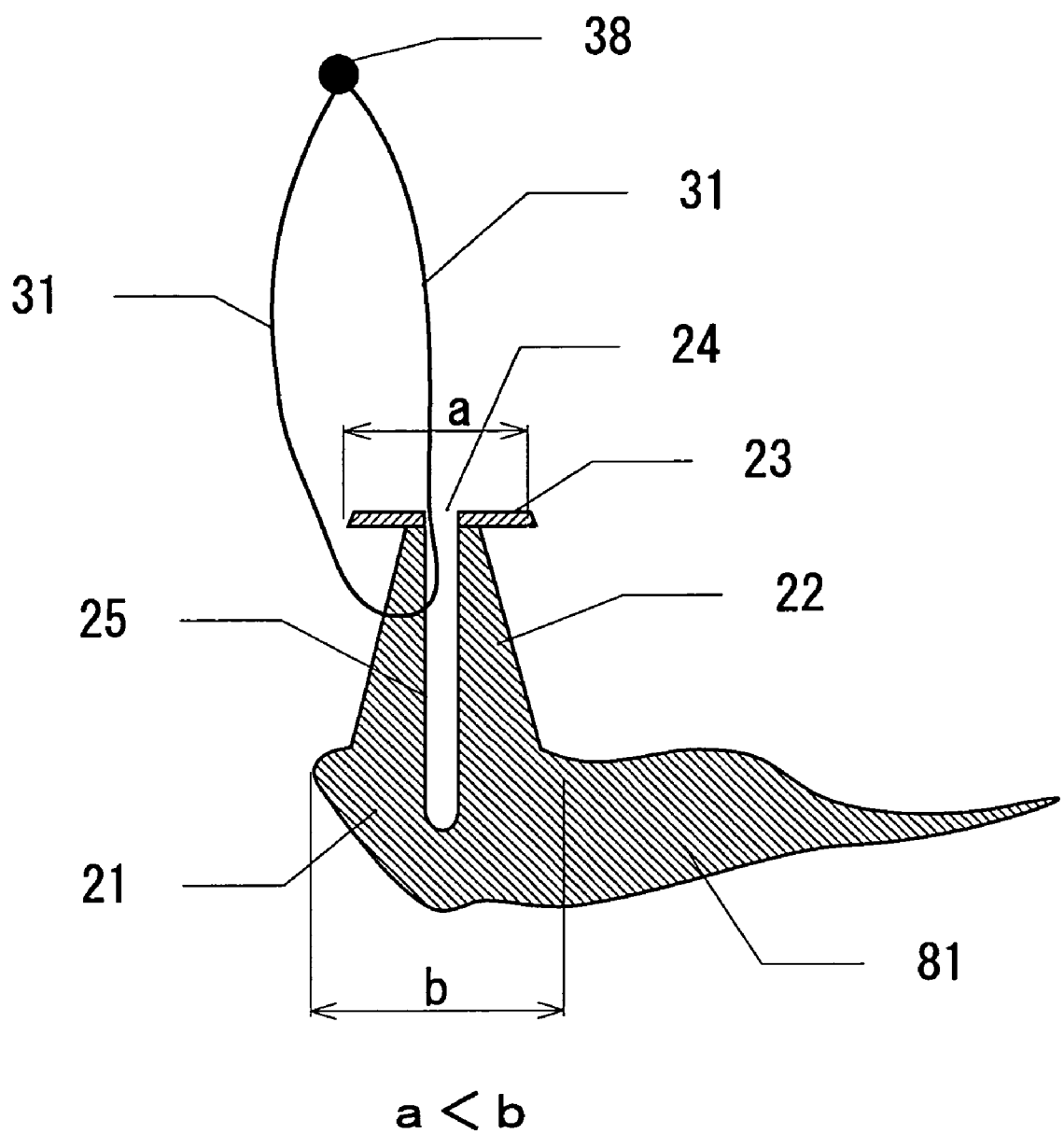
F I G. 6 4
a < b mm

LACRIMAL PUNCTUM PLUG

CROSS-REFERENCE TO RELATED APPLICATIONS

This application is a National Phase Application (35 USC 371) of PCT/JP2003/007552 and claims priority of Japanese Application No. 2003-154328 filed May 30, 2003.

BACKGROUND OF THE INVENTION

This invention relates to a punctal plug and an apparatus for intubation of the lacrimal duct for treatment of dry eye.

RELATED ART

As shown in FIG. 1, the lacrimal gland 14 secretes tears which drain into the inferior nasal meatus 18 via the lacrimal duct after moistening the ocular surface 17 having the cornea 15 and conjunctiva 16. The lacrimal duct consists of the upper punctum 1, lower punctum 2, vertical portion of the upper canaliculus 3, vertical portion of the lower canaliculus 4, boundary portion between the upper vertical and horizontal portions 5, boundary portion between the lower vertical and horizontal portions 6, upper horizontal portion 7, lower horizontal portion 8, common canaliculus 9, internal common punctum 10, lacrimal sac 11 and nasolacrimal duct 12. The lower end 13 of the nasolacrimal duct 12 opens into the inferior nasal meatus 18. The inner space of the horizontal portion 7, 8 is spindle shaped. It is known that negative pressure is generated in the canaliculus. For example, see Katsuaki Kurihashi: Dacriology—Clinical dacriology—Medical Aoi Shuppan Inc., Tokyo, 1998. The size of the opening of the punctum is 0.1-0.8 mm$^2$ (average 0.3 mm$^2$). For example, see Carter K D et al: Size variation of the lacrimal punctum in adults. Ophthalmic Plast Reconstr Surg 4: 231, 1988. The diameter of the opening of the punctum for Japanese is 0.1-0.5 mm. For example, see Shigako Suzuki: Study of Slit lamp examination for eye disease. No. 2 Study on the punctum. Rinsho Ganka (Jpn J Ophthalmol) 10: 114, 1956.

In patients with dry eye having hypofunction of the lacrimal gland and tear deficiency, tears, which are very important for the eye, immediately drain away via the lacrimal duct.

To suppress the tear drainage, occlusion of the upper punctum 1 and/or lower punctum 2 using electric cautery or argon laser is performed. Occlusion using a punctal plug (mentioned later) inserted into the upper punctum 1 and lower punctum 2 is also performed.

By blocking the upper punctum 1 and lower punctum 2 like this, tears are accumulated in the conjunctival sac and dry eye symptoms disappear in many cases.

Dry eye symptoms include asthenopia, waking irritation, grittiness, foreign body sensation, scratchiness, soreness, difficulty to open the eyes in an air conditioned room, injection, burning and so on.

Recently, aggravation of dry eye symptoms by spending time in front of a monitor has become a problem. This is due to the fact that evaporation of tears is accelerated in individuals with tear deficiency by decreased frequency of blinking which is induced by looking at a monitor.

Artificial tears are added as eyedrops in another treatment of dry eye. But the ingredients of artificial tears are far from those of natural tears. It is best for eyes to be moistened with natural tears. Therefore, the treatment of punctal occlusion is superior.

Unlike artificial tears, tears contain lysozyme, lactoferrin, immunoglobulin, and so on which protect the eyes from bacteria and viruses. And some artificial tears contain a preservative which is harmful to the eye.

Tears also have an optical role wherein tears smoothen the microscopically irregular surface of the cornea 15 to improve eyesight, a lubricanting role wherein tears act as a lubricant and the movement of the eyelids become smooth. Artificial tears are not expected to play these various roles, among others.

Therefore, occlusion of the upper punctum 1 and/or lower punctum 2 to wet the eye with natural tears is superior. But punctal occlusion by argon laser, etc may induce epiphora postoperatively. In such a case, punctal and canalicular surgery are needed to reconstruct canaliculi and puncta.

The use of a punctal plug is superior because a punctal plug can be removed easily in such cases.

From this point of view, in 1975 Freeman reported a punctal plug as shown in FIG. 2 for the treatment of dry eye. For example, see Freeman, J M: The punctum plug: evaluation of a new treatment for dry eye. Trans Am Acad Ophthalmol Otolaryngol 79: op 874-879, 1975.

The punctal plug shown in FIG. 2 consists of the tip portion 21, shaft 22, brim 23 and there is a hole 24 in the center of brim 23. The hole 24 is continuous with a tubular lumen 25 of shaft 22 and the lumen 26 with a closed end 27 of the tip portion 21. The punctal plug shown in FIG. 2 measures 2.8 mm in total length, 1.5~2.0 mm in diameter of brim, 0.7 mm in height of brim, 1.5 mm in length of shaft and 0.7 mm in diameter of shaft.

The punctal plug in FIG. 2 is used as shown in FIG. 3. The punctal plug is inserted into puncta 1, 2 and vertical portion of canaliculus 3, 4 and the total length of the puncta 1, 2 and vertical portions of canaliculus 3, 4 is 2.5 mm on the average. Therefore, the total length 2.8 mm of the punctal plug is too long. Consequently, the brim 23 touches the cornea 15 and not infrequently induces a foreign body sensation.

FIG. 4 shows a punctal plug of the FCI company. This is also used for the treatment of dry eye in Japan. For example, see Junzo Hirano & Miki Hirano: Experience of the treatment for a case with Stevens-Johnson syndrome with severe keratoconus, Japanese Review of Clinical Ophthalmology 91: 41-44, 1997.

The punctal plug in FIG. 4 is a miniaturized one. This punctal plug measures 1.7 mm in total length, 1.5 mm in diameter of brim 23, and is miniaturized as a whole. It measures 0.1 mm in thickness of brim 23 which inclines 200 against the shaft 22.

The punctal plug in FIG. 4 also consists of the tip portion 21, shaft 22 and brim 23, and as in the punctal plug as shown in FIG. 2, hole 24 is continuous with the lumen 25 with closed end 27.

In use, the tip of the punctal plug is pushed into the lacrimal duct to or near the boundary portion 5, 6 between the vertical portion 3, 4 and horizontal portion 7, 8 of canaliculus, by a metal probe which is inserted from the hole 24 until the closed end 27.

FIG. 5 shows a punctal plug with a tapered shaft form. This plug is also miniaturized and consists of the tip portion 21, shaft 22 and brim 23. As in the punctal plug shown in FIG. 2, the hole 24 is continuous with lumen 25 with a closed end 27. The shaft 22 becomes gradually smaller as it tapers toward the brim 23.

Although corneal disorder is hardly induced by such a miniature punctal plug, the miniature punctal plug can also migrate into the vertical portion of the upper canaliculus 3,4 as shown in FIG. 6, the horizontal portion of canaliculus 7, 8 as shown in FIG. 7, and as shown in FIG. 8 into the lacrimal sac 11 and nasolacrimal duct 12, resulting in canaliculitis and dacryocystitis which sometimes need surgical intervention (For example, see Rumelt S et al: silicone punctal plug migration resulting in dacryocystitis and canaliculitis. Cornea 16: 377-399, 1997.). It is a problem that the punctal plug lodged in the lacrimal passage cannot be detected by X-ray.

Furthermore, as shown in FIG. 2, FIG. 4 and FIG. 5, the edges 28 of the tip portion 21 of either punctal plug are angular and sometimes stimulate canaliculus, resulting in the growth of pyogenic granuloma (For example, see Rapoza P A & Ruddat M S: Pyogenic granuloma as a complication of silicone punctal plug. Am J Ophthalmol 113: 454-455, 1992).

Stimulation by the tip 29 of punctal plug sometimes induces canalicular obstruction between the vertical portion 3, 4 and horizontal portion of canaliculus (For example, see Fayet B et al: Sténoses canaliculaires compliquant la pose de bouchos lacrymaux. Incidence et mécanismes, J Fr Ophthalmol 15: 25-33, 1992.)

Granuloma sometimes pushes the punctal plug out of the puncta.

The shaft of the punctal plug shown in FIG. 9 is accordion-shaped, the brim becomes smaller with a diameter 1 mm, and the stimulus to the eyeball decreases all the more. (For example, see Jp Patent No. 2002-529144.)

Though there is the above advantage when a brim is smaller, it can easily get lodged inside the lacrimal duct during insertion. Actually, in Japan, it happens often. It is the present condition that the plug is left in place as the punctum-canaliculus must be incised to take the plug out when a brim is lodged inside the lacrimal duct. The smaller the brim of the punctual plug, the better the comfort for the patient. However, conversely the brim is more easily lodged inside the lacrimal duct when a punctal plug with a smaller brim is inserted.

It follows, then, that it is difficult to set the diameter of a brim at less than 1 mm with the present technology when the diameter of the tip is 1 mm. The size of the opening of the lacrimal punctum has an individual variation of 0.1-0.5 mm in diameter. As shown in FIG. 10, a brim can easily be lodged inside the lacrimal duct at the time of insertion though the patients comfort is increased when the diameter of the brim is 1 mm or less. If the punctal plug can be inserted precisely and safely, the diameter of the brim can be made smaller, possibly less than 1 mm.

SUMMARY OF THE INVENTION

This invention aims at providing a punctal plug with a brim smaller than a conventional one to improve comfort and which also can be inserted more safely and surely into the lacrimal duct.

One of the means for solution according to the present invention is a punctal plug having a shaft, a tip portion connected with one end of said shaft and a brim connected with the other end of said shaft wherein a prescribed length of a very thin member, for example, a thread, is inserted into either one of said tip portion, shaft, and brim, or into said tip portion and shaft, or into said shaft and brim.

Another means for solution according to the present invention is an apparatus for intubation of the lacrimal duct having a thin, soft tube with a sufficient length to cover the distance between the lacrimal sac and the punctum, the punctal plug fixed at one end of said thin tube and the thick heavy tube fixed at the other end of said thin tube wherein a very thin member, for example a thread is inserted into one or two of said punctal plugs, thin and/or thick tubes.

Another means for solution according to the present invention is a device for intubation of the lacrimal duct having a thin, soft tube with a sufficient length to cover the distance between the lacrimal sac and punctum, a brim fixed at one end of said thin tube and a thick tube fixed at the other end of said thin tube, wherein a very thin member, for example a thread is inserted into one or two out of said brim, thin tube and/or thick tubes.

A suitable example of the thin member is thread 0.05 mm or less in diameter.

The present inventor has continued in earnest research for many years an apparatus for intubation of the lacrimal duct such as a punctal plug for the treatment of dry eye which can be used easily with little pain to the patient, and can be inserted precisely, quickly and safely, is not easily dislocated, and can be removed easily after attaining the purpose of treatment. For example, see Jp Patent No. 2000-70296. U.S. Pat. No. 6,383,192 B1.

The present invention is an improved apparatus for intubation of lacrimal duct developed by the present inventor. Especially, the present invention prevents the accident which occurs during insertion of a punctal plug and apparatus for intubation of lacrimal duct, resulting in marked improvement of safety, and improves comfort for the wearer by providing a smaller brim.

The punctal plug according to the present invention consists of a shaft, a brim attached to one end of said shaft, and a tip attached to the other end of said shaft and as shown in FIG. 11~26, a very thin thread is penetrated into a part or the whole body of the punctal plug. This thin thread is used to pull out the brim which is lodged in the canaliculus, that is, by pulling both sides of the thread simultaneously, the brim included in the canaliculus can be easily pulled out.

As shown in FIG. 31, other apparatus for intubation of lacrimal duct according to the present invention, consists of a thin, soft plastic tube with a sufficient length to reach from the puncta to the lacrimal sac, a punctal plug attached to one end of said thin tube, and a thick, heavy plastic tube attached to the other end of said thin tube, and a thin thread is penetrating one or two out of said punctal plug, thin tube and thick tube, when the brim is lodged in the lacrimal duct, the brim can be pulled out of the punctum by pulling both sides of the thread. In this apparatus for intubation of lacrimal duct inserted into the lacrimal duct, the thick, heavy tube attached to one end of the thin tube, pulls the thin tube downward and makes the punctal plug attached to the other end of the thin tube more stable. With the help of gravity the thick heavy tube running almost perpendicularly pulls the thin tube running almost horizontally which is connected with the upper end of said thick tube.

As shown in FIG. 34~35, still other apparatus for intubation according to the present invention, consists of a thin, soft plastic tube with a sufficient length to cover the distance between the punctum and the lacrimal sac, the brim attached to one end of said thin tube and a thick heavy tube attached to the other end of said thin tube, and a very thin thread is penetrated into one or two out of the brim, thin tube and thick tube. This thread enables a brim lodged in the lacrimal duct to be pulled out. Because the thin tube is drawn by the thick and heavy tube, the brim attached to said thin tube can seal the punctum. Most parts of the thin tube exists in the canaliculus which runs almost horizontally. The thick heavy tube exists in the sac—lacrimal duct which runs almost perpendicularly and tends to move downward by gravity. Therefore, the thin tube running horizontally, which is fixed at the upper end of the thick and heavy tube, is pulled.

It is preferable to use nylon 0.02-0.05 mm in diameter or other threads difficult to be broken in the same diameter for the present invention.

9-0 nylon with a very thin needle having a round edge or 10-0 nylon with a very thin needle having a round edge is used to enable apparatus for intubation of the lacrimal duct such as the punctal plug etc to be penetrated by thread without damage to said punctal plug and apparatus for intubation of the lacrimal duct.

However, it is more preferable to set the thread during manufacturing of the apparatus for intubation of the lacrimal duct such as punctal plug etc so as not to damage the main body, compared to setting the thread later.

The brim of the apparatus for intubation of the lacrimal duct such as punctal plug etc is 0.7~2.0 mm in diameter, and in the punctal plug only, small brims also are useful. In the apparatus for intubation of the lacrimal duct having the thin tube and thick tube, it is necessary to use a brim with large diameters compared to a brim of a punctal plug because the brim is pulled nasally as described already. In the punctal plug with a thread, the brim 0.3~1.0 mm in diameter is appropriate and in the apparatus for intubation of the lacrimal duct with the thin and thick tubes, the brim 0.5~1.5 mm in diameter is appropriate.

In conventional punctal plugs, the smallest disc shaped brim is 1 mm in diameter when the diameter of the tip is 1 mm.

This is based on the fact that according to the prior art, the brim 23 less than 1 mm in diameter is easily included in the lacrimal passage when the diameter of the tip portion 21 is 1 mm.

In the present invention, each person can select a minimally sized brim individually fit for each of them because the brim of any punctal plug lodged in the lacrimal duct and any apparatus with a brim for intubation of lacrimal duct, can be pulled out by the thread. For example, if the opening of punctum is 0.1 mm in diameter, a small brim 0.5 mm or less in diameter can be selected for a threaded punctal plug having a tip portion 1 mm in diameter, that is, in the threaded punctal plug according to the present invention, the diameter of the brim (a) can be far smaller than the diameter of the tip (b).

BRIEF DESCRIPTION OF THE DRAWINGS

FIG. 45A is a schematic diagram showing one condition of a punctal plug according to the present invention.

FIG. 45B is a schematic diagram showing the other condition of the punctal plug in FIG. 45A.

FIG. 47A is an explanatory diagram showing how to insert a punctal plug according to the present invention.

FIG. 47B is an explanatory diagram showing how to insert a punctal plug according to the present invention.

FIG. 53 is an explanatory diagram showing how to use other apparatus for intubation with thread according to the present invention.

FIG. 54 is a schematic diagram showing other apparatus for intubation according to the present invention.

FIG. 58 is an explanatory diagram showing how to use other apparatus for intubation with thread according to the present invention.

FIG. 59A is a schematic diagram showing an apparatus for intubation with thread according to the present invention.

FIG. 59B is a sectional view corresponding to FIG. 59A.

FIG. 59C is an explanatory diagram to explain how to use of the apparatus in FIG. 59A.

FIG. 64 is a sectional view to explain an outline of other punctal plugs with thread according to the present invention.

EMBODIMENT

Embodiments of the present invention will be explained by referring to the accompanying drawings.

Figure 1:
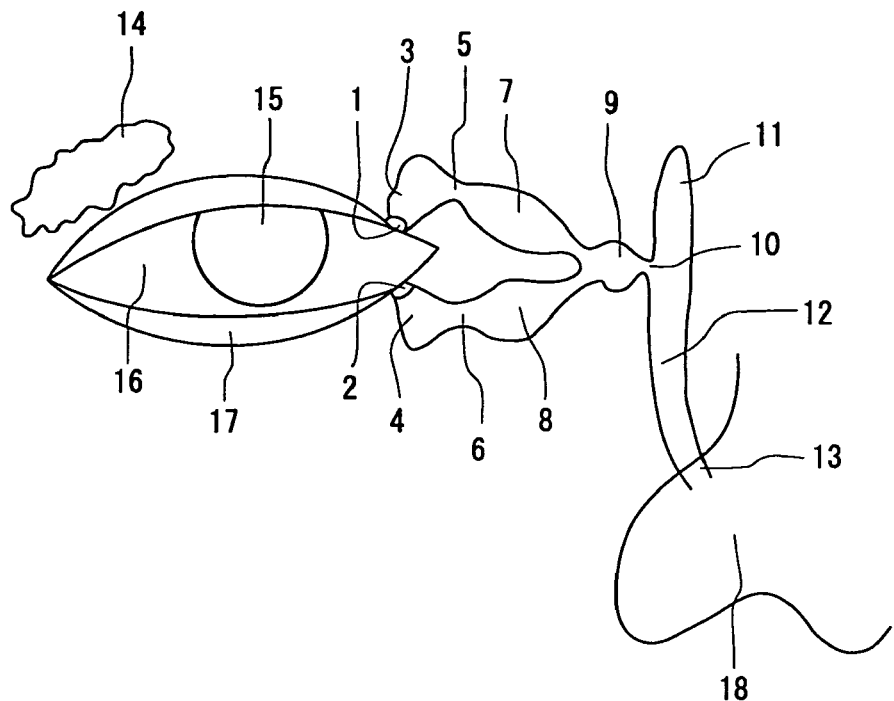
FIG. 1 is a schematic diagram of a lacrimal duct
Figure 2:
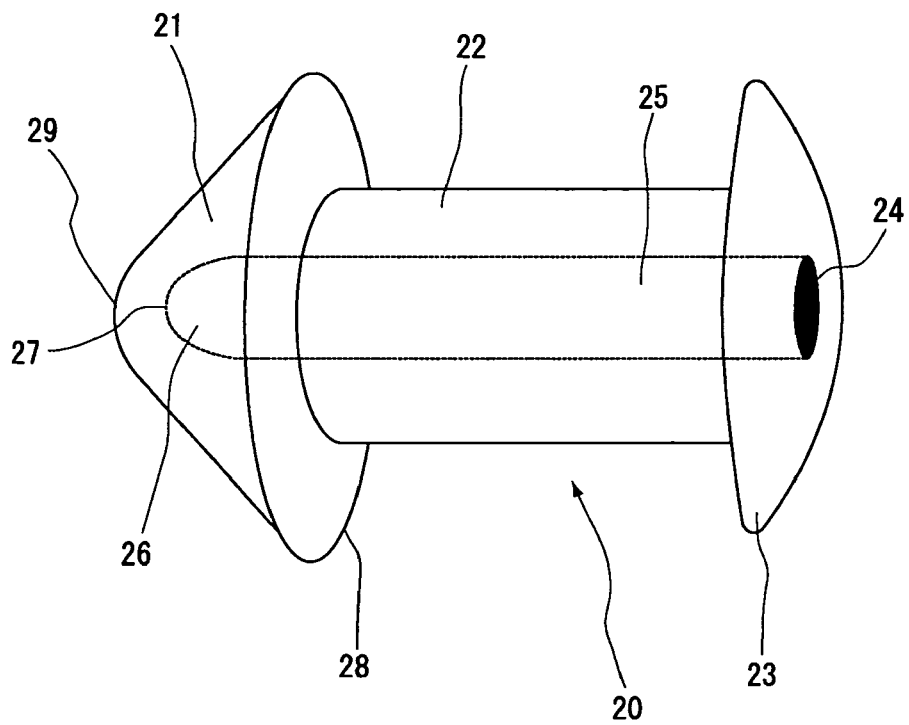
FIG. 2 is a schematic diagram showing a conventional punctal plug.
Figure 3:
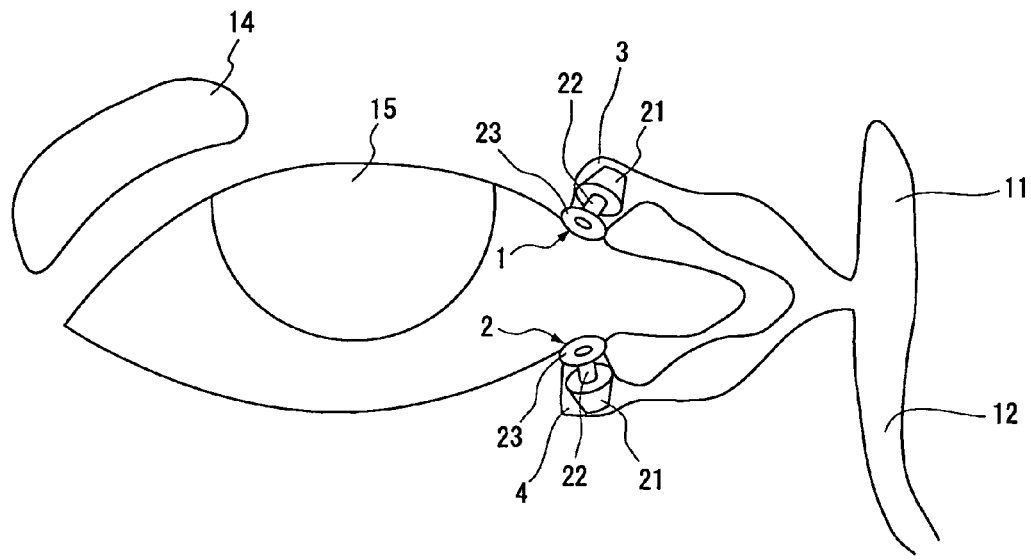
FIG. 3 is a schematic diagram explaining how to use the punctal plug in FIG. 2.
Figure 4:
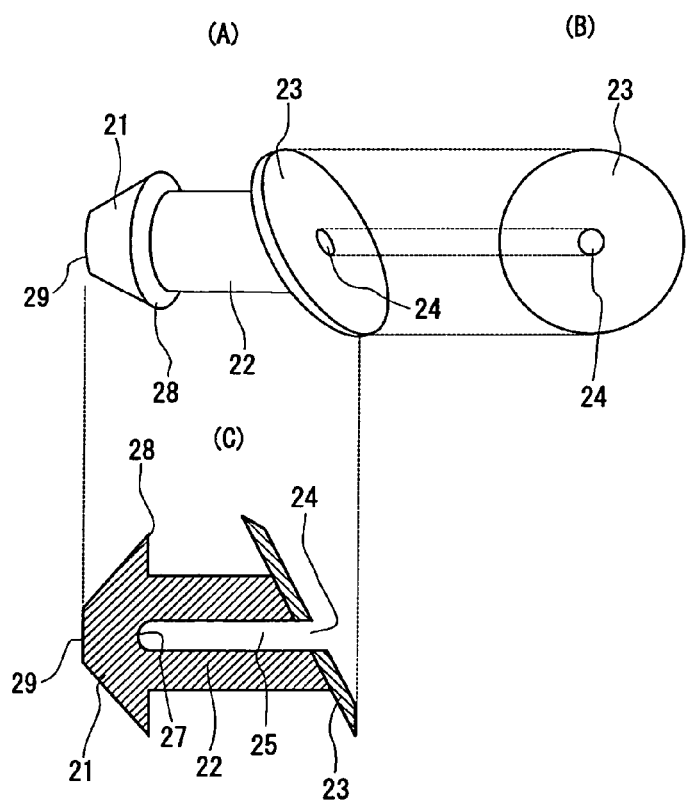
FIG. 4A is a schematic diagram to explain other conventional plug.
FIG. 4B is an end elevational view corresponding to FIG. 4A.
FIG. 4C is a sectional view corresponding to FIG. 4A.
Figure 5:
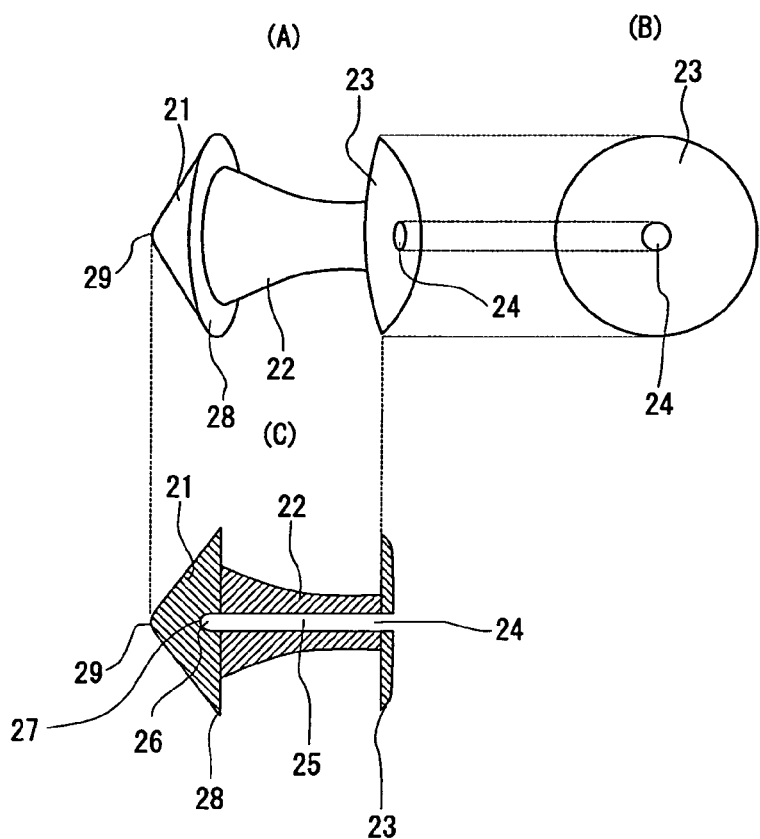
FIG. 5A is a schematic diagram to explain other conventional punctal plugs.
FIG. 5B is an elevational view corresponding to FIG. 5A.
FIG. 5C is a sectional view corresponding to FIG. 5A.
Figure 6:
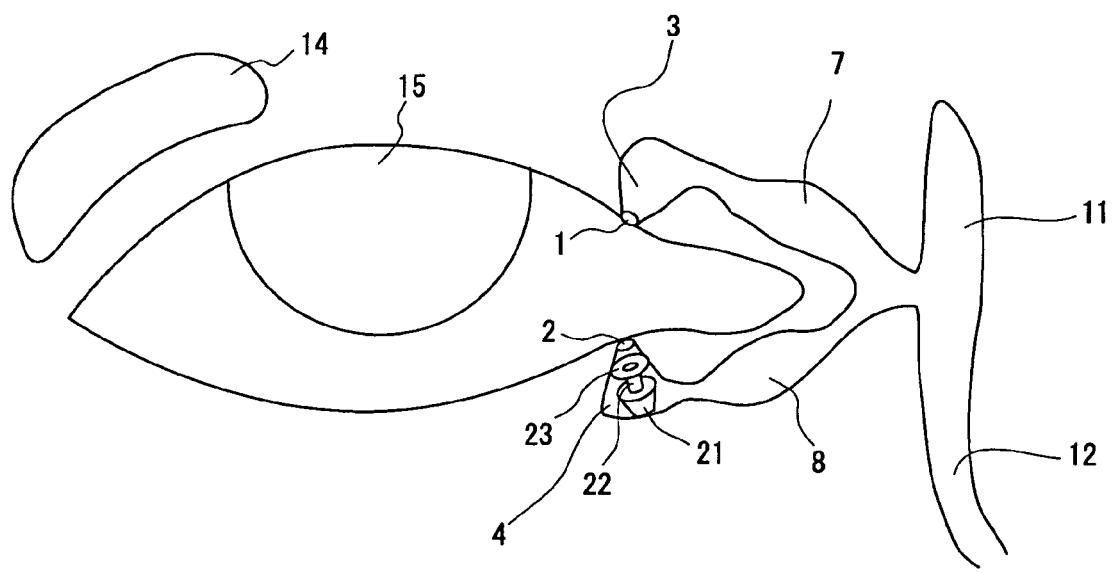
FIG. 6 is an explanatory diagram to show a case of failure in use of the punctal plug in FIG. 2.
Figure 7:
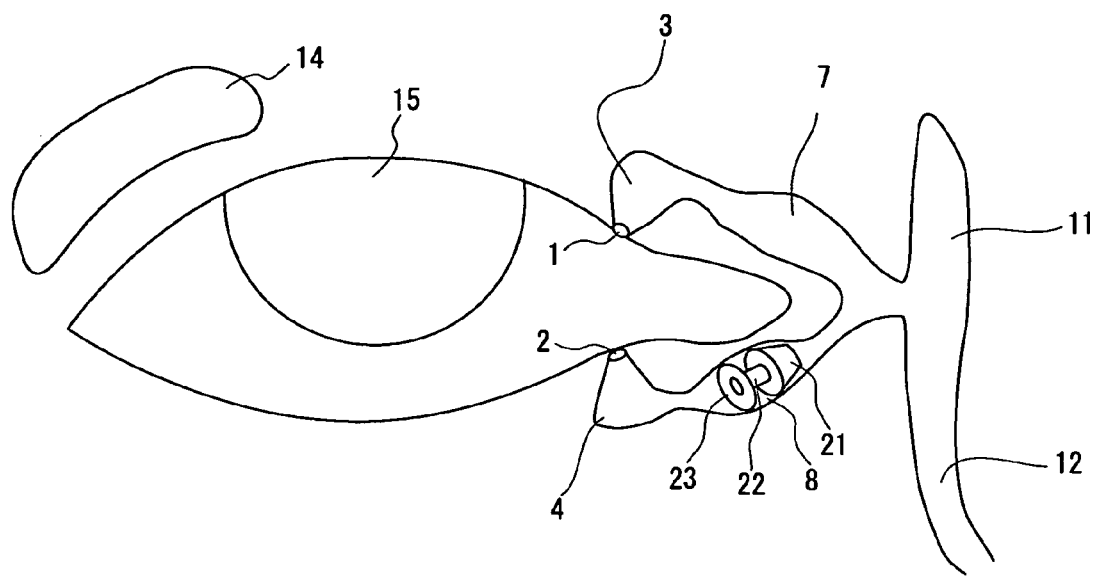
FIG. 7 is an explanatory diagram to show a case of failure in use of the punctal plug in FIG. 2.
Figure 8:
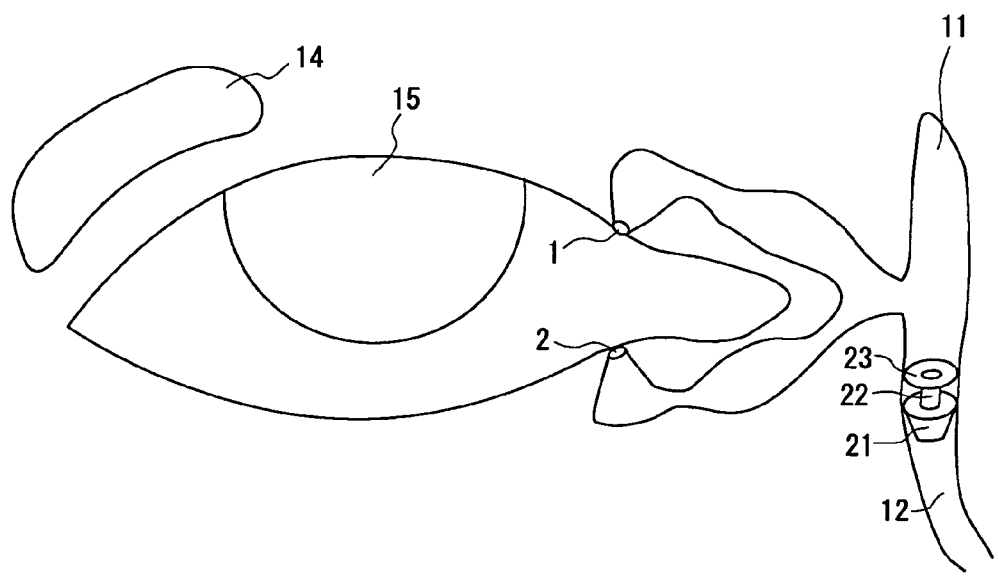
FIG. 8 is an explanatory diagram to show a case of failure in use of the punctal plug in FIG. 2.
Figure 9:
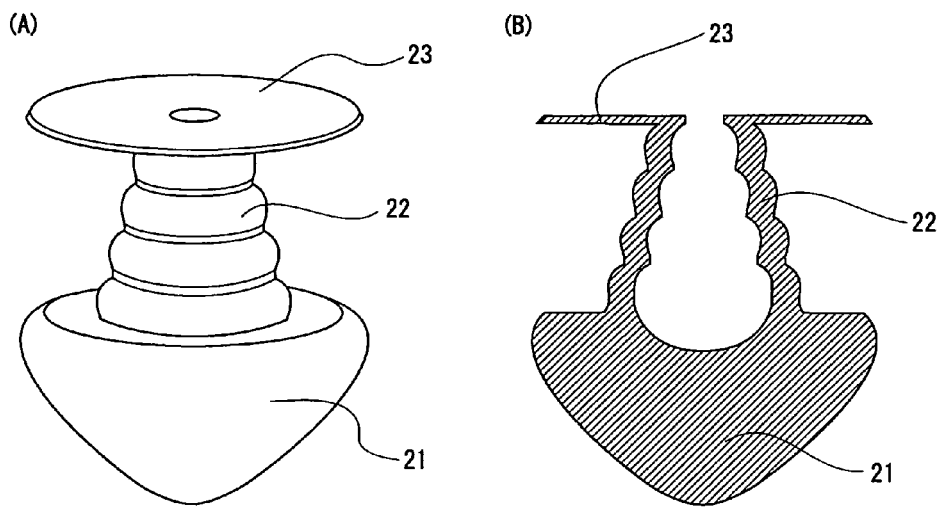
FIG. 9A is a schematic diagram showing a conventional punctal plug having a shaft accordion in shape.
FIG. 9B is a sectional view corresponding to FIG. 9A.
Figure 10:
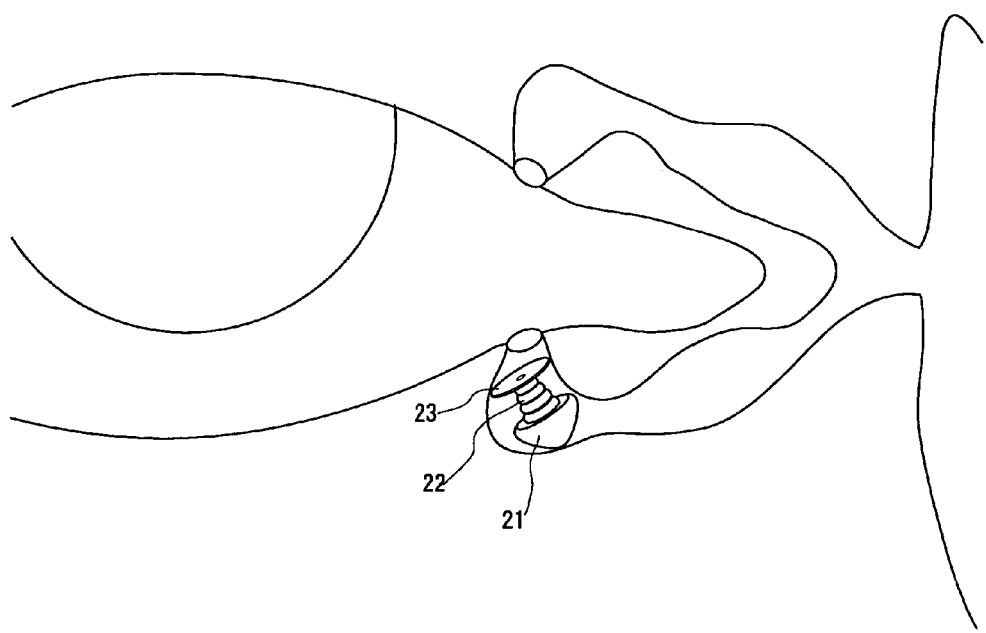
FIG. 10 is an explanatory diagram showing a case of failure in use of the plug in FIG. 9A and FIG. 9B.
Figure 11:
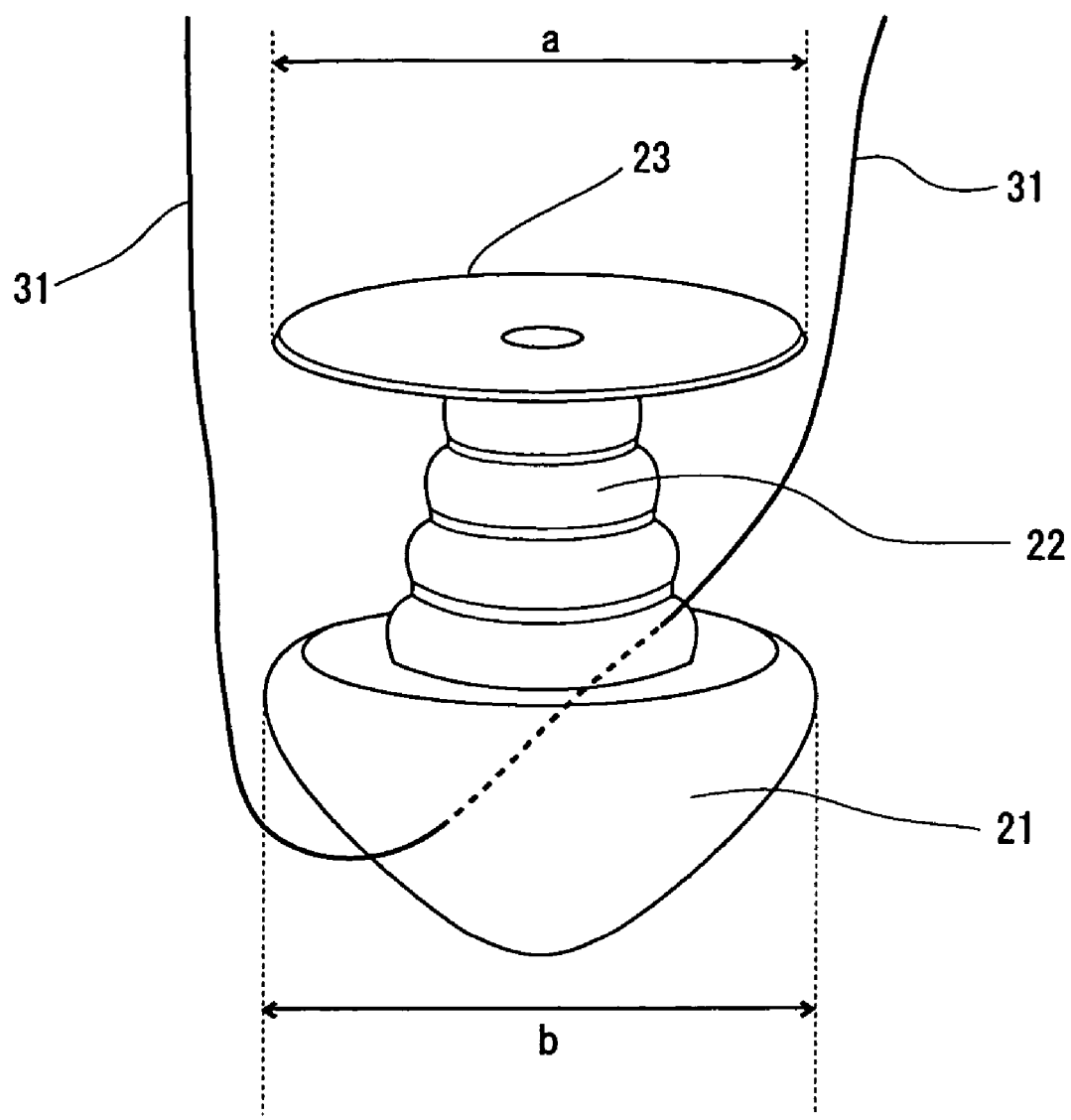
FIG. 11 is a schematic diagram showing a punctal plug according to the present invention.

FIG. 11 shows a punctal plug having a tip portion 21, a shaft 22 and a brim 23 wherein a thread 31 penetrates into the tip portion 21 and the shaft 22.

Figure 12:
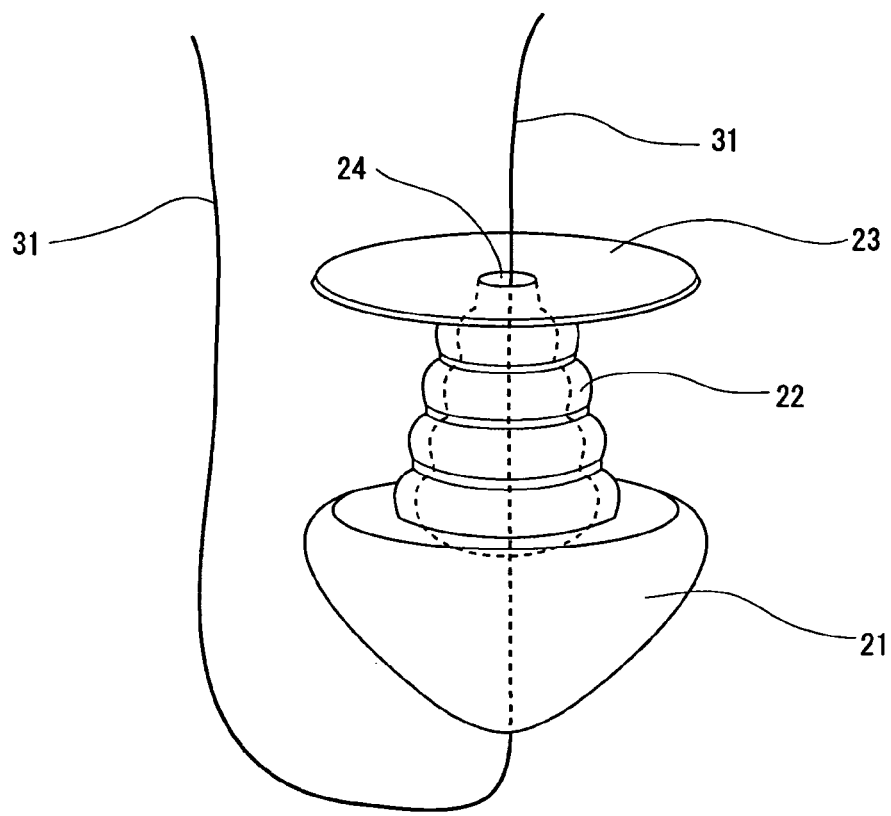
FIG. 12 is a schematic diagram showing a punctal plug according to the present invention.

FIG. 12 shows a punctal plug wherein the thread 31 penetrates into the tip portion 21 via the hole 24 in the center of the brim 23 and inner cavity of the shaft 22.

Figure 13:
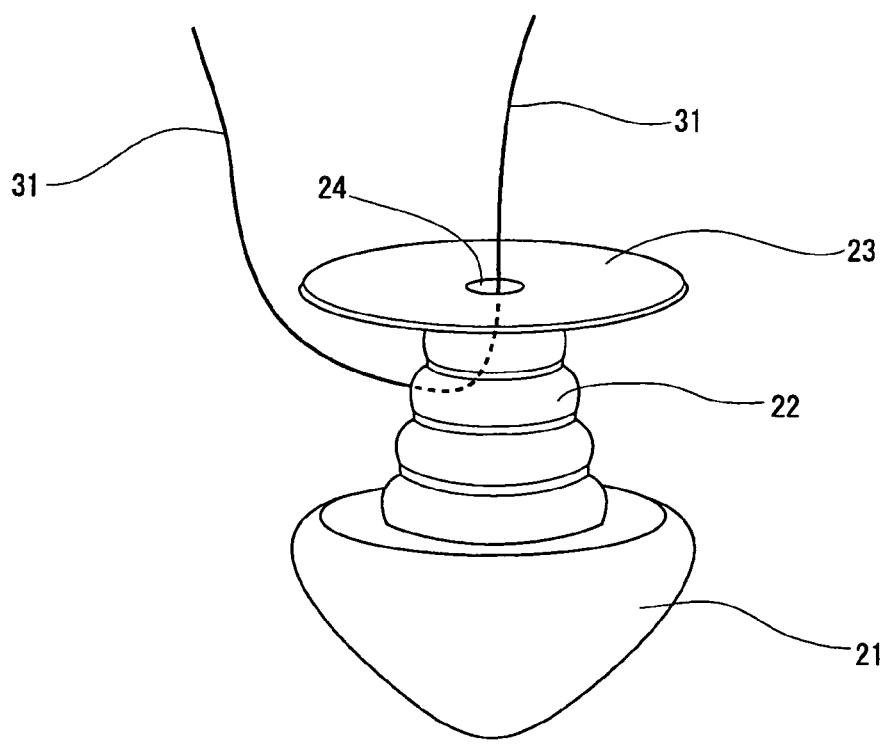
FIG. 13 is a schematic diagram showing a punctal plug according to the present invention.

FIG. 13 shows a punctal plug wherein the thread 31 penetrates into the shaft 22 from the hole 24 of the brim.

Figure 14:
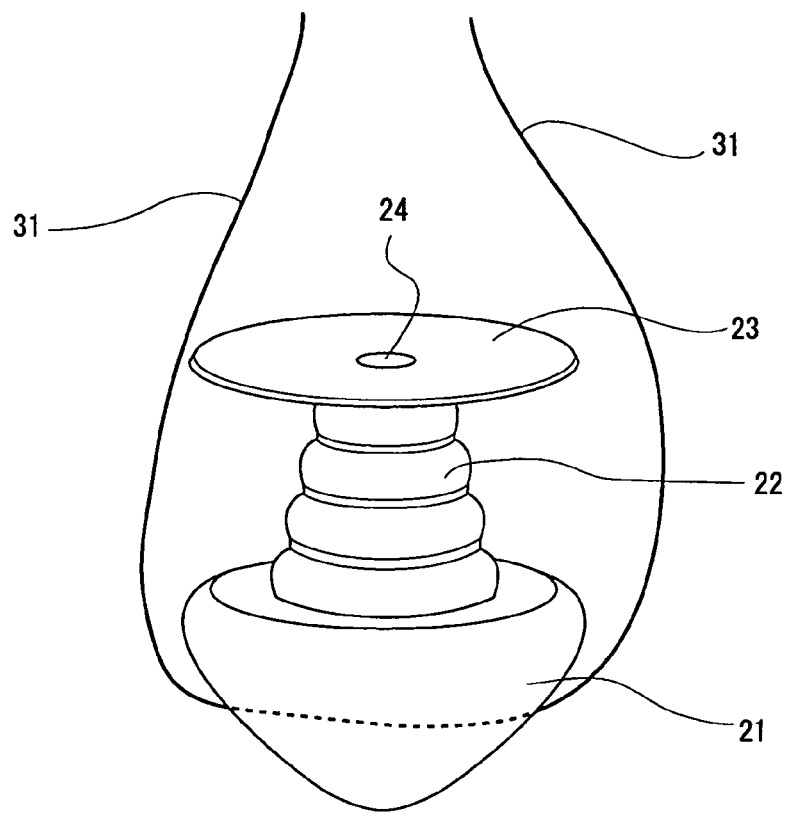
FIG. 14 is a schematic diagram showing a punctal plug according to the present invention.

FIG. 14 shows a punctal plug wherein the thread 31 penetrates into the tip portion 21.

Figure 15:
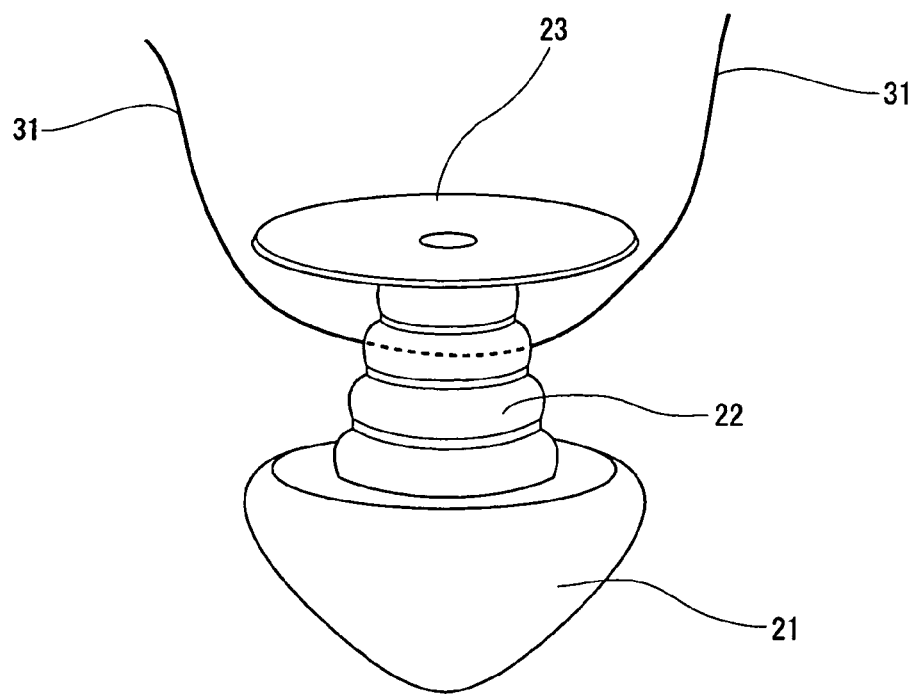
FIG. 15 is a schematic diagram showing a punctal plug according to the present invention.

FIG. 15 shows the thread 31 which penetrates into the shaft 22.

Figure 16:
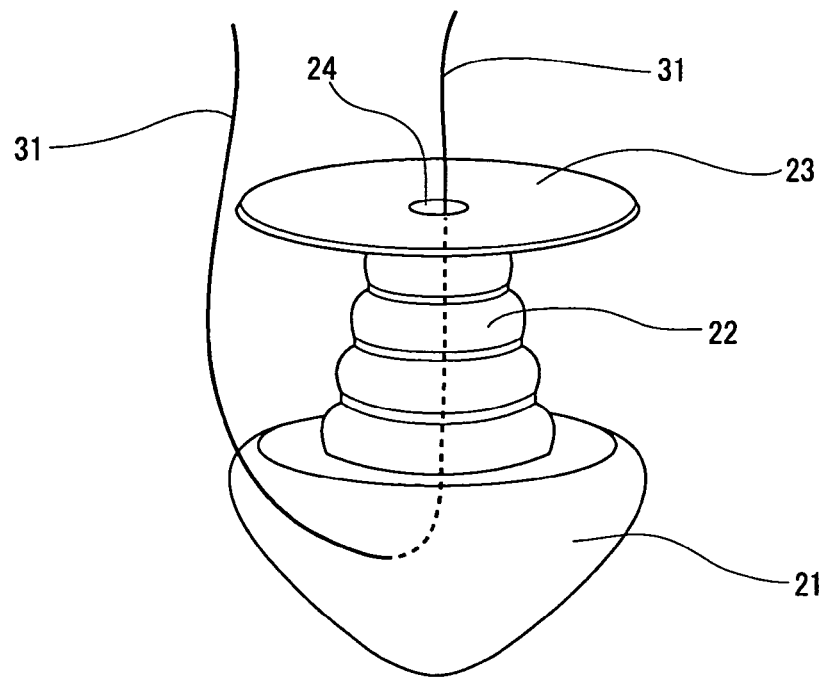
FIG. 16 is a schematic diagram showing a punctal plug according to the present invention.

FIG. 16 shows the thread 31 which penetrates into the tip portion 21 via the hole 24 of the brim 23 and the inner space of the shaft 22.

Figure 17:
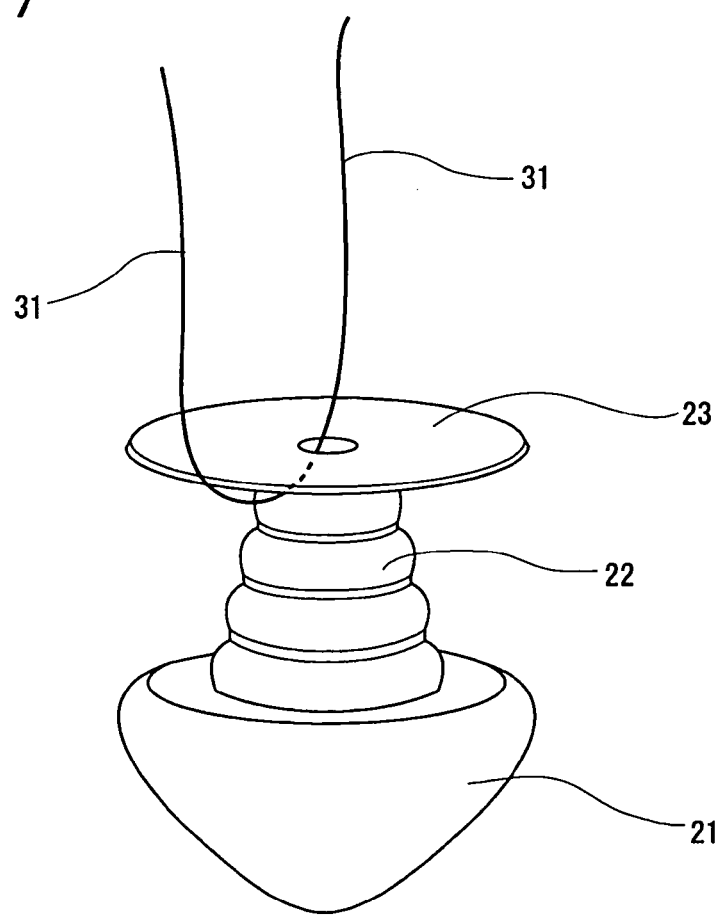
FIG. 17 is a schematic diagram showing a punctal plug according to the present invention.
Figure 18:
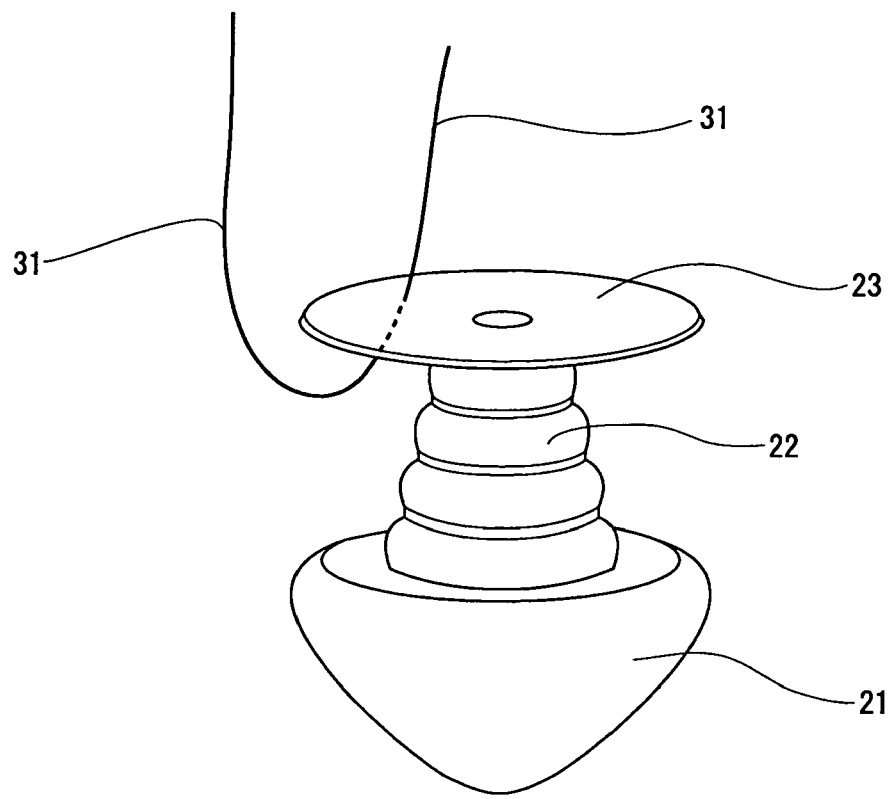
FIG. 18 is a schematic diagram showing a punctal plug according to the present invention.

FIGS. 17 and 18 show the thread 31 which penetrates the brim 23.

Figure 19:
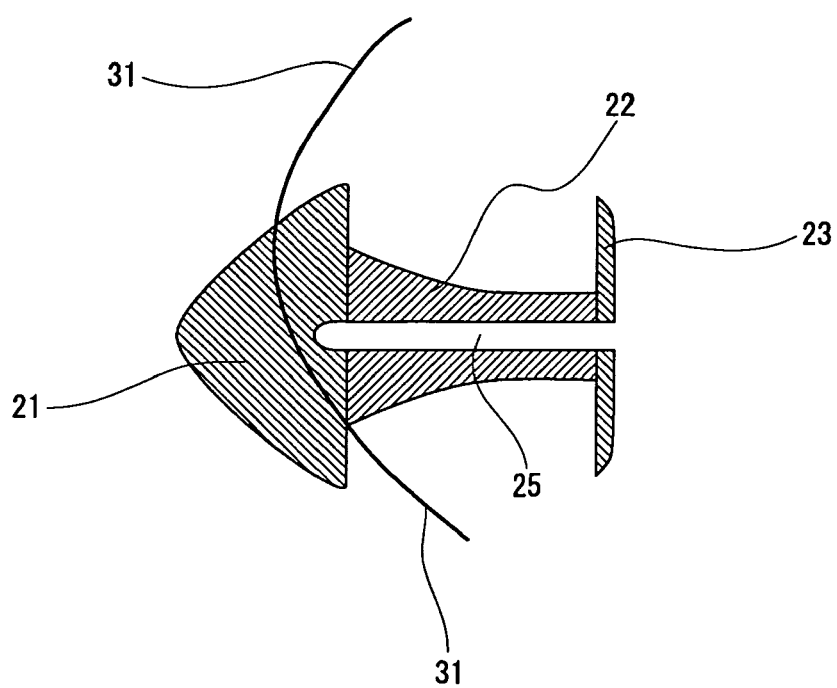
FIG. 19 is a sectional view showing a case according to the present invention.

FIG. 19 shows the thread 31 which penetrates the tip portion 21.

Figure 20:
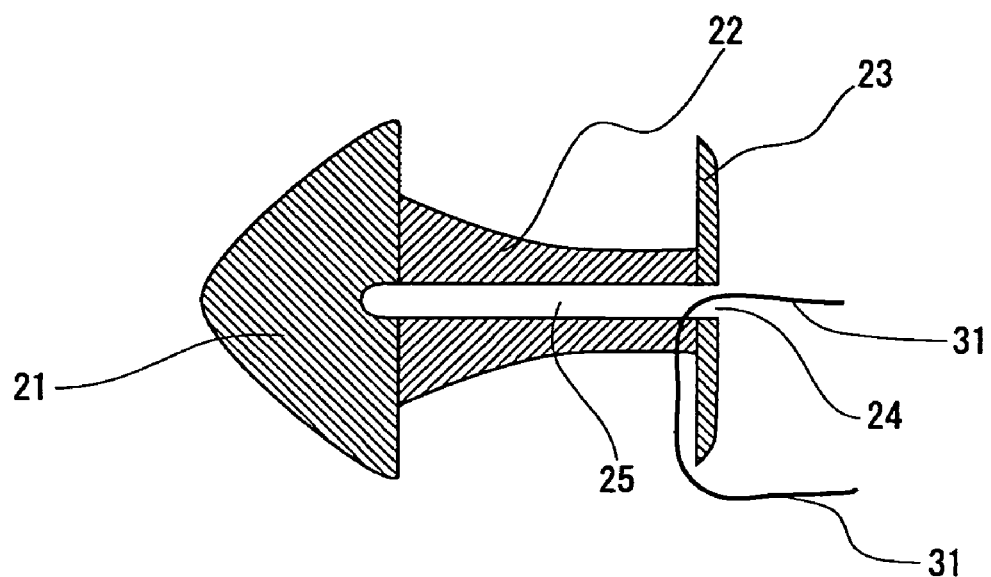
FIG. 20 is a sectional view showing a case according to the present invention.

FIG. 20 shows the thread 31 which penetrates the shaft 22 via the hole 24.

Figure 21:
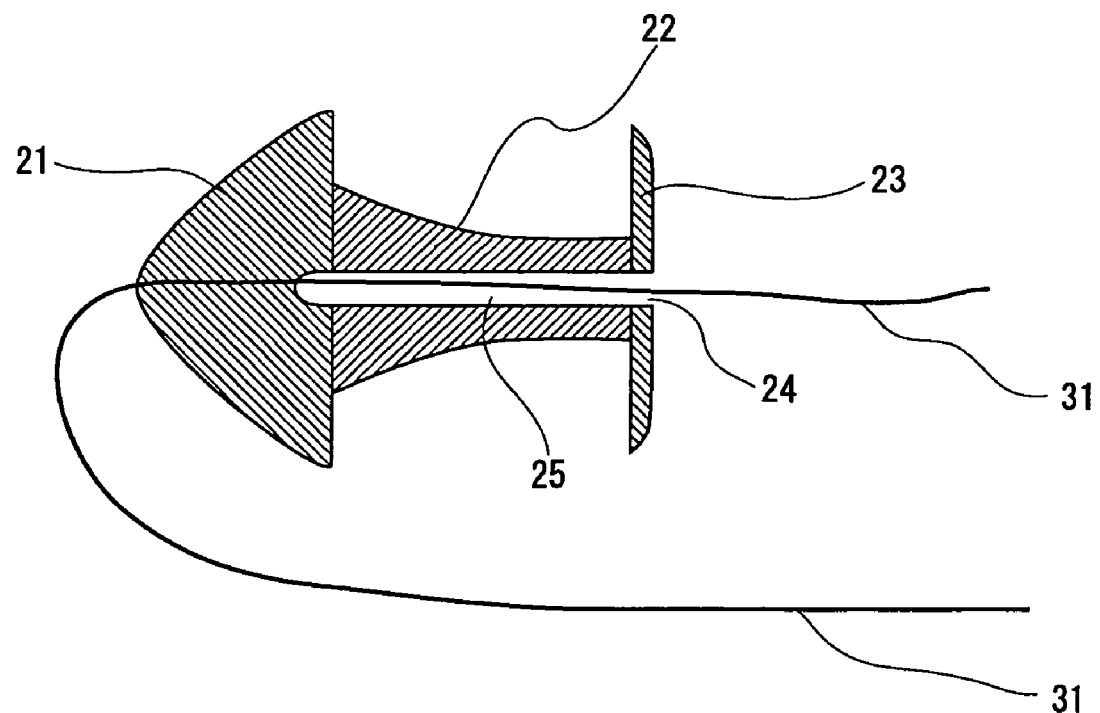
FIG. 21 is a sectional view showing a case according to the present invention.

FIG. 21 shows the thread 31 which penetrates the tip portion 21 via the inner space 25 of the shaft 22.

Figure 22:
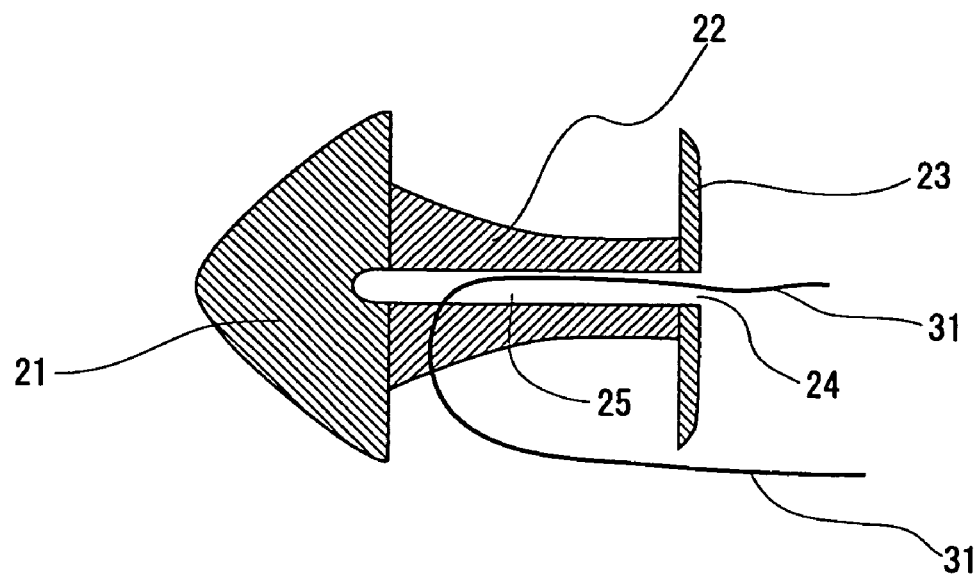
FIG. 22 is a sectional view showing a case according to the present invention.

FIG. 22 shows the thread 31 which penetrates the shaft 22 via the hole 24 and a deep part of the inner cavity 25 of the shaft 22.

Figure 23:
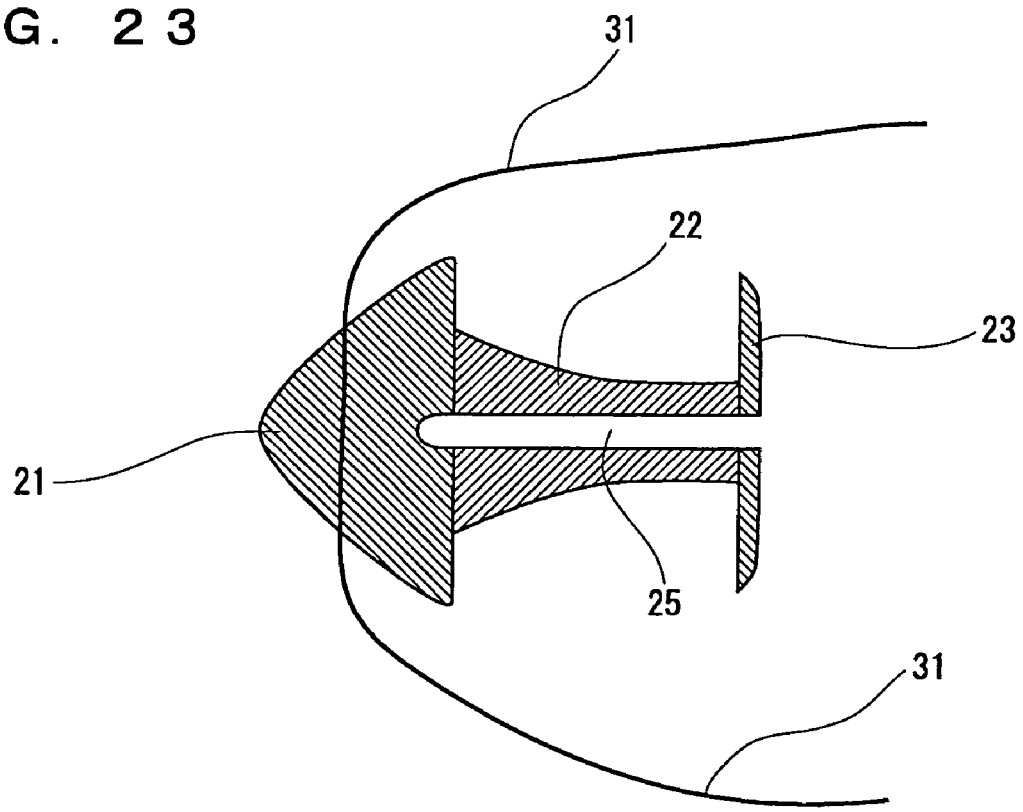
FIG. 23 is a sectional view showing a case according to the present invention.

FIG. 23 shows the thread 31 which penetrates the tip portion 21.

Figure 24:
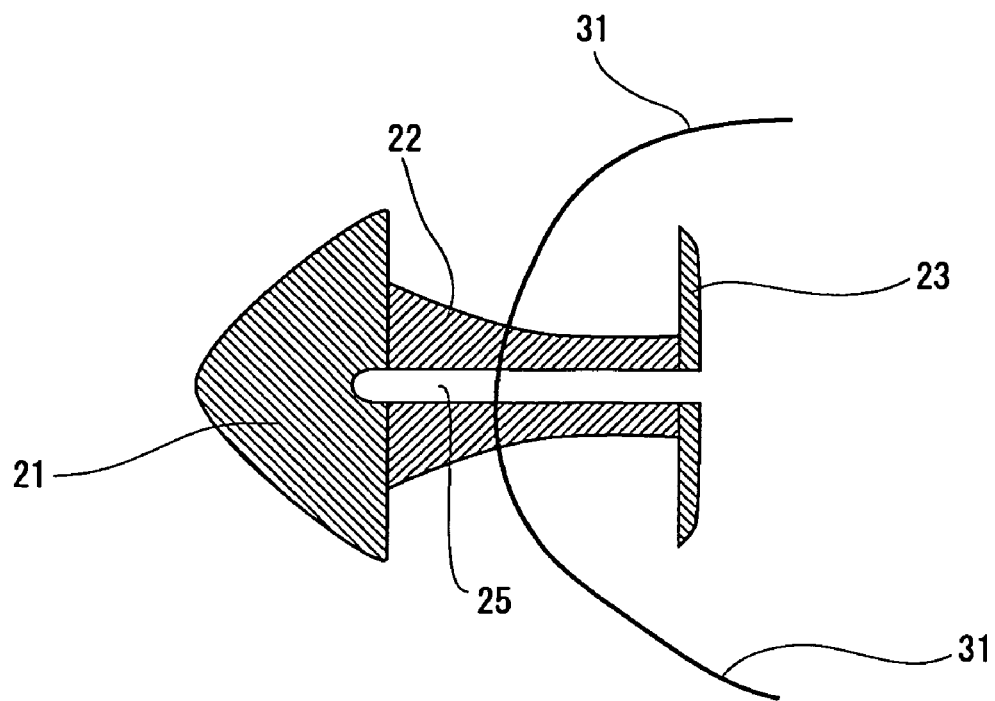
FIG. 24 is a sectional view showing a case according to the present invention.

FIG. 24 shows the thread 31 which penetrates through the shaft 22

Figure 25:
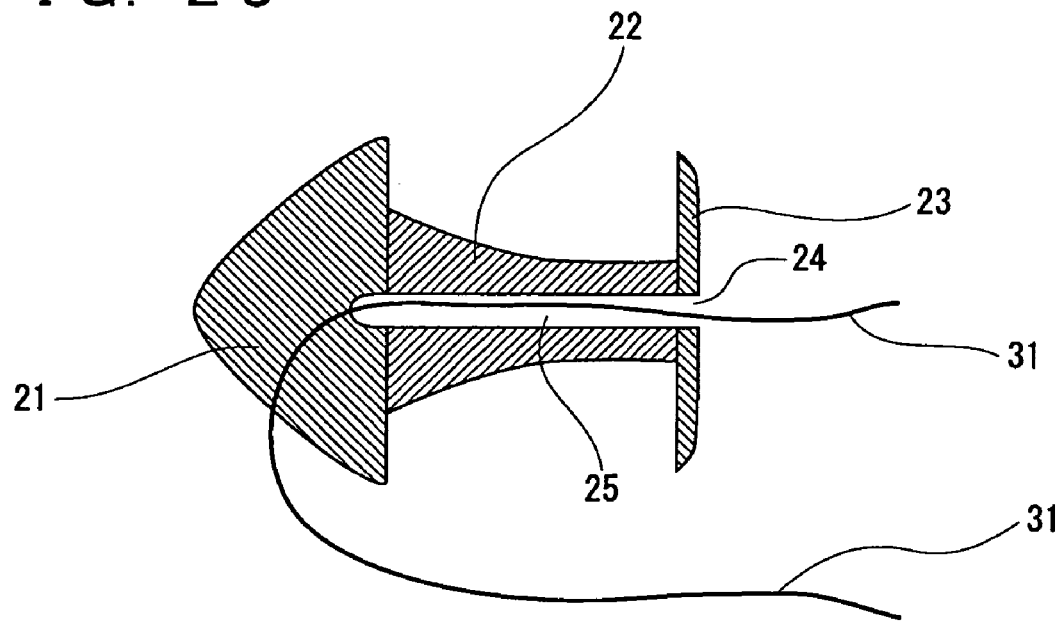
FIG. 25 is a sectional view showing a case according to the present invention.

FIG. 25 shows the thread 31 which penetrates the tip portion 21 via the hole 24 and the lumen of the shaft 22.

Figure 26:
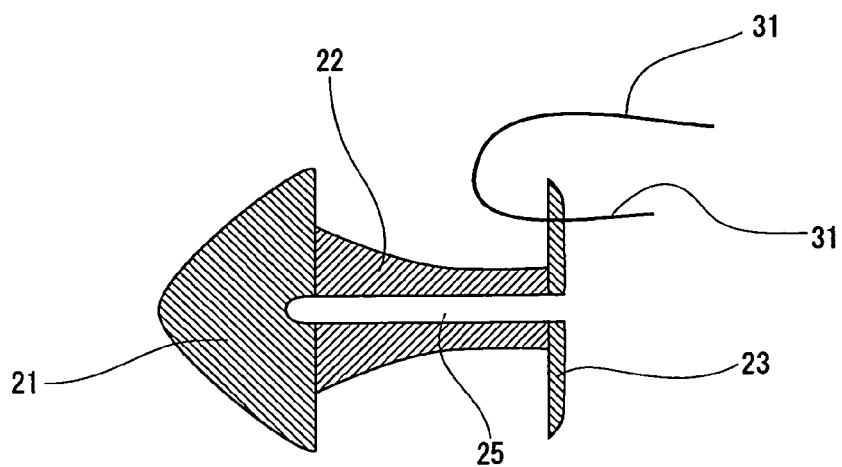
FIG. 26 is a sectional view showing a case according to the present invention.
Figure 27:
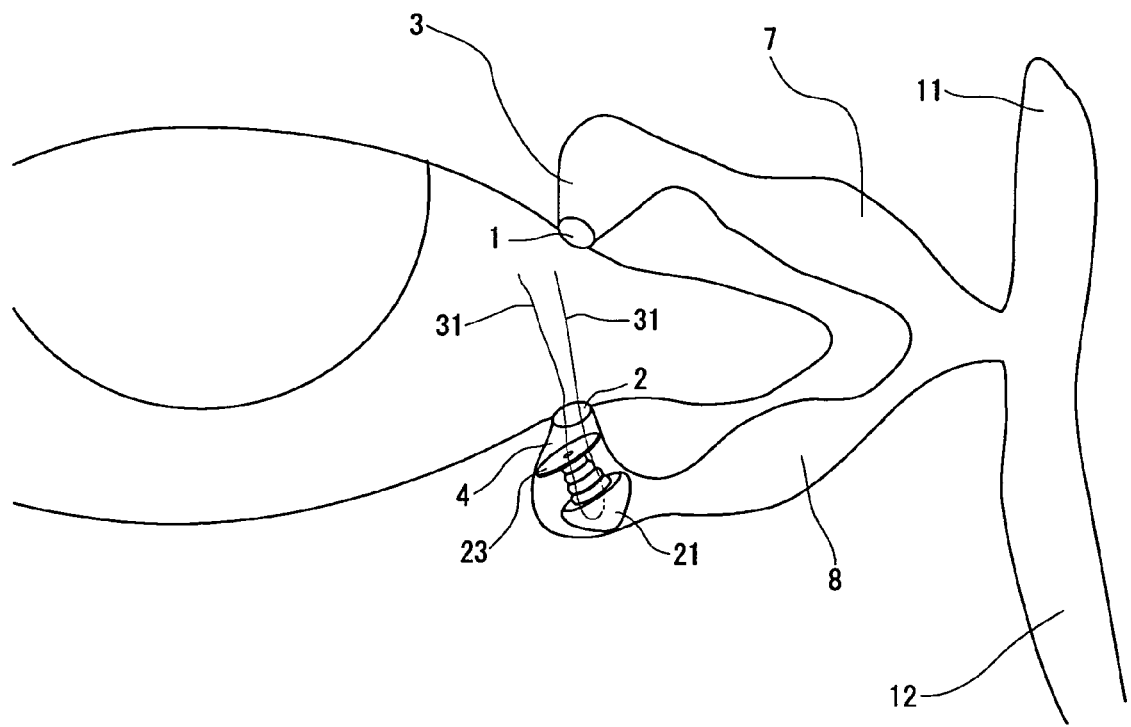
FIG. 27 is an explanatory diagram showing how to insert a punctal plug according to the present invention.
Figure 28:
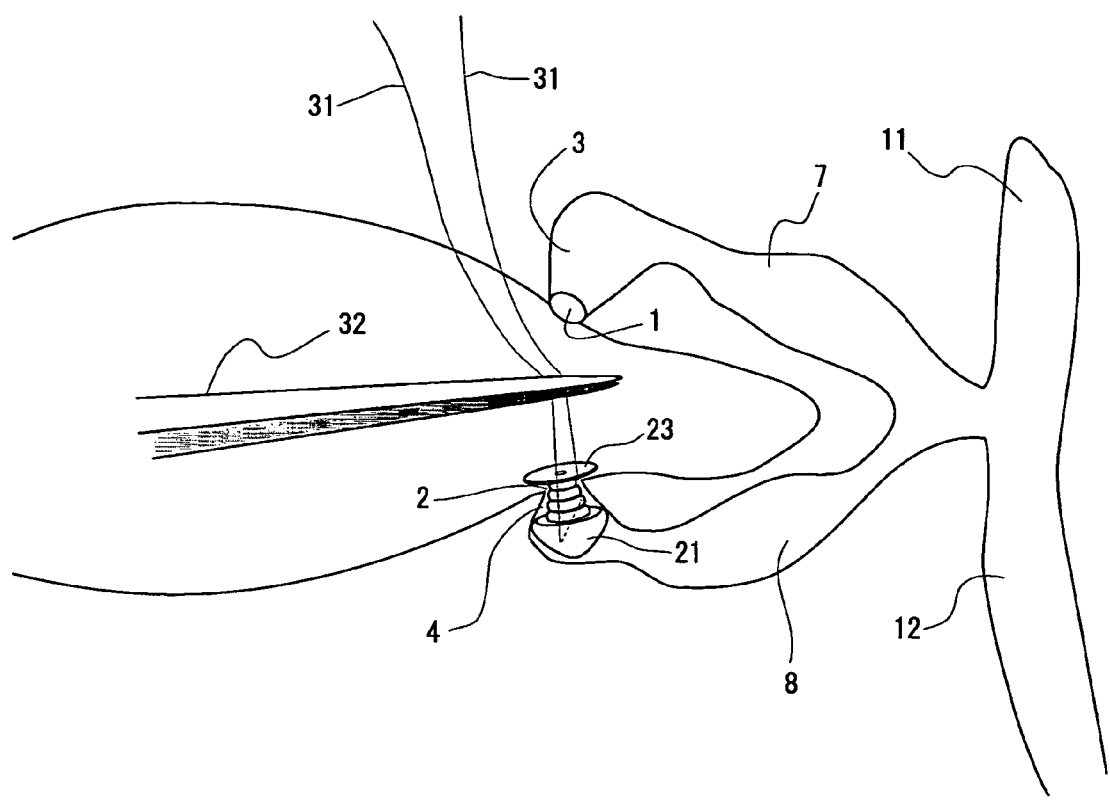
FIG. 28 is an explanatory diagram showing how to insert a punctal plug according to the present invention.

FIG. 26 shows the thread 31 which penetrates the brim 23.

For thread 31 used in FIGS. 11~26, thread 0.02~0.05 mm in diameter, sufficiently thin for the punctal plug and not easily broken is suitable like 9-0 nylon and 10-0 nylon.

The threaded punctal plug is inserted using a metal probe (inserter). If the brim is lodged in the lacrimal duct, because of over insertion, both sides of the thread 31 are pulled simultaneously to pull the brim out of the punctum for correct placement of the punctal plug.

Figure 29:
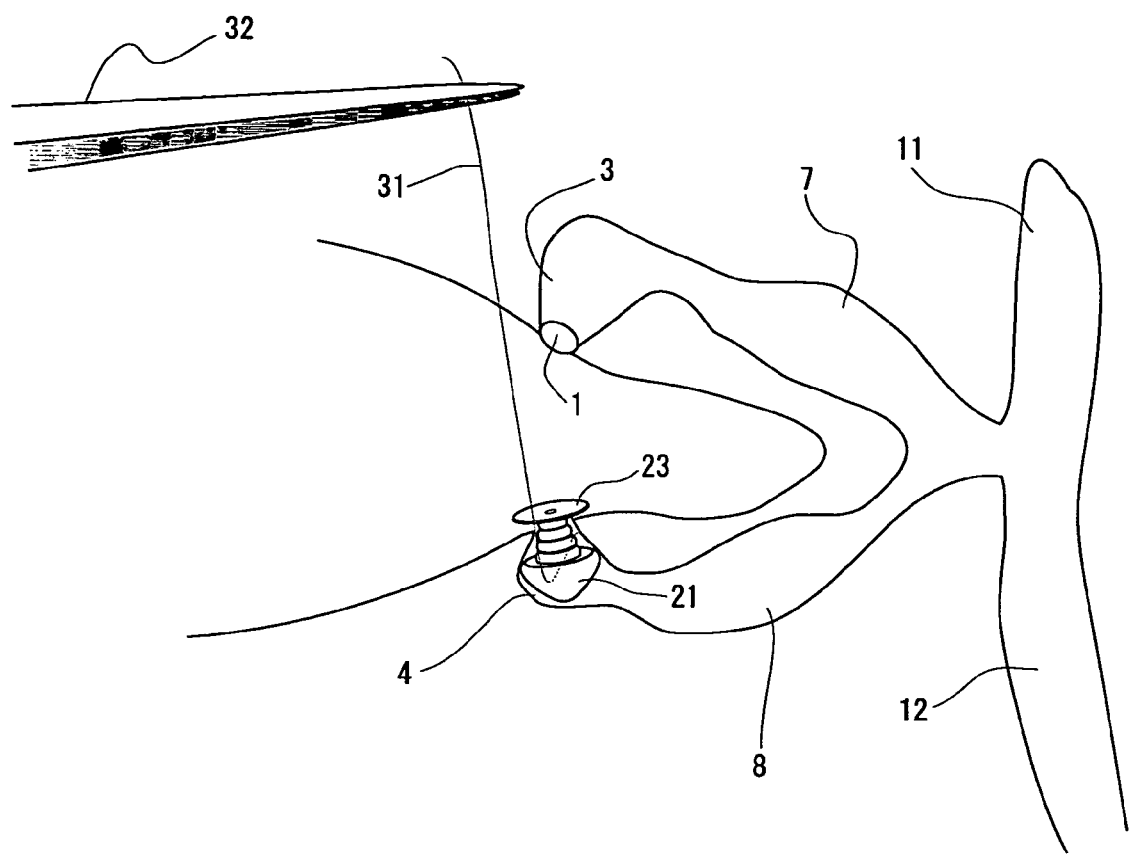
FIG. 29 is an explanatory diagram showing how to insert a punctal plug according to the present invention.
Figure 30:
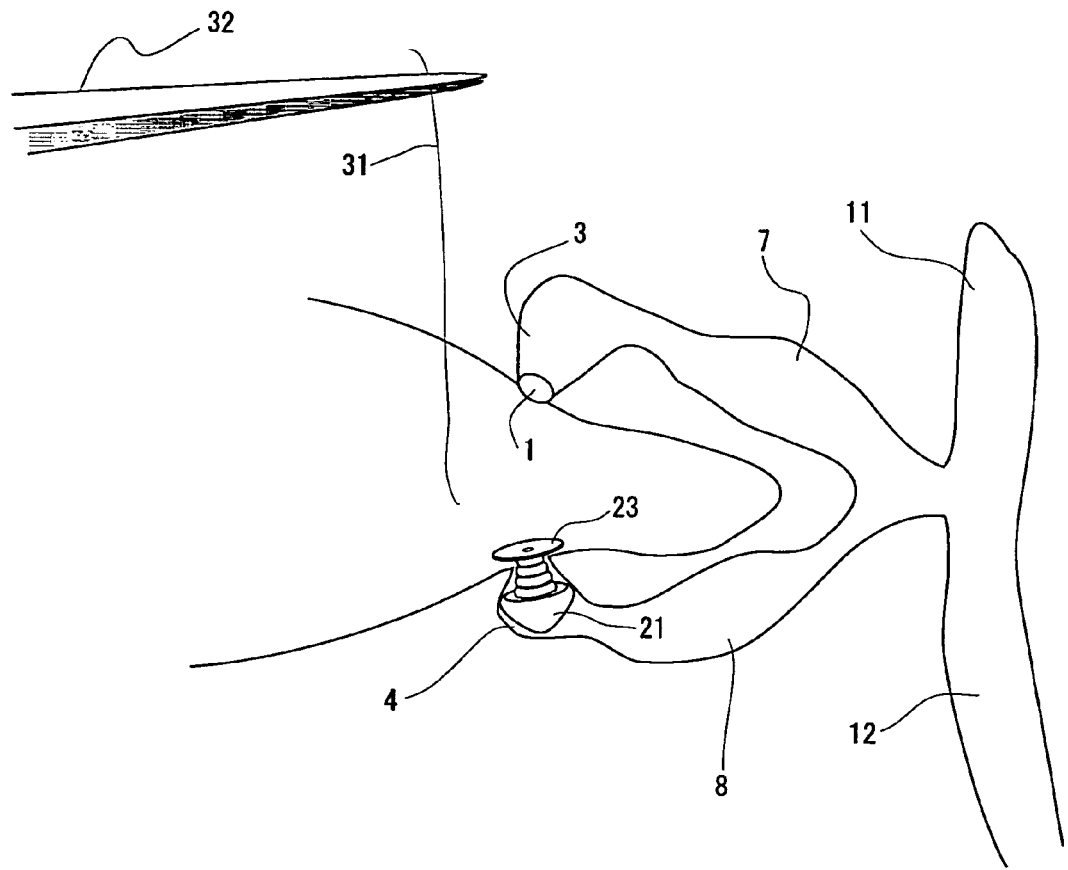
FIG. 30 is an explanatory diagram showing how to insert a punctal plug according to the present invention.

As shown in FIGS. 29 and 30, after pulling the brim 23 of the punctal plug out of the punctum, one side of the thread is pulled to remove the thread 31 from the punctal plug. As shown in FIGS. 11~28, the threaded punctal plug with an accordion shaped shaft also can be inserted safely by the thread 31 because the brim included in the lacrimal duct can be pulled out of the punctum using the thread 31.

Thus, the method using the thread 31 can be applied for any type of punctal plug with a brim.

The suitable brim size is different from person to person, and a threaded punctal plug with a minimally sized brim can be chosen because the plug can be inserted correctly and safely, resulting in the unnecessity of making the brim bigger.

Figure 31:
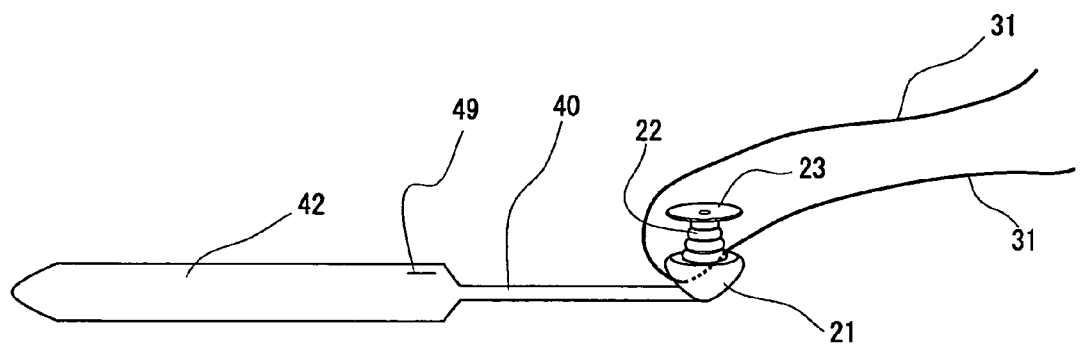
FIG. 31 is a schematic diagram showing other apparatus for intubation with thread according to the present invention.
Figure 32:
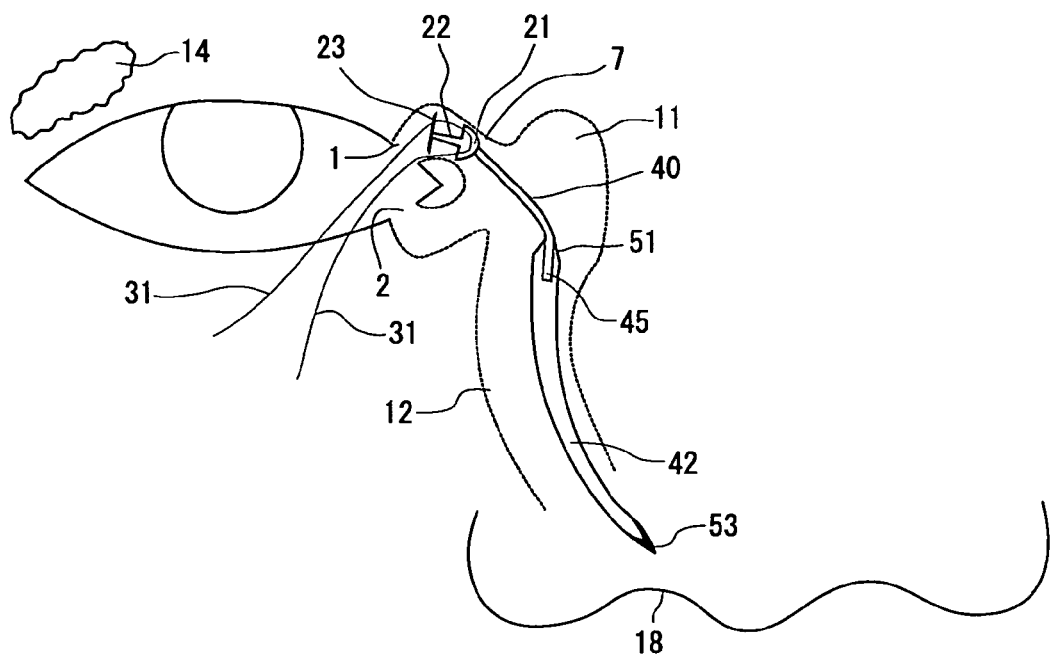
FIG. 32 is a schematic diagram showing how to use other apparatus for intubation with thread according to the present invention.
Figure 33:
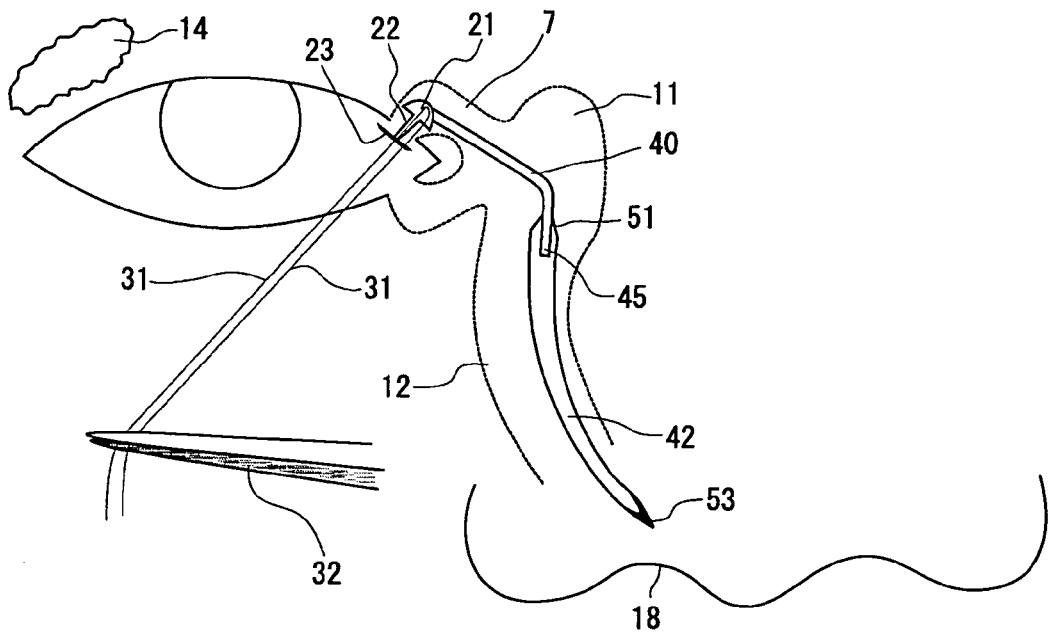
FIG. 33 is a schematic diagram showing how to use other apparatus for intubation with thread according to the present invention.

FIGS. 31~33 show other apparatus for intubation of lacrimal duct having a thin tube with a sufficient length to cover from punctum to lacrimal sac, punctal plug attached to one end of said thin tube, and a thick tube attached to the other end of said thin tube, wherein the tip portion 21 of the punctal plug is penetrated by the thread 31 which can be allowed to penetrate the thinner tube 40 or thicker tube 42.

Figure 34:
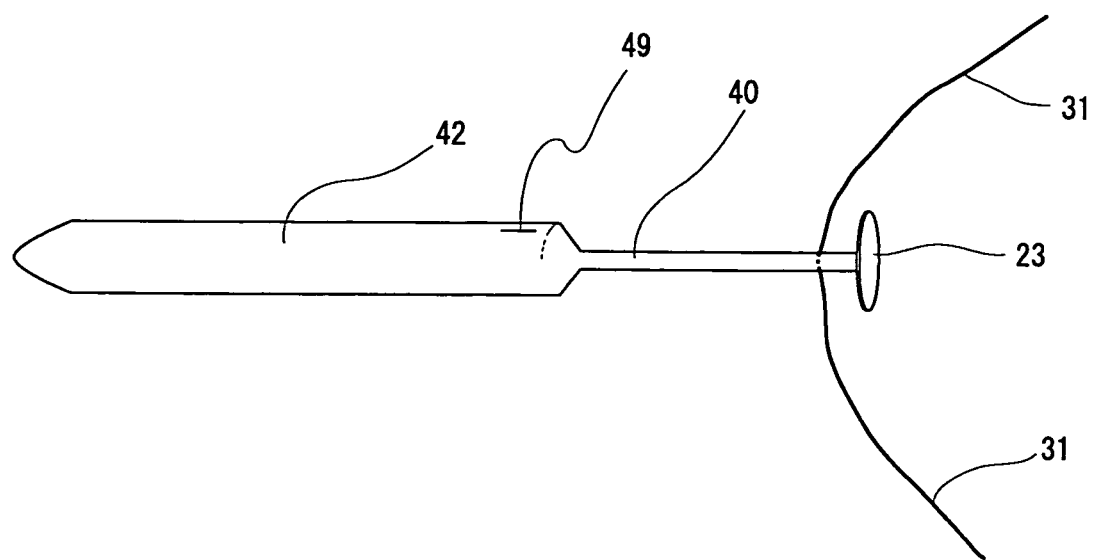
FIG. 34 is a schematic diagram showing other apparatus for intubation with thread according to the present invention.
Figure 35:
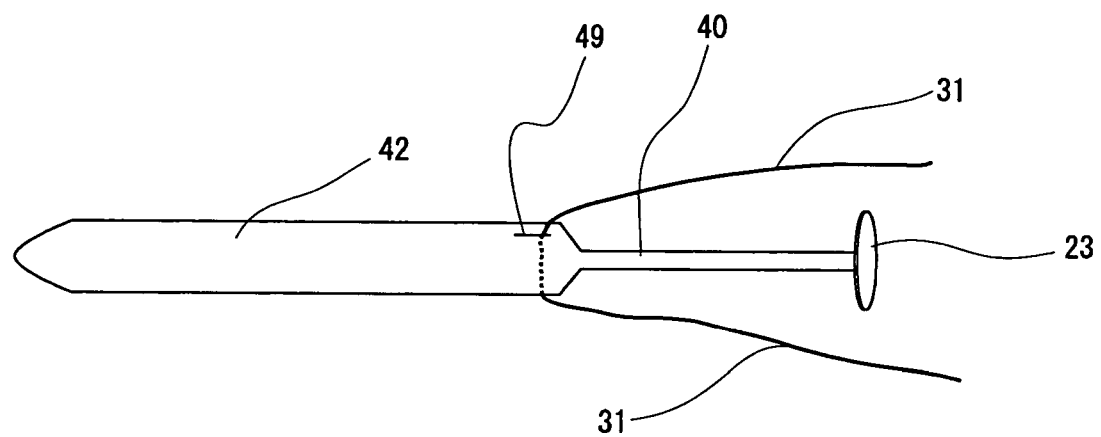
FIG. 35 is a schematic diagram showing other apparatus for intubation with thread according to the present invention.

FIGS. 34~37 show still other apparatus for intubation of lacrimal duct having a thin tube with a sufficient length to cover from the punctum to the lacrimal sac, the brim 23 attached to one end of said thin tube, and the thick tube attached to the other end of said thin tube, and in FIG. 34, the thin tube is penetrated by thread. In FIG. 35, the thick tube is penetrated by thread 31.

Apparatus for intubation of lacrimal duct shown in FIGS. 31~37, are pushed into the lacrimal duct using a metal probe which is inserted into a thick tube from a small cut applied to said thick tube.

FIG. 32 shows the state wherein the brim 23 of the apparatus for intubation of the lacrimal duct shown in FIG. 31 is lodged in the lacrimal duct from the upper punctum 1, and as shown in FIG. 33 the brim 23 can be pulled out of the punctum by pulling both sides of the thread 31 using forceps because the tip portion 21 of the punctal plug is penetrated by the thread 31.

Figure 36:
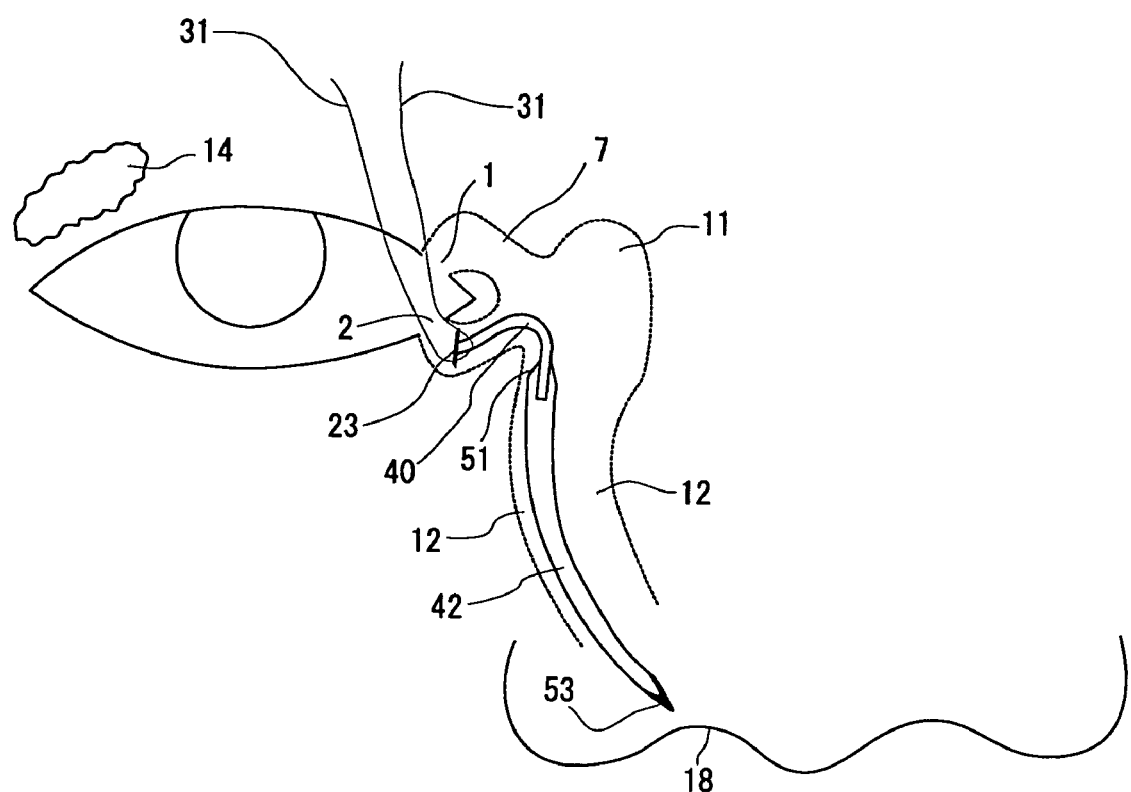
FIG. 36 is a schematic diagram showing how to use other apparatus for intubation with thread according to the present invention.
Figure 37:
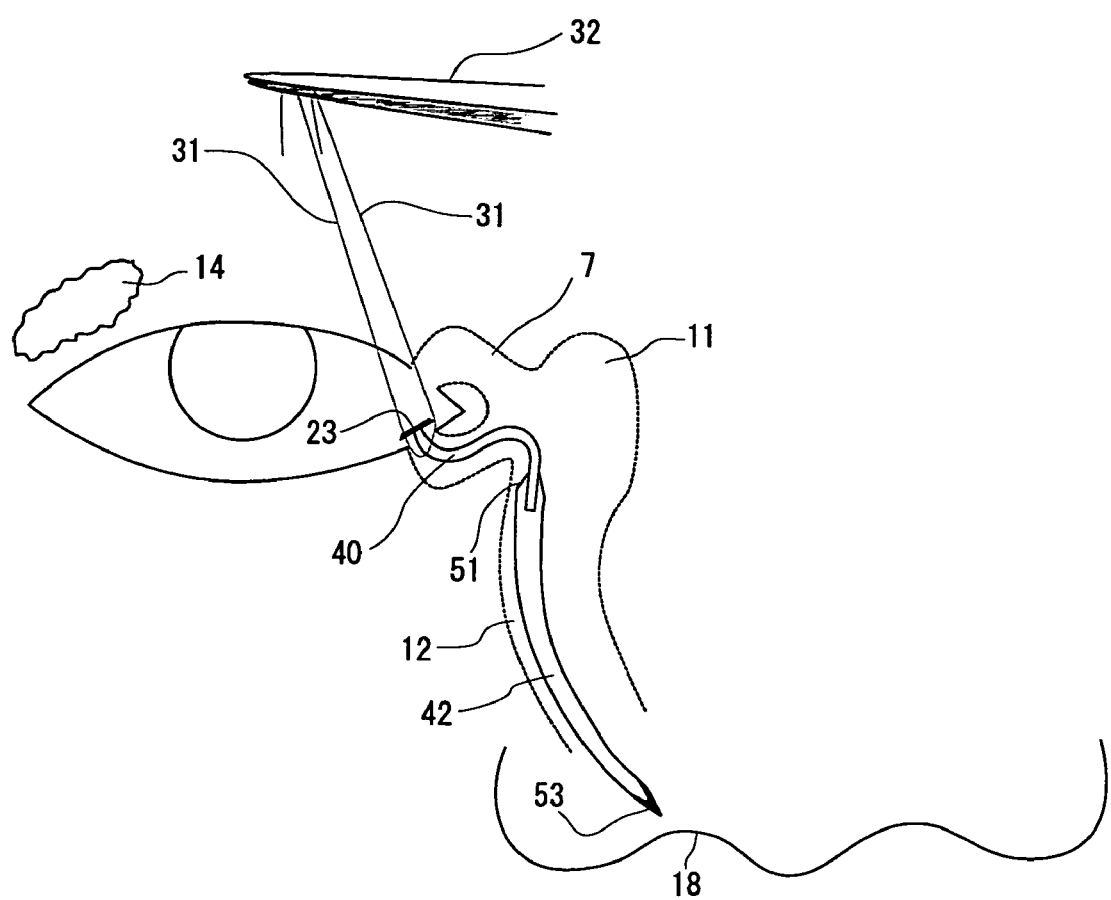
FIG. 37 is a schematic diagram showing how to use other apparatus for intubation with thread according to the present invention.
Figure 38:
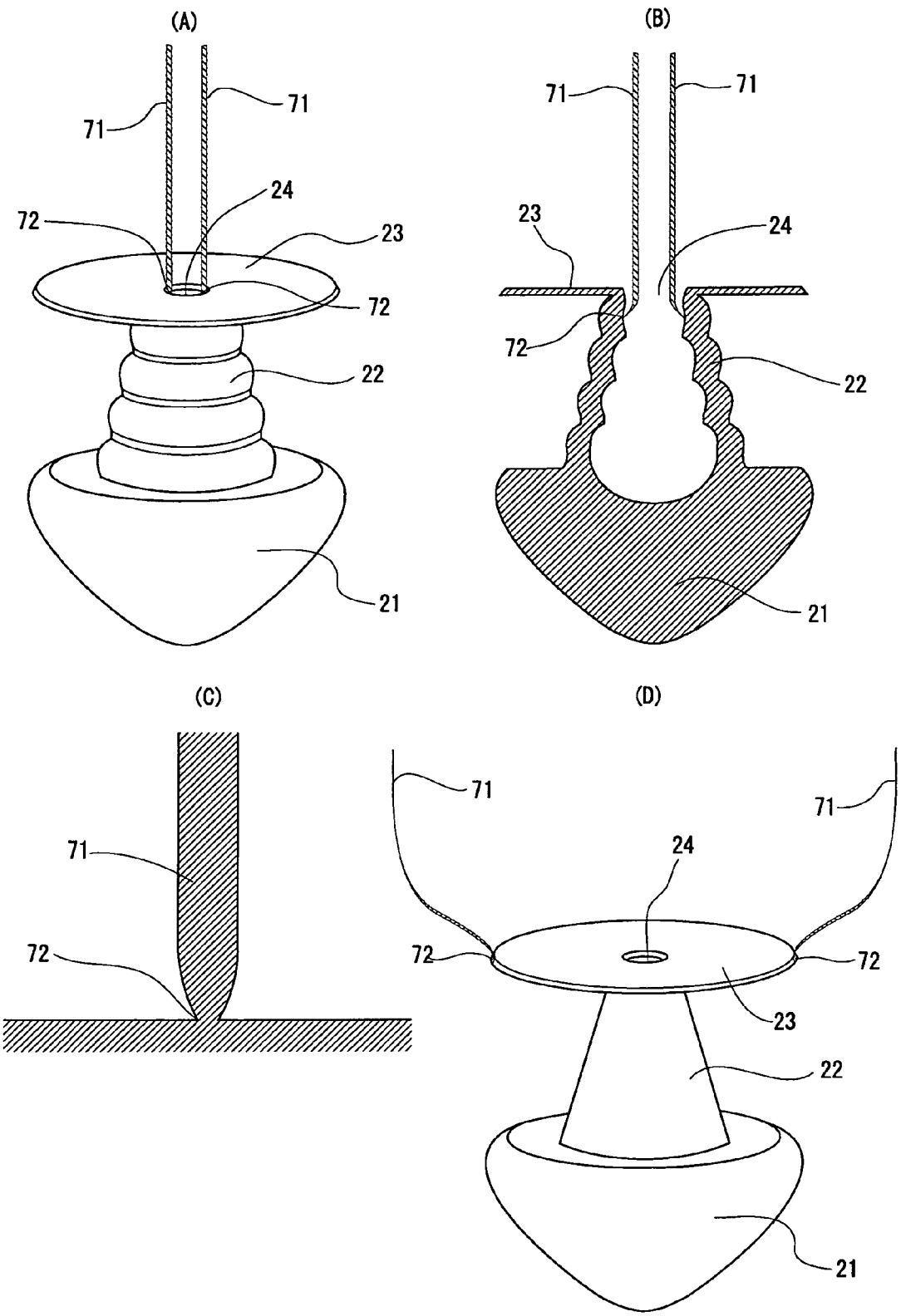
FIG. 38A is a schematic diagram showing a punctal plug according to the present invention.
FIG. 38B is a sectional view corresponding to FIG. 38A.
FIG. 38C is a schematic diagram showing a thread and a fixed point in FIG. 38A.
FIG. 38D is a schematic diagram showing a punctal plug with a fixed point of thread at the edge of the brim.

FIG. 36 shows the state wherein the brim 23 of the apparatus for intubation of the lacrimal duct shown in FIG. 34 is lodged in the lacrimal duct from the lower punctum, and as shown in FIG. 37, the brim can be pulled out of the punctum by pulling both sides of the thread 31 because the thin tube is penetrated by the thread 31.

In a apparatus for intubation of the lacrimal duct shown in FIG. 34 as well as a apparatus for intubation of the lacrimal duct shown in FIG. 31, the brim 23 lodged inside the lacrimal duct as shown in FIG. 36 the brim can be pulled out of the punctum by pulling both sides of the thread 31 simultaneously, as shown in FIG. 37.

Apparatus for intubation of lacrimal duct shown in FIG. 31~37 are applicable to any type of apparatus for intubation having a brim, a thin tube and a thick tube. The technique for punctal plug using the thread is applicable not only to the punctal plugs until now, but also any punctal plug which will be improved and appear in the future. Once the brim lodged inside the lacrimal duct during insertion is pulled out, the brim is not included in the lacrimal duct later. However, in an apparatus for intubation of the lacrimal duct having a thick tube, a thin tube and a brim, the brim outside may go into the lacrimal duct if the brim is too small, so a bigger brim is required compared to a brim of a punctal plug. But in the threaded apparatus for intubation of the lacrimal duct mostly a smaller brim is allowed to be adopted compared to a brim of a conventional apparatus for intubation of lacrimal duct. If the opening of the punctum is too large, a threaded apparatus for intubation for the lacrimal duct having a small brim may be used after making the opening of the punctum smaller by surgery.

Next, other embodiments will be explained by referring to FIG. 38~58.

FIG. 38(A), (B) shows a punctal plug wherein the thread 71 is fixed at the lumen of the shaft 22 from the hole 24 of the brim 23. FIG. 38(C) shows the thread 71 and the fixed point 72.

FIG. 38(D) shows the thread 71 fixed at the edge of the brim 23.

Figure 39:
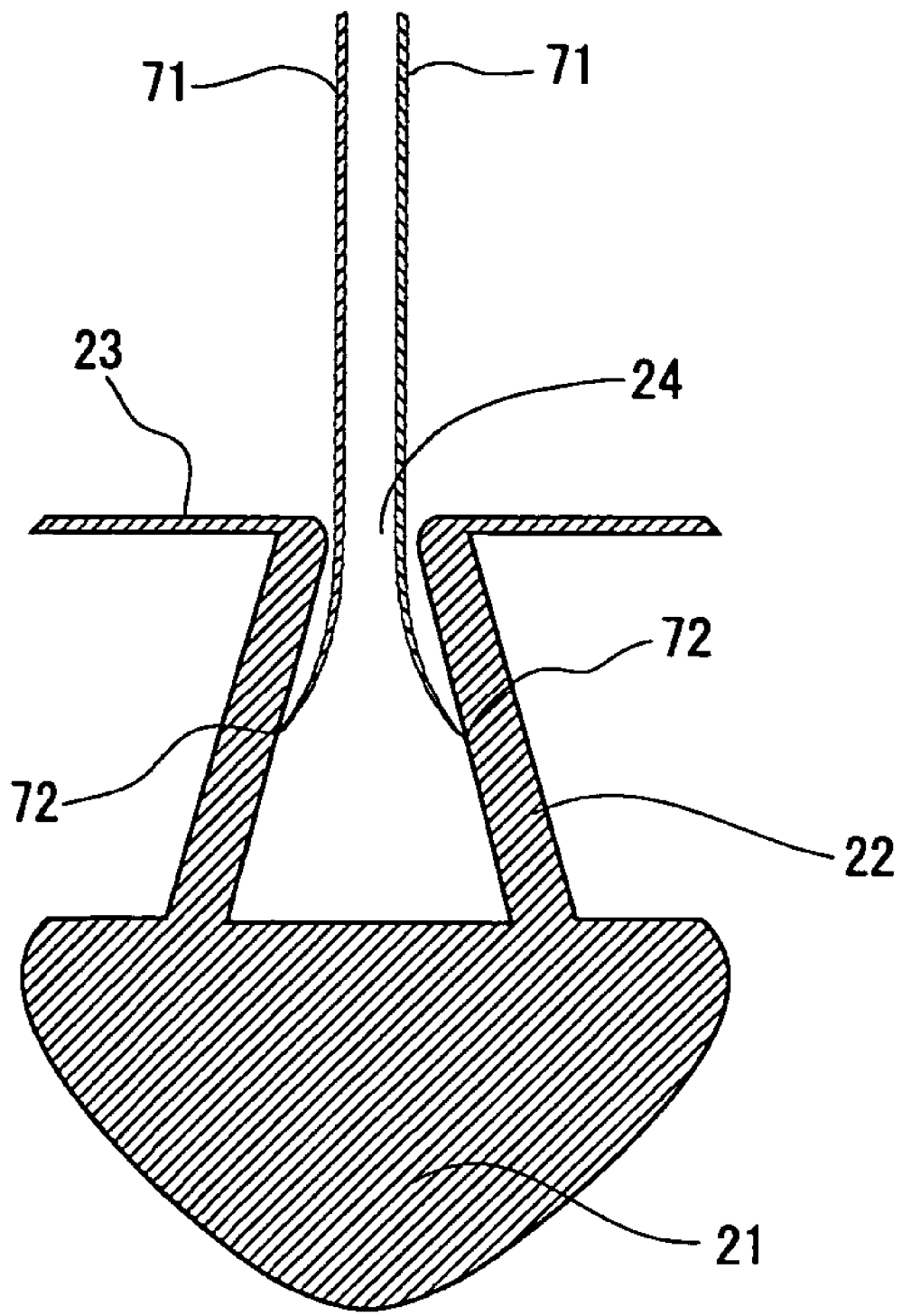
FIG. 39 is a schematic diagram showing a punctal plug according to the present invention.

FIG. 39 shows the thread 71 fixed at the midpoint of the lumen through the inner surface of the shaft.

Figure 40:
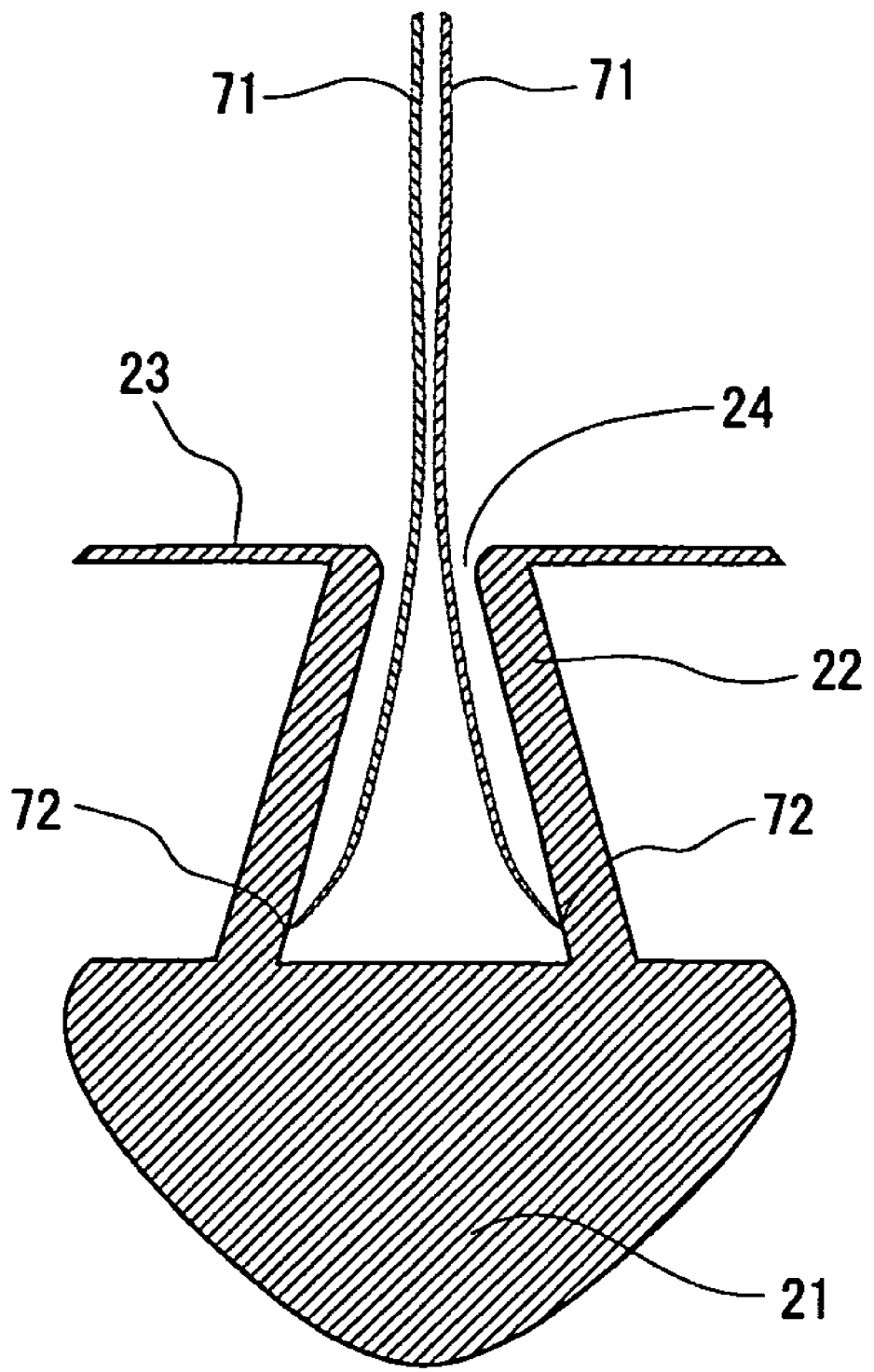
FIG. 40 is a schematic diagram showing a punctal plug according to the present invention.
Figure 41:
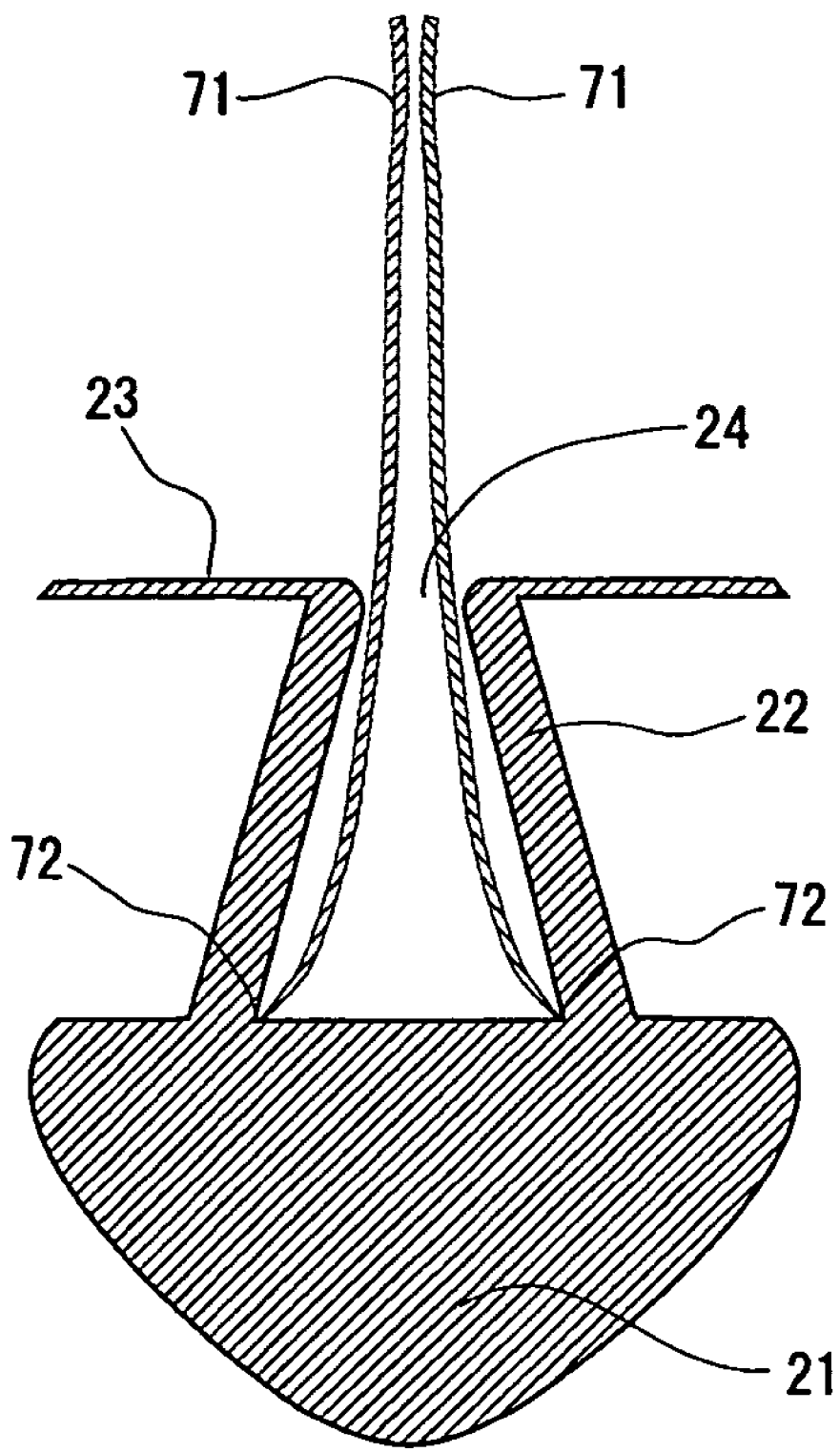
FIG. 41 is a schematic diagram showing a punctal plug according to the present invention.
Figure 42:
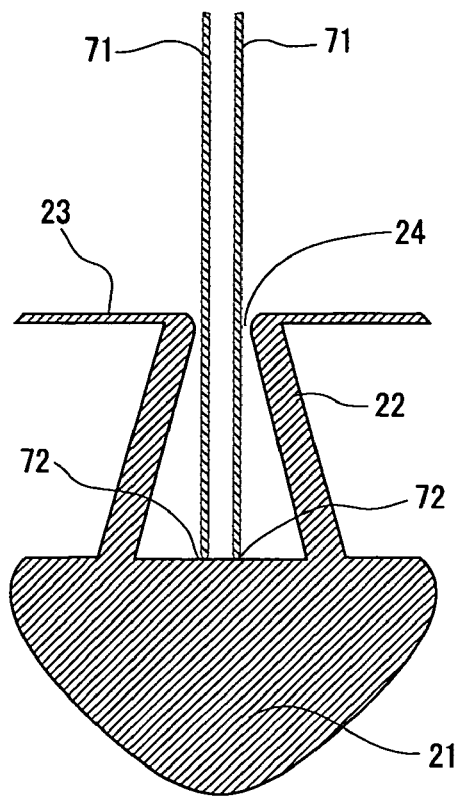
FIG. 42 is a schematic diagram showing a punctal plug according to the present invention.

FIGS. 40~42 show the thread 71 fixed at the deep part of the lumen of the shaft 22.

Figure 43:
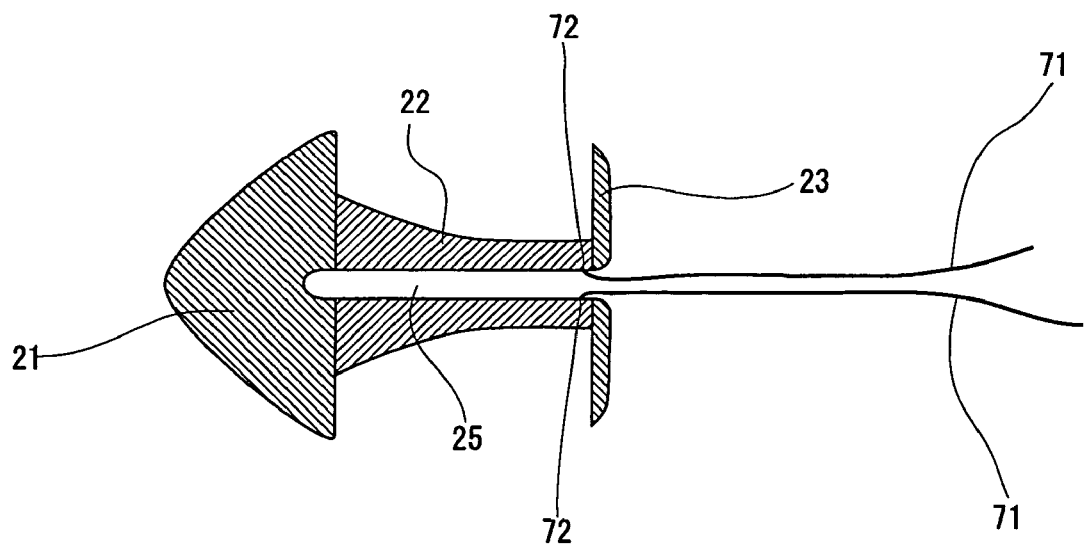
FIG. 43 is a schematic diagram showing a punctal plug according to the present invention.

FIG. 43 shows the thread 71 fixed at the lumen of the shaft 22 near the hole 24.

Figure 44:
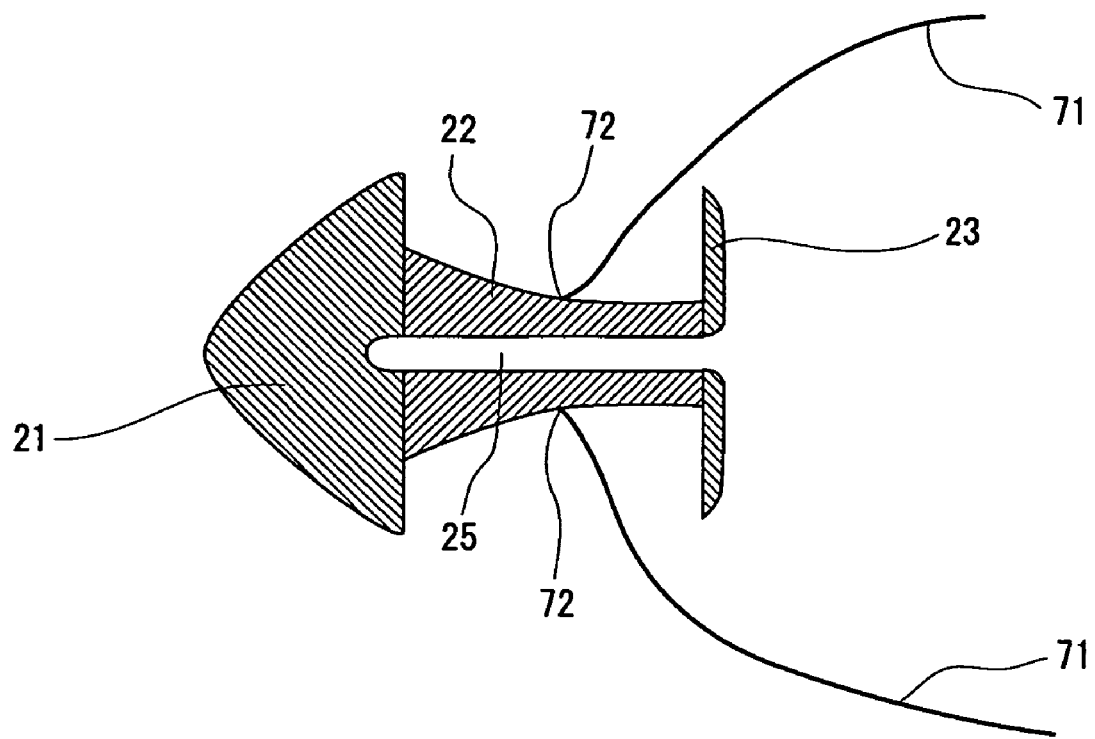
FIG. 44 is a schematic diagram showing a punctal plug according to the present invention.

FIG. 44 shows the thread 71 fixed at the midpoint of the surface of the shaft 22 without entering into the hole 24.

FIG. 45(A) and (B) show the thread 71 fixed at the midpoint and edge of the tip 21 respectively.

The punctal plugs in FIGS. 38~45 above mentioned can be used in the same way as those in FIGS. 11~37.

Figure 46:
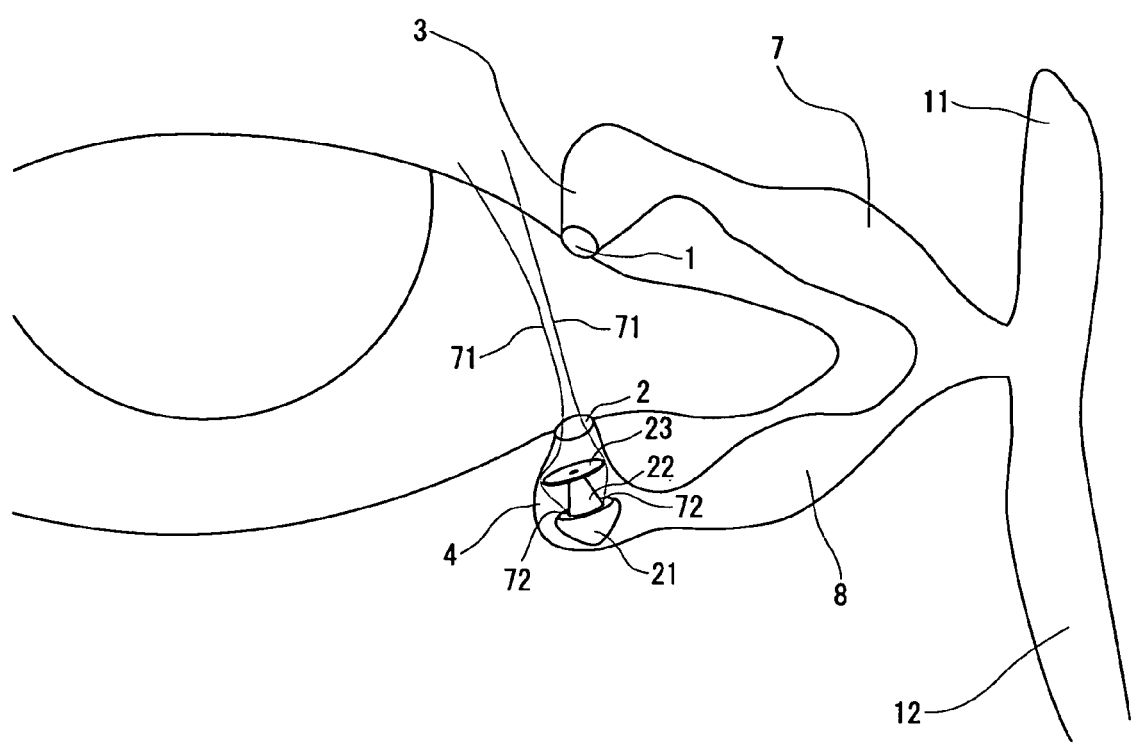
FIG. 46 is an explanatory diagram showing how to insert a punctal plug according to the present invention.
Figure 48:
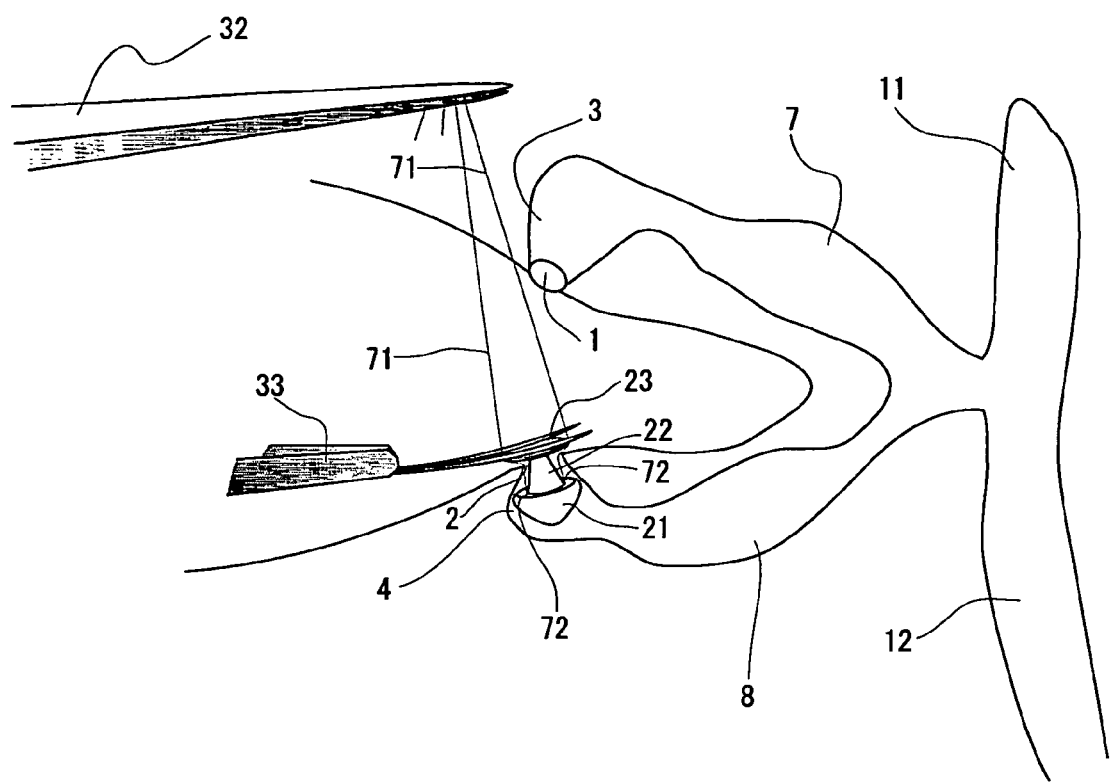
FIG. 48 is an explanatory diagram showing how to insert a punctal plug according to the present invention.
Figure 49:
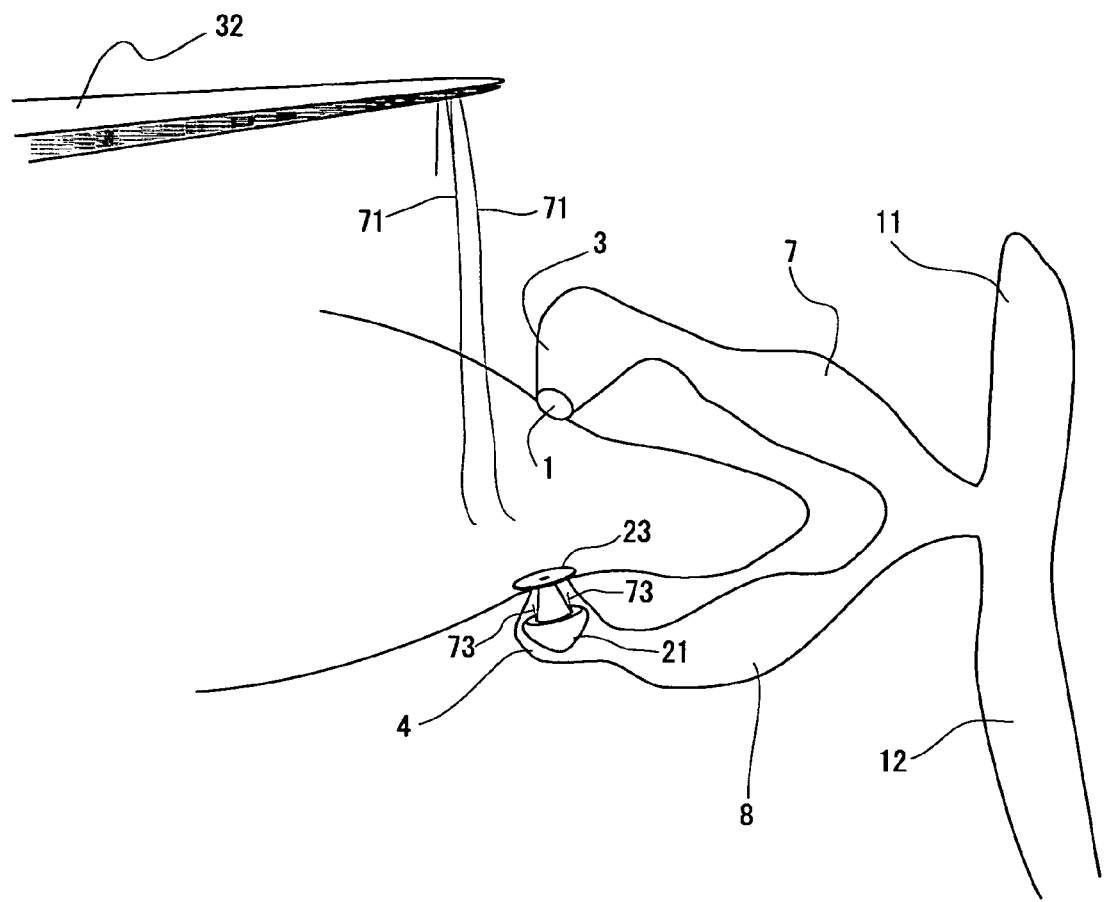
FIG. 49 is an explanatory diagram showing how to insert a punctal plug according to the present invention.

Even if the brim of the threaded punctal plug is included in the lacrimal duct during insertion using metal probe (inserter) as shown in FIG. 46, the brim can be pulled out of the punctum by pulling both sides of the thread 71 and left correctly in place as shown in FIGS. 47~49. As shown in FIGS. 48 and 49, the thread 71 is cut using a small scissors 33 after pulling the brim 23 out of the punctum. Fragment of the thread 73 fixed at the punctal plug is allowed to be left if the tip of the fragment of the thread does not protrude from the punctum as shown in FIG. 49.

Figure 50:
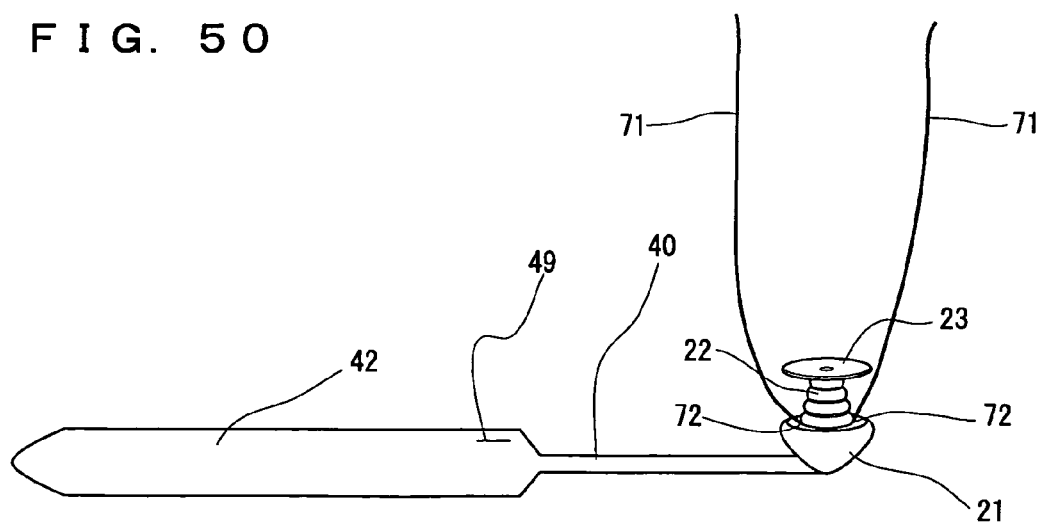
FIG. 50 is a schematic diagram showing other apparatus for intubation according to the present invention.
Figure 51:
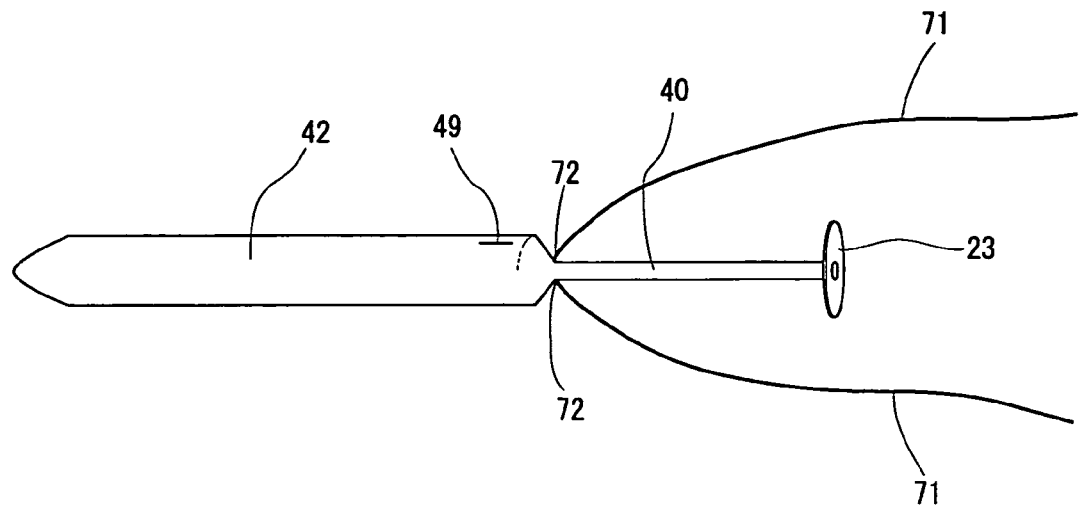
FIG. 51 is a schematic diagram showing other apparatus for intubation according to the present invention.

FIG. 50 shows other apparatus for intubation of the lacrimal duct by the present inventor. This apparatus for intubation of the lacrimal duct having a thinner tube with a sufficient length to cover from the punctum to the lacrimal sac, a punctal plug attached to one end of said thin tube and the thick tube attached to the other end of said thin tube, wherein the thread 71 is fixed at the tip 21 of the plug. It is allowed for the thread 71 to be fixed at the thin tube 40 or the thick tube 42.

Figure 52:
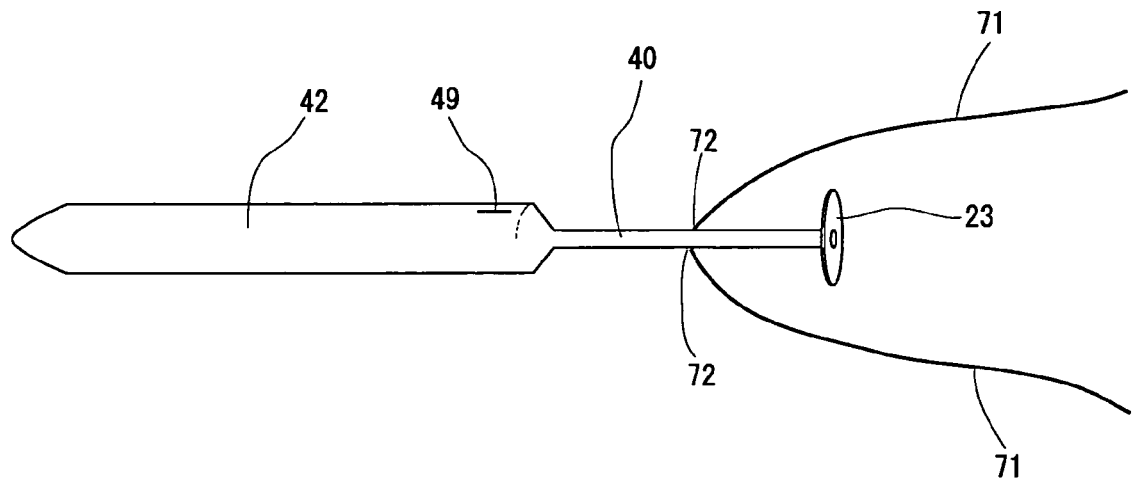
FIG. 52 is a schematic diagram showing other apparatus for intubation according to the present invention.

FIGS. 51~54 show still other apparatus for intubation of the lacrimal duct by the present inventor having a thin tube with a sufficient length to cover the punctum to the lacrimal sac, a brim attached to one end of said thin tube and a thick tube attached to the other end of said thin tube. In FIG. 52, the thread 71 is fixed at the midpoint of the thin tube. In FIG. 53, the thread 71 is fixed at the hole 24 of the brim 23.

An apparatus for intubation of the lacrimal duct shown in FIG. 54, the tube is pushed into the lacrimal duct by a metal probe inserted into the thicker tube from the small cut 49 and the thread 71 is fixed at the thick tube.

Figure 55:
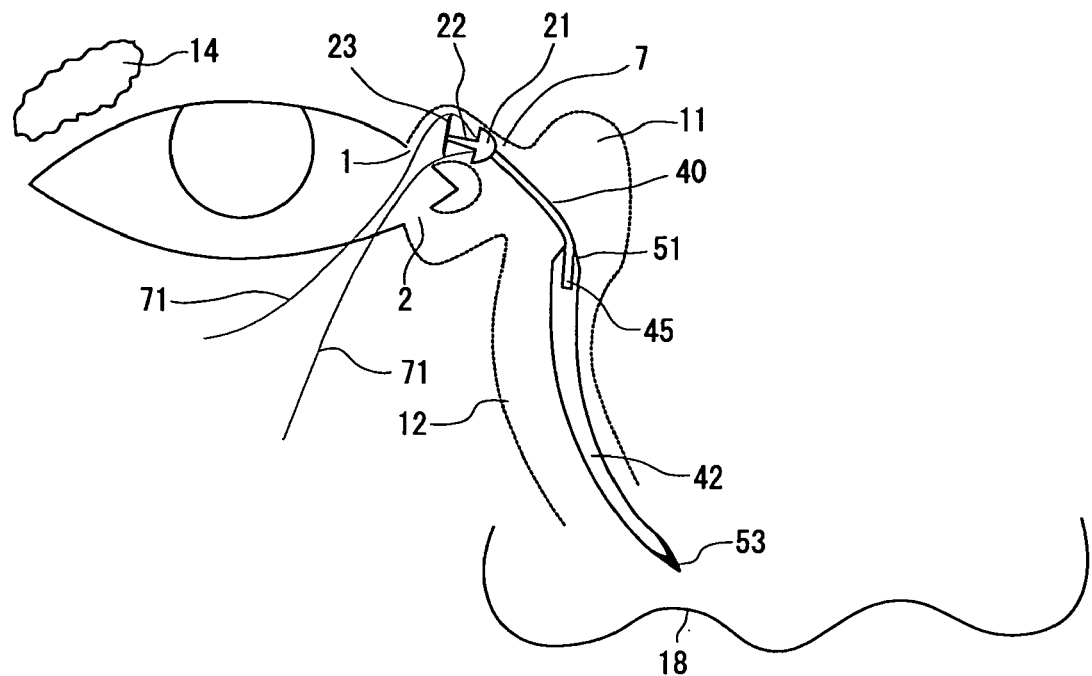
FIG. 55 is an explanatory diagram showing how to use other apparatus for intubation with thread according to the present invention.
Figure 56:
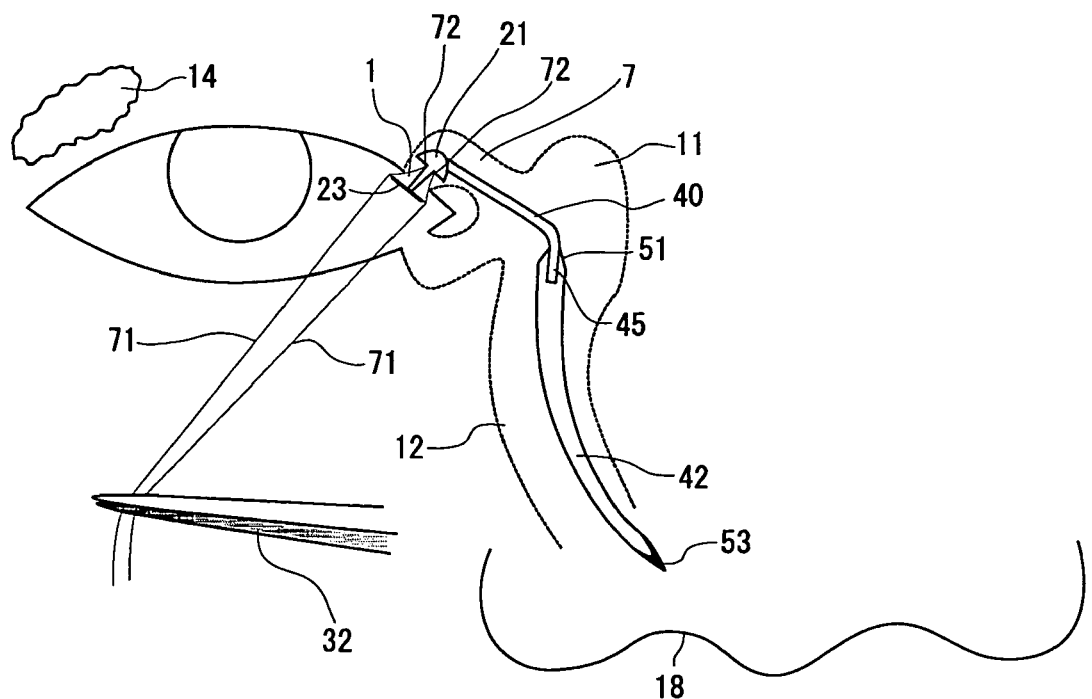
FIG. 56 is an explanatory diagram showing how to use other apparatus for intubation with thread according to the present invention.
Figure 57:
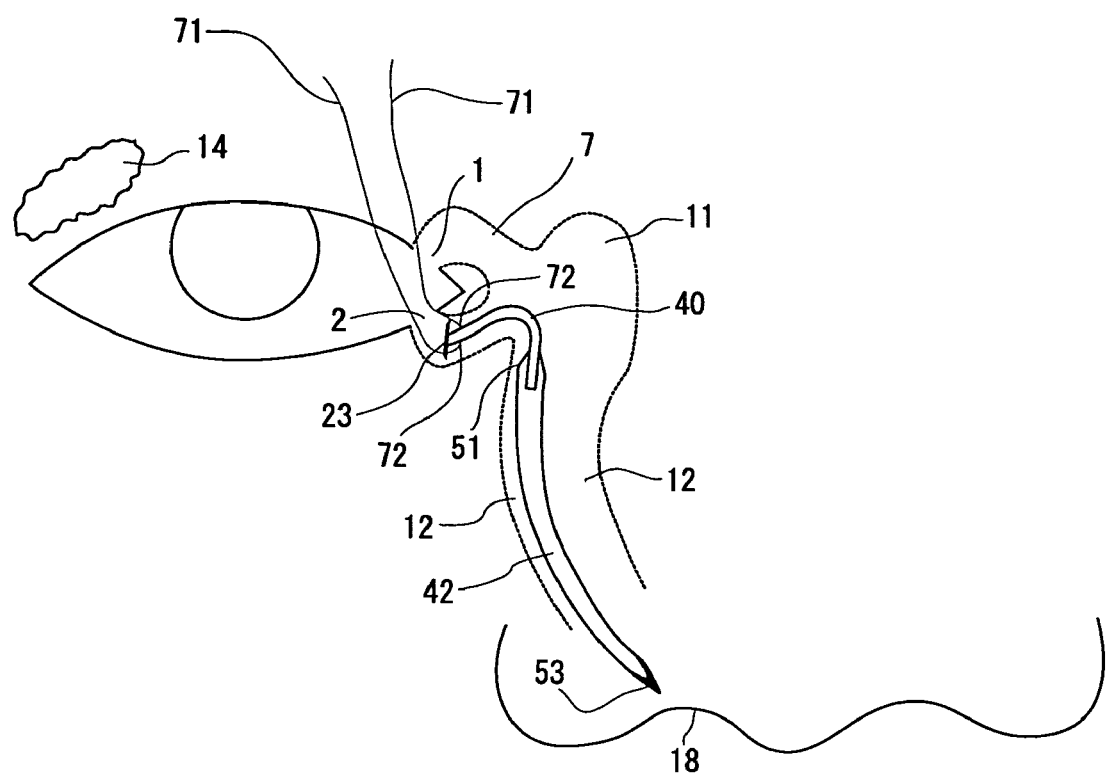
FIG. 57 is an explanatory diagram showing how to use other apparatus for intubation with thread according to the present invention.

FIG. 55 shows the state wherein the brim 23 of the apparatus for intubation shown in FIG. 50 is included in the lacrimal duct, but as shown in FIG. 56 the brim 23 can be pulled out of the punctum using forceps because the thread 71 is fixed at the tip 21 of the punctal plug. FIG. 57 shows the state wherein the brim 23 of an apparatus for intubation of the lacrimal duct shown in FIG. 52 is included in the lacrimal duct from the lower punctum 2, but the brim 23 can be pulled out of the punctum by pulling both sides of the thread because the thread 71 is fixed at the thin tube as shown in FIG. 58.

Next, still other embodiments of the present invention made by the inventor will be explained by referring to FIGS. 59(A), (B) and (C).

FIGS. 59(A), (B)) and (C) are still another punctal plugs by the present inventor, wherein a conical shaped protuberance 81 is attached to the side of the tip portion 21. As shown in FIG. 59(C), the protuberance 81 in the horizontal part of the canalicular 7, 8 makes the punctal plug more stable. The shape of the protuberance 81 is preferably conical in shape, though other shapes also can be adopted. Because the shape of the inner space of the horizontal part of the canaliculus is conical in shape, a conical shaped protuberance 81 is desirable. The protuberance 81 attached to the tip 21 portion of the punctal plug makes the plug more stable and negative pressure generated in the lumen of the canaliculus also contributes stableness in the punctal plug.

The length of the protuberance 81 is preferably 3~7 mm.

In insertion of the punctal plug shown in FIGS. 59(A), (B) and (C), the punctal plug is inserted after the protuberance 81 is inserted into the lacrimal duct using forceps from the punctum which is dilated by a punctal dilator.

In an apparatus for intubation of the lacrimal duct shown in FIGS. 59(A) and (B), the brim 23 included in the lacrimal duct as shown in FIG. 59(C) can be pulled out of the punctum by pulling both sides of the thread simultaneously.

Next, still other embodiments will be explained by referring to FIGS. 60 and 61.

Figure 60:
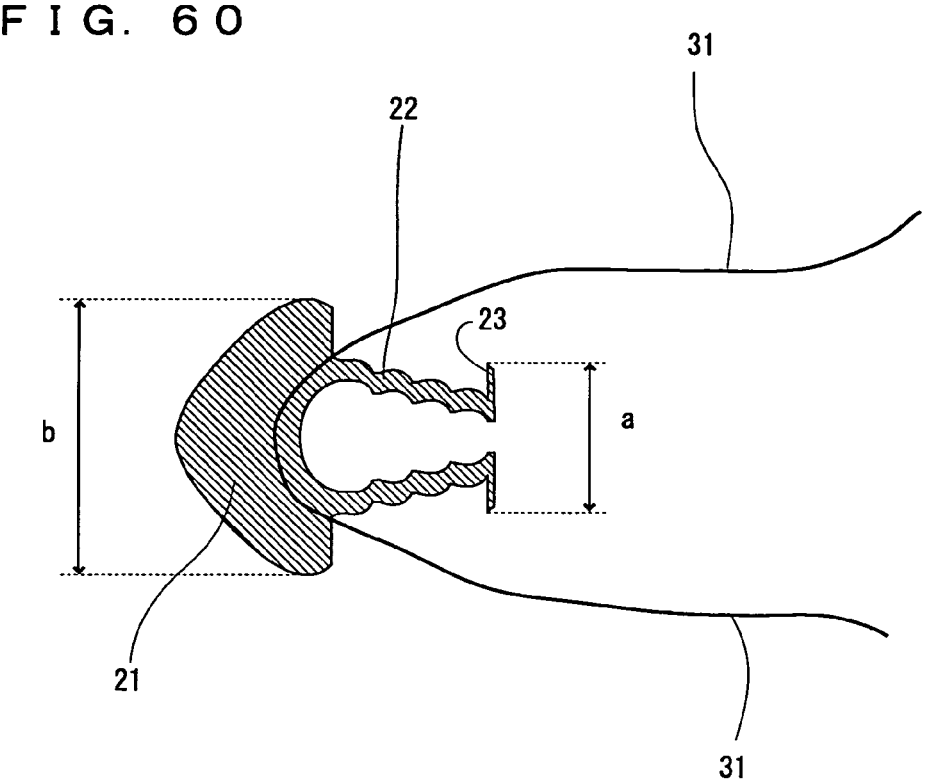
FIG. 60 is a sectional view to explain an outline of other punctal plugs with thread according to the present invention.

In the punctal plug in FIG. 60, the diameter (a) of the brim 23 is far smaller than the diameter (b) of the tip portion 21. Therefore, the brim 23 is easily included in the lacrimal duct following insertion of the tip portion 21 from the punctum. But the brim can be pulled out of the lacrimal duct and can be left in place correctly because the thread 31 is penetrates into the tip portion 21. FIG. 61 shows the thread 31 penetrating the tip portion 21 and the diameter (a) of the brim 23 is far smaller than the diameter (b) of the tip portion 21, so the brim 23 is easily included in the lacrimal duct. But the brim 23 can be left in place correctly by pulling it out because the thread 31 penetrates the tip portion 21. The brim 23 in FIGS. 60 and 61, is not pulled out immediately; the brim 23 is pulled out of the punctum after a short wait for the opening of the punctum to shrink by contraction.

The mark 72 stands for the fixed point for thread 71 in the various parts of the punctal plug and the apparatus for intubation.

As above mentioned, safety and comfort are markedly improved by thread which is penetrated into the punctal plug and the apparatus for intubation of the lacrimal duct.

Figure 61:
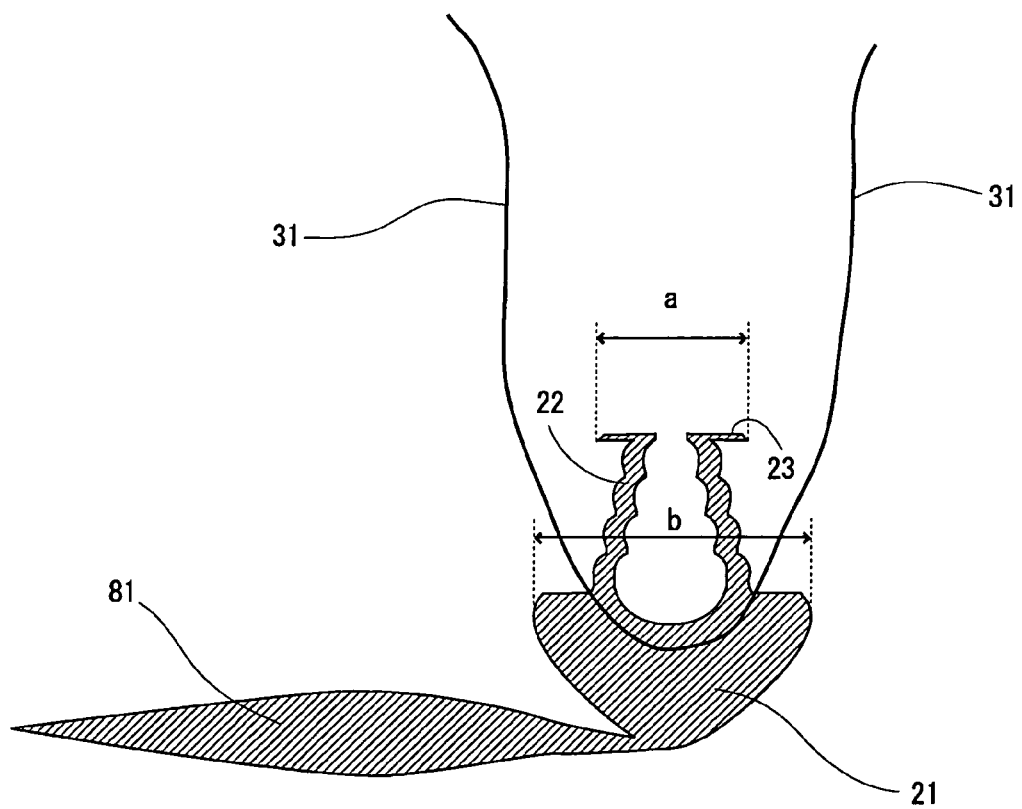
FIG. 61 is a sectional view to explain an outline of other punctal plugs with thread according to the present invention.
Figure 62:
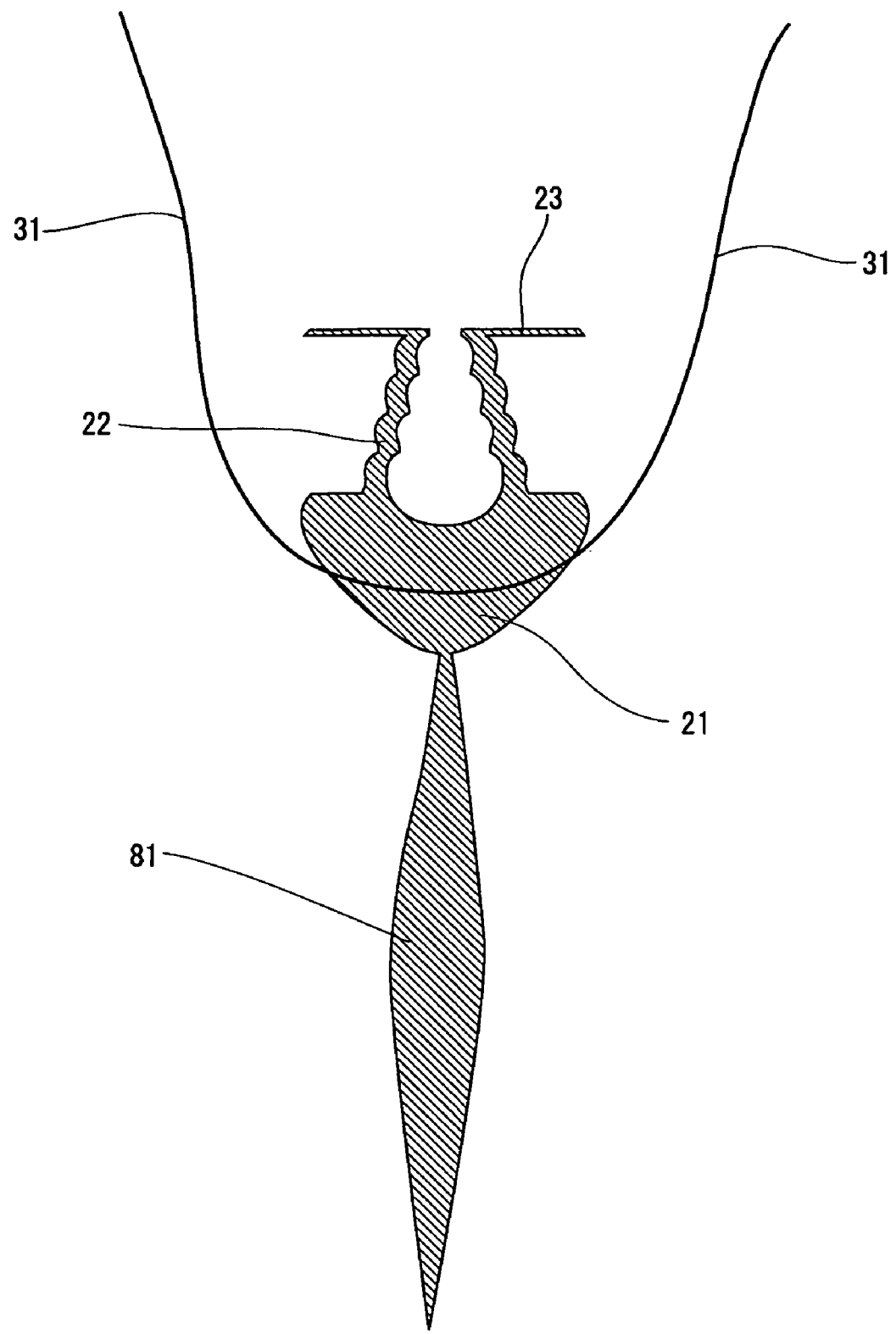
FIG. 62 is a sectional view to explain an outline of other punctal plugs with thread according to the present invention.
Figure 63:
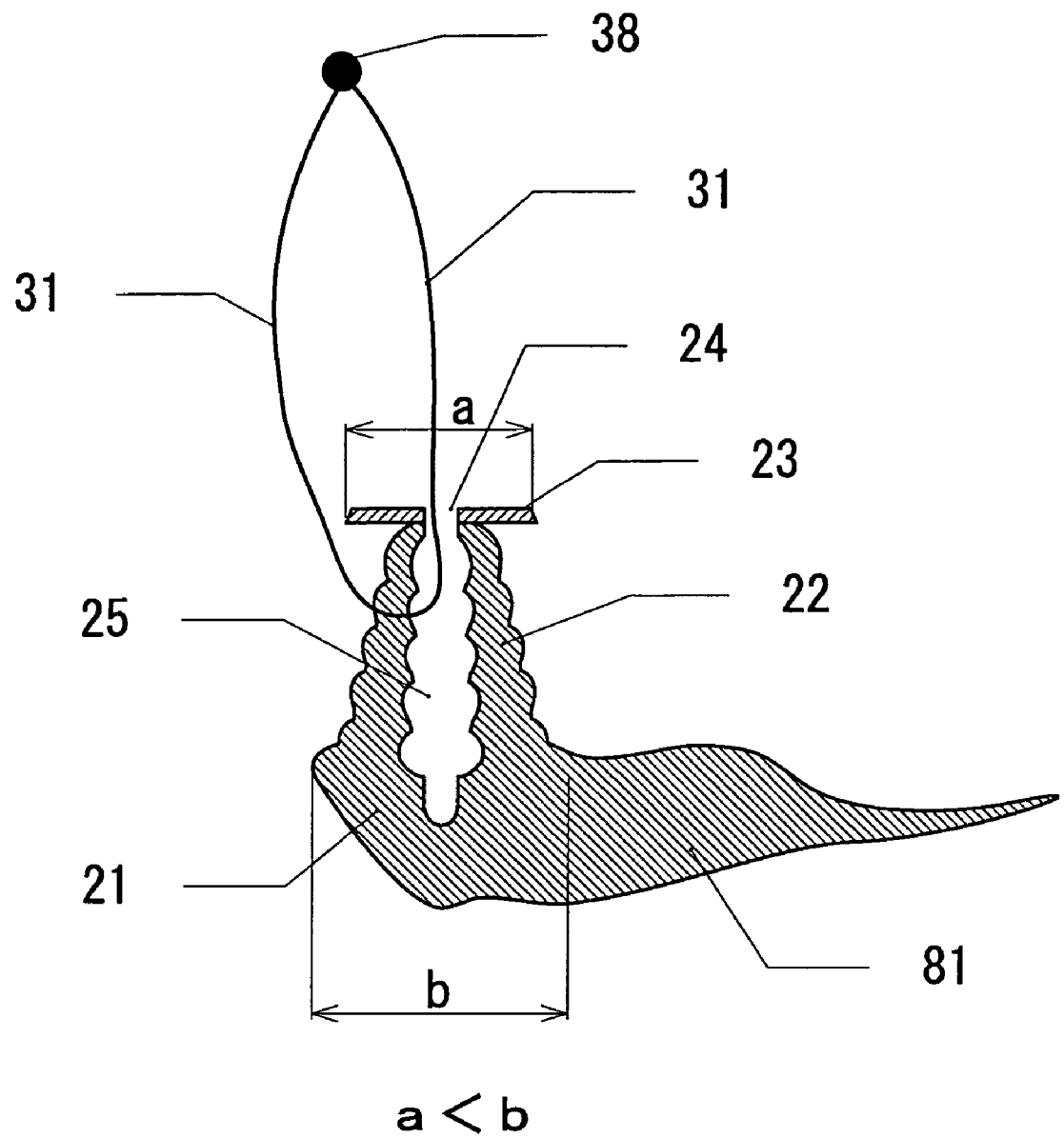
FIG. 63 is a sectional view to explain an outline of other punctal plugs with thread according to the present invention.

As shown in FIG. 62, a spindle shaped protuberance 81 is allowed to be attached to the apex of the tip portion 21, and the longitudinal length of the tip portion 21 is shorter than that of the punctal plug shown in FIG. 61.

As shown in FIGS. 63~73, the threaded punctal plug with the protuberance 81 is also useful. The protuberance 81 also prevents the brim 23 from entering into the canaliculus.

Figure 65:
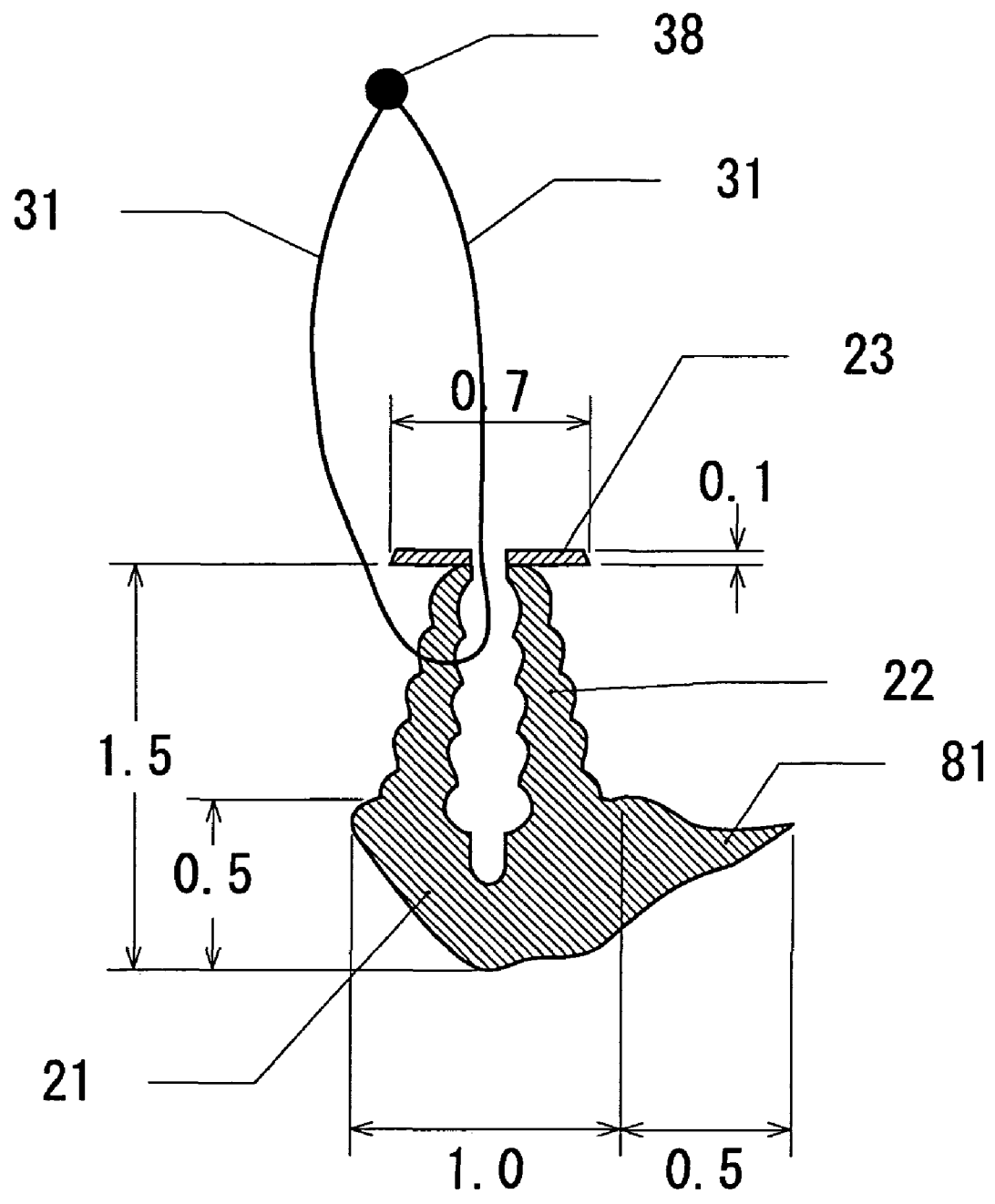
FIG. 65 is a sectional view to explain an outline of other punctal plugs with thread according to the present invention.
Figure 66:
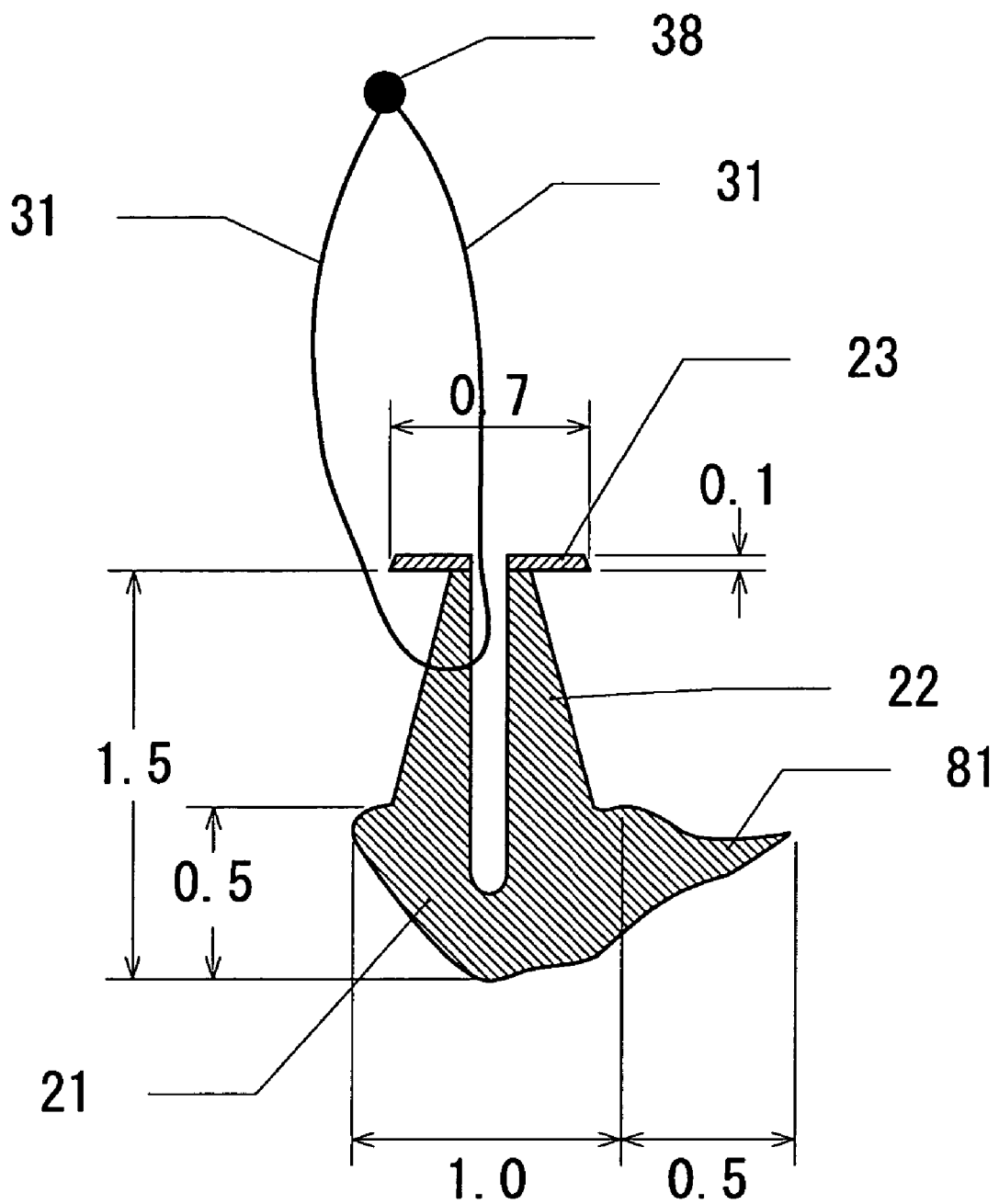
FIG. 66 is a sectional view showing the dimension of a typical example according to the present invention.

FIGS. 65~66 show the dimension of a typical example according to the present invention.

Figure 67:
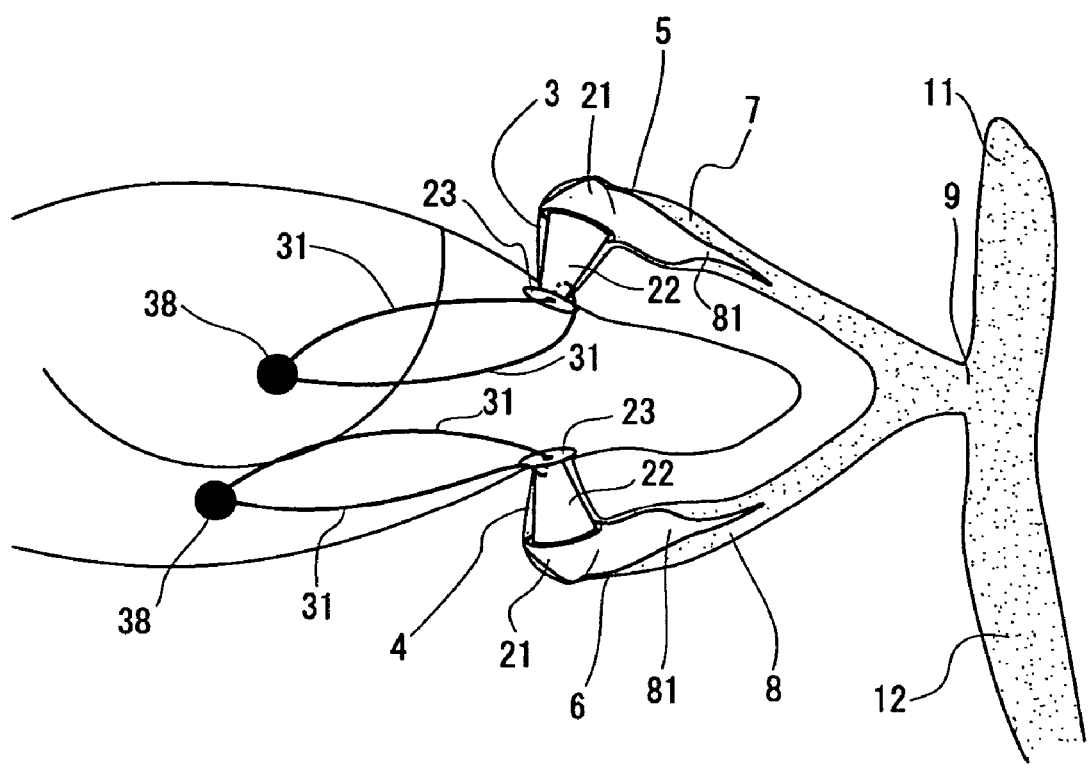
FIG. 67 is an explanatory diagram showing how to insert a punctal plug according to the present invention.
Figure 68:
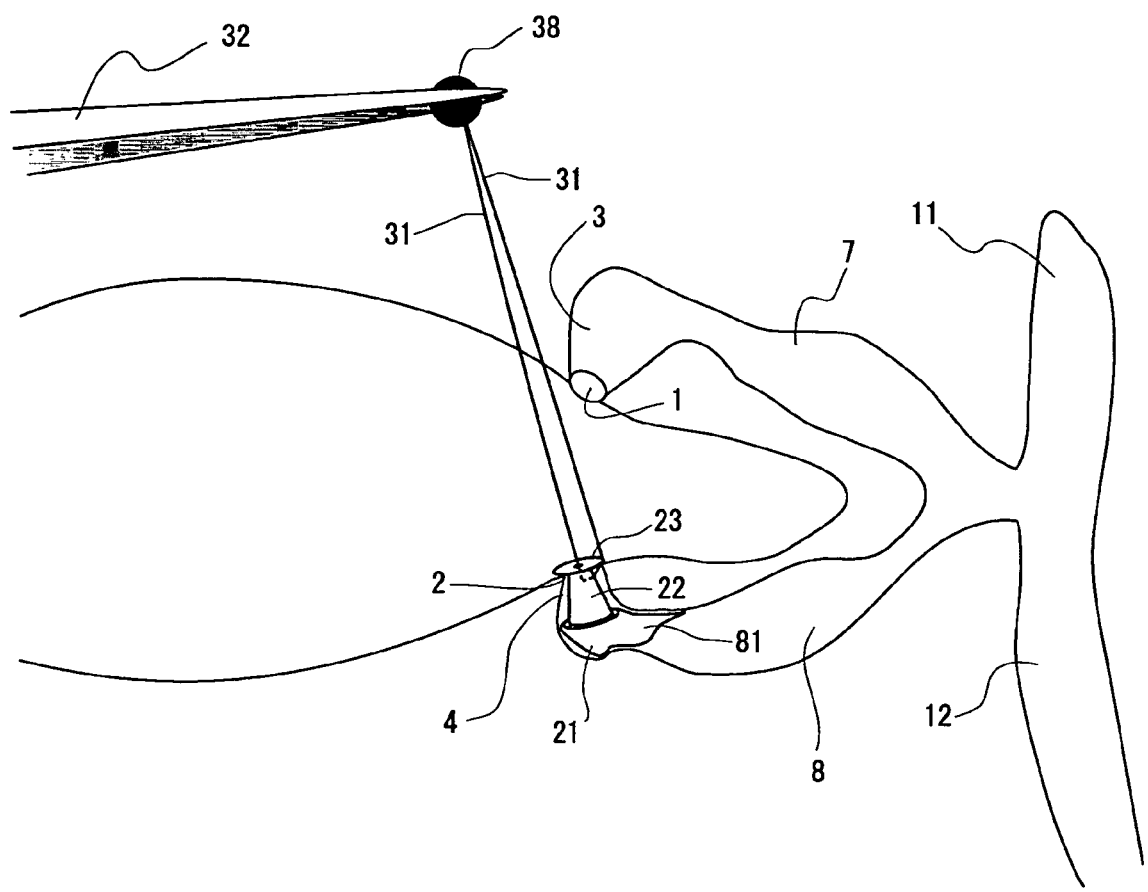
FIG. 68 is an explanatory diagram showing how to insert a punctal plug according to the present invention.

Even if a brim 23 is inside the canaliculus as shown in FIGS. 67-68, the brim 23 is taken out by pulling the thread with forceps from the punctum, and the punctal plug can be correctly placed.

Figure 69:
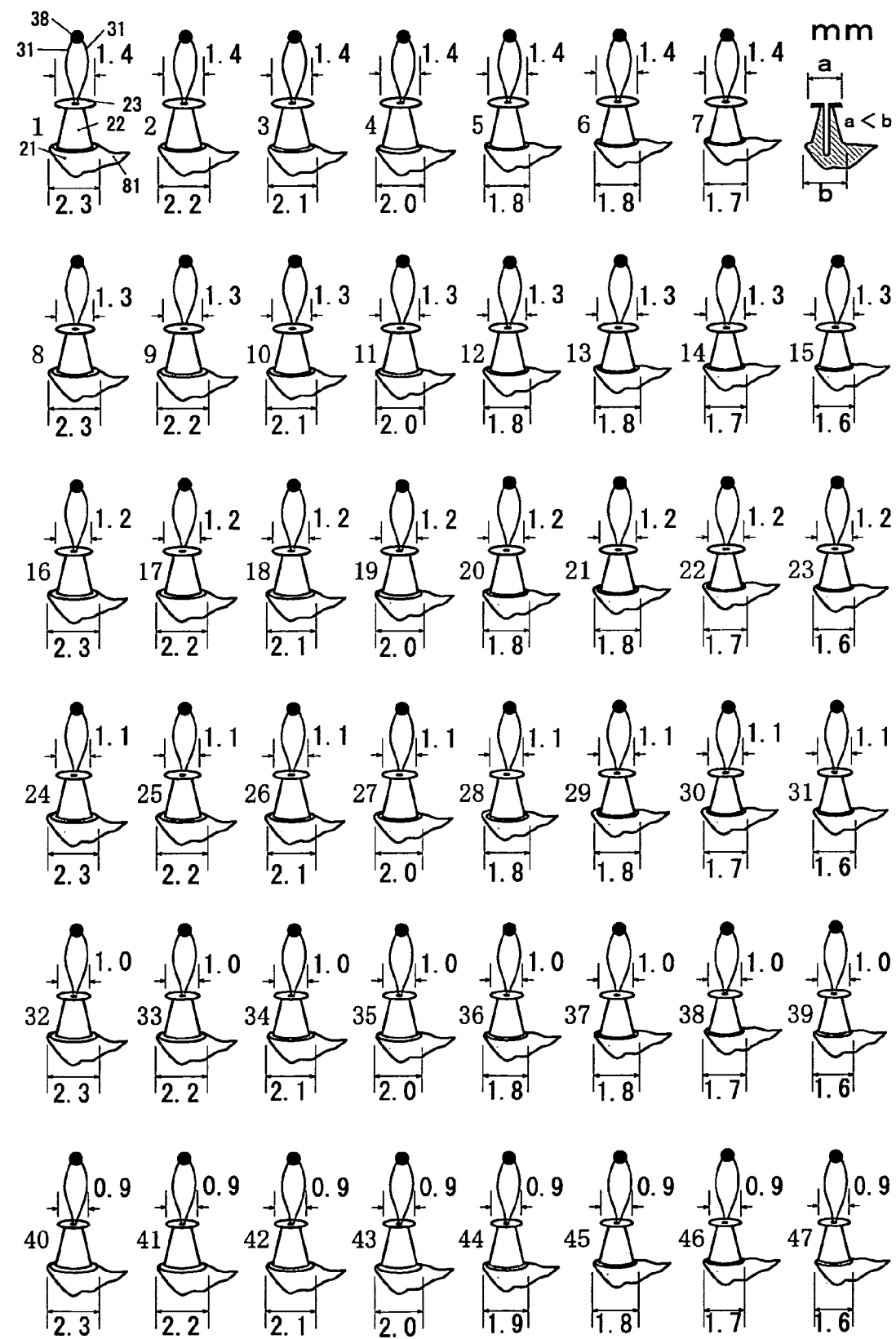
FIG. 69 is an explanatory diagram showing the dimension of other punctal plugs with thread according to the present invention.
Figure 70:
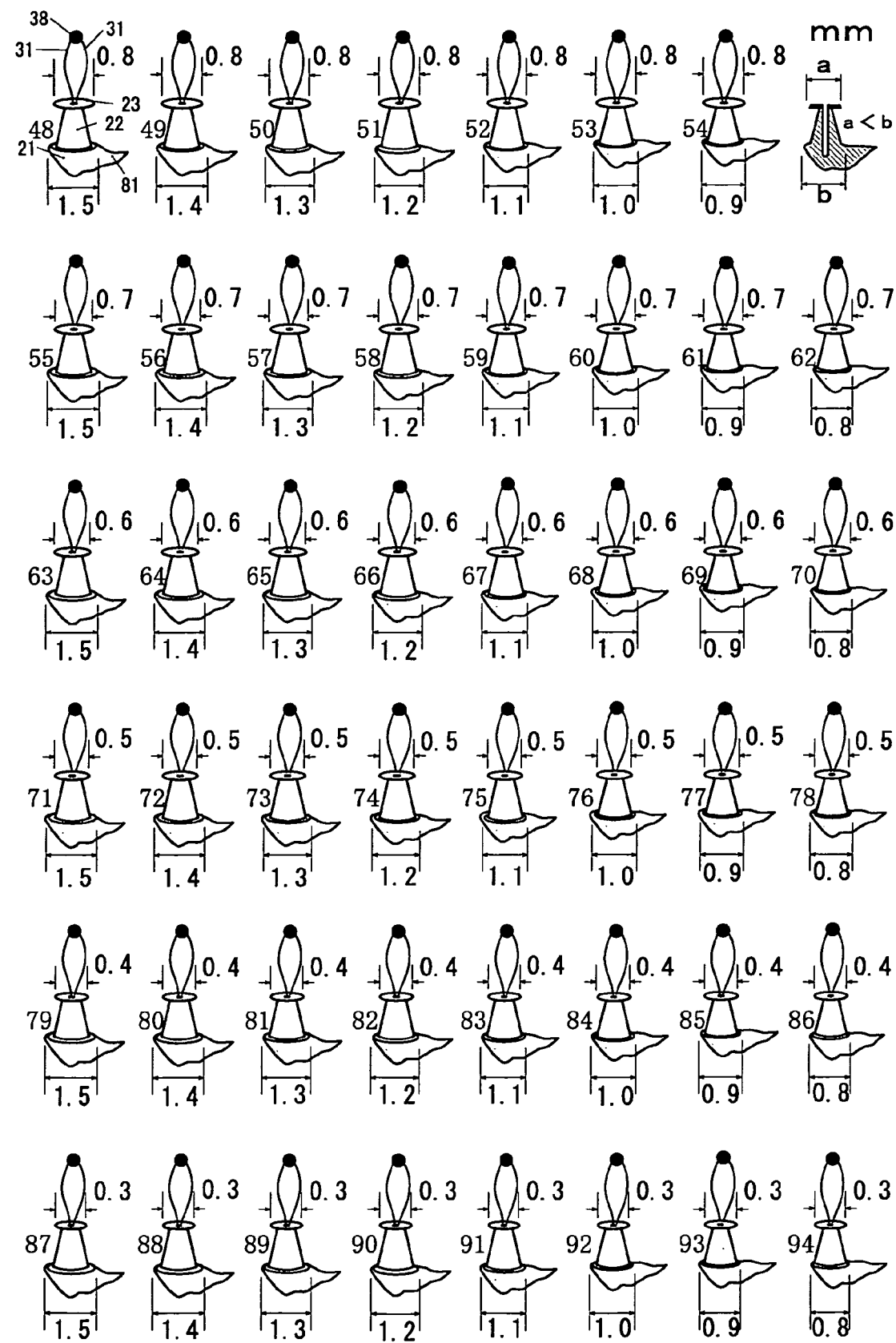
FIG. 70 is an explanatory diagram showing the dimension of other punctal plugs with thread according to the present invention.

Therefore, as shown in FIGS. 69-70, various sized punctal plugs can be produced to present the most appropriate sized punctal plug for each individual according to the size of the punctum and canaliculus because the punctal plugs with thread shown in FIGS. 63~73 can be placed safely and surely even if using the smallest sized brim 23.

Figure 71:
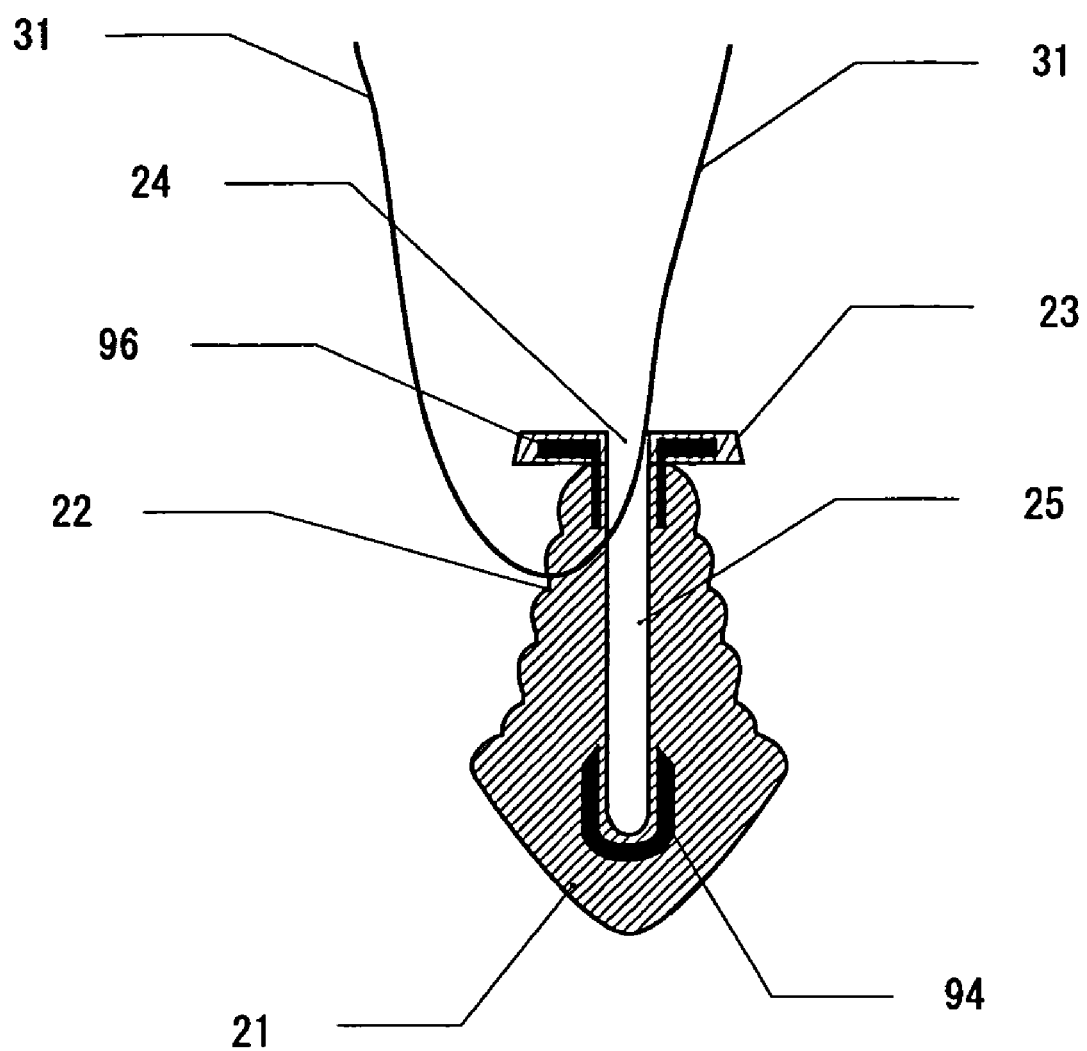
FIG. 71 is a sectional view to explain an outline of other punctal plugs with thread according to the present invention.
Figure 72:
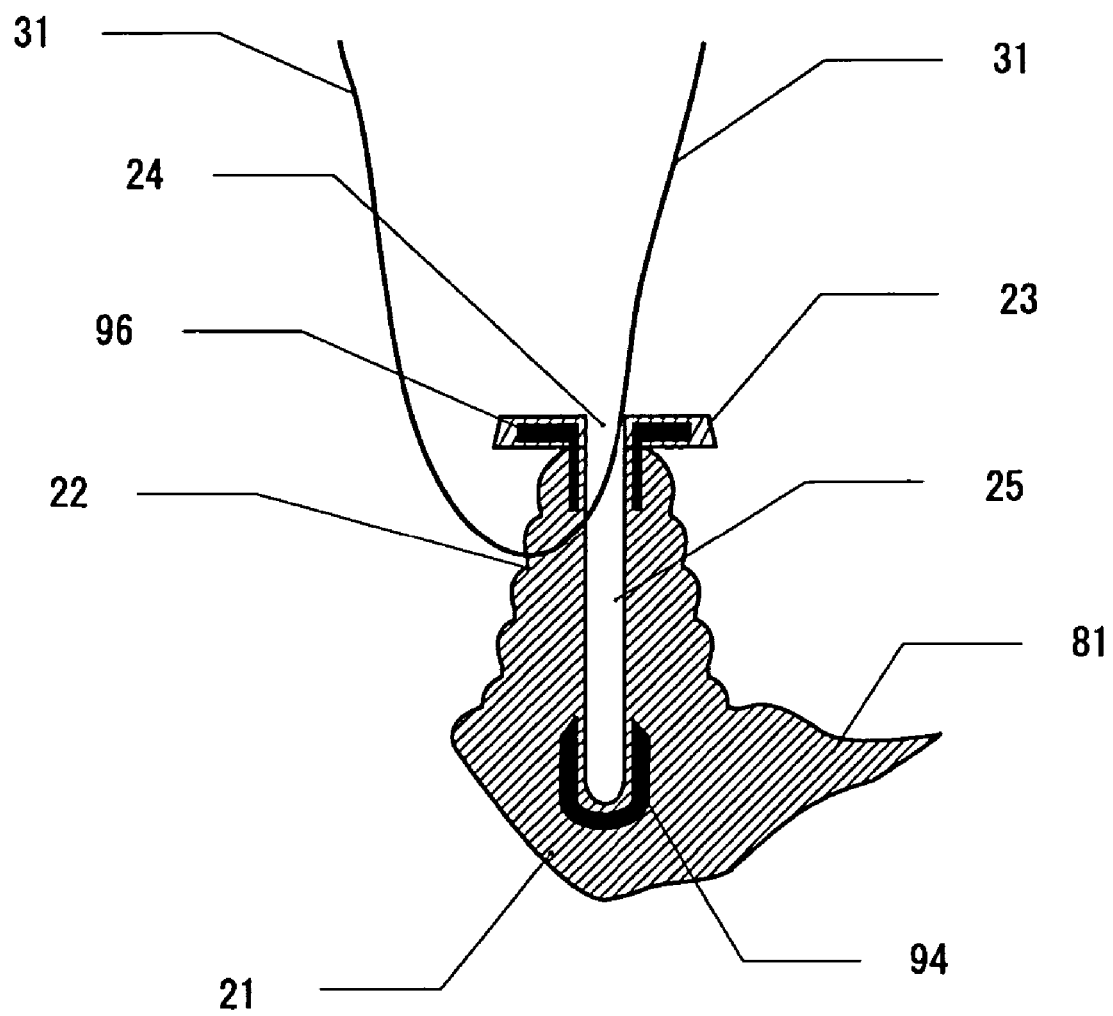
FIG. 72 is a sectional view to explain an outline of other punctal plugs with thread according to the present invention.
Figure 73:
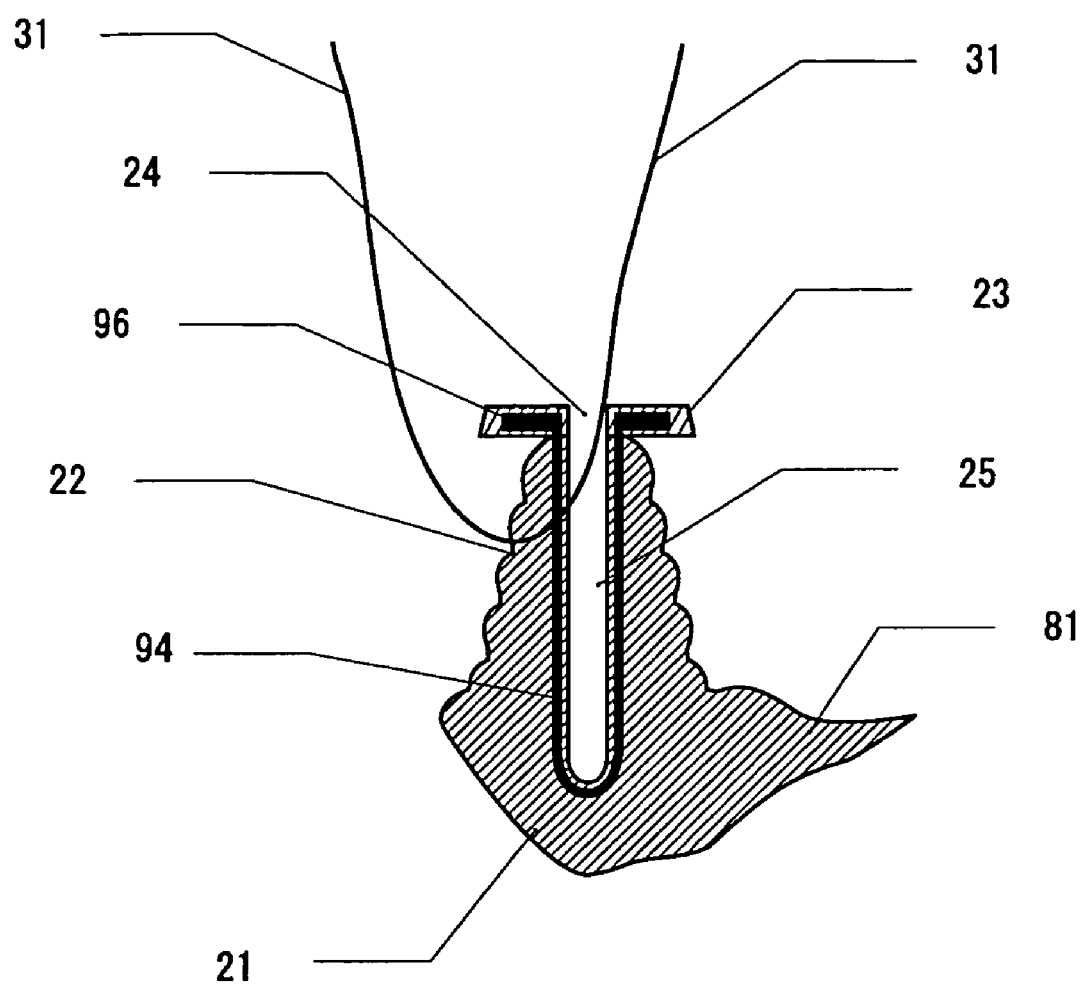
FIG. 73 is a sectional view to explain an outline of other punctal plugs with thread according to the present invention.
Figure 74:
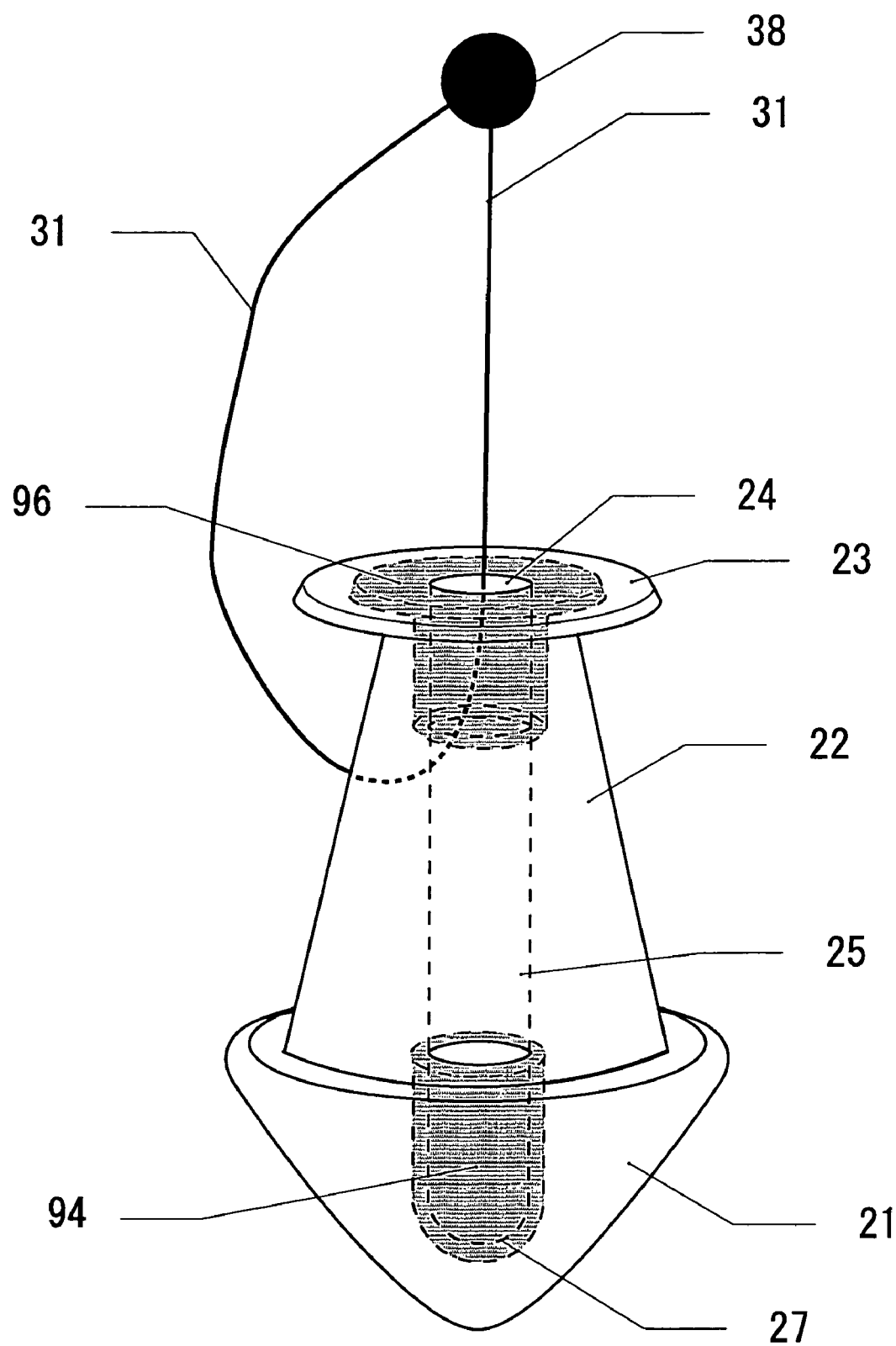
FIG. 74 is a schematic diagram showing other punctal plugs with thread according to the present invention.

In the punctal plug shown in the FIGS. 71-73, a reinforcement member made of a material with excellent character in the pulling strength, heat-resistance, anti-fatigability and radiopaque, such as stainless steel, piano wire and plastics is arranged in the brim 23 and the shaft 22 and the tip of the cavity 27.

The brim 23 is reinforced with the disk-shaped reinforcement member 95.

The shaft 22 is reinforced with the cylinder-shaped reinforcement member.

The tip of the cavity 27 is reinforced with the cup-shaped reinforcement member 94.

The reinforced punctal plug according to the present invention has the following advantages: the punctal plug is not easily penetrated by a metal probe, and an irretrievable punctal plug in the lacrimal passage can be detected by X-ray.

The invention claimed is:

1. A method of inserting a punctal plug into a punctum canaliculus, the punctal plug comprising a shaft, a tip portion attached to one end of the shaft, a brim attached to the other end of the shaft, and a fine thread, having two ends, removably inserted into a part of the punctal plug, said method comprising the steps of:
   inserting said punctal plug into a punctum canaliculus;
   thereafter, if the punctal plug is not placed in a proper position, simultaneously pulling both ends of the fine thread so that the punctal plug is pulled out of the punctum canaliculus, and then reinserting said punctal plug into a punctum canaliculus; and
   if the punctal plug is placed in the proper position pulling one end of the fine thread so that the thread is pulled out of the punctal plug and then removed from the punctal plug.

2. The method of inserting a punctal plug as defined in claim 1, wherein the brim is disc-shaped.

3. The method of inserting a punctal plug as defined in claim 2, wherein the diameter of the brim is 0.4 mm or less.

4. The method of inserting a punctal plug as defined in claim 2, wherein a protuberance is attached to the tip portion.

5. The method of inserting a punctal plug as defined in claim 1, wherein the diameter of the brim is 0.4 mm or less.

6. The method of inserting a punctal plug as defined in claim 5, wherein a protuberance is attached to the tip portion.

7. The method of inserting a punctal plug as defined in claim 1, wherein a protuberance is attached to the tip portion.

8. The method of inserting a punctal plug as defined in claim 1, wherein the diameter of the thread is 0.02-0.05 mm.

9. A method of insertion of a punctal plug into a punctum-canaliculus, the punctal plug comprising a shaft, a tip portion attached to one end of the shaft, a brim attached to the other end of the shaft, and a fine thread for removable insertion thereof into one of said tip portion, said shaft, and said brim, or into said tip portion and shaft, or into said shaft and said brim, wherein both ends of the fine thread extend out of the punctal plug;
   said method including the steps of:
   inserting said punctal plug into a punctum canaliculus;
   thereafter, if the punctal plug is not placed in a proper position, pulling two ends of the fine thread and pulling the brim out of the canaliculus, and
   thereafter, if the punctal plug is placed in the proper position, pulling one end of the fine thread and pulling the fine thread out of the punctal plug.

10. The method defined in claim 9, wherein said fine thread is 0.05 mm or less in diameter and is used to pull out the brim, which is first lodged in the canaliculus, by pulling two ends of the fine thread so that the brim can be pulled out of the canaliculus.

11. The method defined in claim 9, wherein the diameter of the brim is 0.4 mm or less.

12. The method defined in claim 9, wherein a protuberance is attached to the tip portion.

13. The method defined in claim 9, wherein the brim, the shaft, and the tip portion are reinforced by a reinforcement member.

14. The method defined in claim 9, wherein the plug has at least one hole allowing the fine thread to penetrate the plug through the tip portion, the shaft, or the brim.

* * * * *